US010220081B2

(12) United States Patent
Ware et al.

(10) Patent No.: US 10,220,081 B2
(45) Date of Patent: *Mar. 5, 2019

(54) METHODS OF MODULATING HVEM, BTLA AND CD160 CIS COMPLEX RESPONSE OR SIGNALING ACTIVITY WITH SOLUBLE LIGHT POLYPEPTIDE SEQUENCES

(71) Applicant: LA JOLLA INSTITUTE FOR ALLERGY AND IMMUNOLOGY, La Jolla, CA (US)

(72) Inventors: Carl F. Ware, Solana Beach, CA (US); Timothy C. Cheung, Wollstonecraft (AU); Marcos Steinberg, San Diego, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/175,892

(22) Filed: Feb. 7, 2014

(65) Prior Publication Data

US 2014/0220051 A1 Aug. 7, 2014

Related U.S. Application Data

(63) Continuation of application No. 12/534,658, filed on Aug. 3, 2009, now abandoned, which is a continuation-in-part of application No. PCT/US2009/049968, filed on Jul. 8, 2009, said application No. 12/534,658 is a continuation-in-part of application No. 11/721,308, filed as application No. PCT/US2005/044296 on Dec. 9, 2005, now abandoned.

(60) Provisional application No. 61/078,997, filed on Jul. 8, 2008, provisional application No. 60/700,636, filed on Jul. 19, 2005, provisional application No. 60/635,034, filed on Dec. 9, 2004.

(51) Int. Cl.
*A61K 39/00* (2006.01)
*C07K 16/28* (2006.01)

(52) U.S. Cl.
CPC ...... *A61K 39/0005* (2013.01); *C07K 16/2803* (2013.01); *C07K 16/2818* (2013.01); *C07K 16/2878* (2013.01); *C07K 2317/73* (2013.01); *C07K 2317/74* (2013.01); *C07K 2317/75* (2013.01); *C07K 2317/76* (2013.01); *C07K 2319/30* (2013.01); *G01N 2333/70578* (2013.01)

(58) Field of Classification Search
None
See application file for complete search history.

(56) References Cited

U.S. PATENT DOCUMENTS

| 8,058,402 B2 * | 11/2011 | Granger | C07K 16/2875 530/387.3 |
| 8,349,320 B2 * | 1/2013 | Ware | A61K 38/177 424/130.1 |
| 9,700,606 B2 * | 7/2017 | Ware | A61K 39/0005 |
| 2003/0060605 A1 * | 3/2003 | Ware | 530/388.3 |
| 2003/0215442 A1 * | 11/2003 | Fraser et al. | 424/131.1 |
| 2007/0292435 A1 | 12/2007 | Ware | |

FOREIGN PATENT DOCUMENTS

WO 2006/063067 A2 6/2006

OTHER PUBLICATIONS

Granger et al. (Cytokine & Growth Factor Reviews, 2003, p. 289-296).*
Zhang e tal. (J. Clin. Invest. 2002, p. 1335-1344).*
Cai, G., et al., CD160 Inhibits Activation of Human CD4+ T Cells Through Interaction with Herpesvirus Entry Mediator, Nature Immunology, 2008, 9(2):176-185.
Cheung, T.C., et al., Evolutionary Divergent Herpesvirus Modulate T Cell Activation by Targeting the Herpesvirus Entry Mediator Cosignaling Pathway, PNAS, 2005, 102(37):13218-13223.
Cheung, T.C., et al., Unconventional Ligand Activation of Herpesvirus Entry Mediator Signals Cell Survival, PNAS 14, 2009, 106(15):6244-6249.
Compaan, D.M., et al., Attenuating Lymphocyte Activity: the Crystal Structure of the BTLA-HVEM Complex, J. Biol. Chem., 2005, 280(47):39553-39561.
Nelson, C., et al., Structural Determinants of Herpesvirus Entry Mediator Recognition by Murine B and T Lymphocyte Attenuator, J. of Immunology, 2008, 180:940-947.
Ware, C.F., Targeting Lymphocyte Activation Through the Lymphotoxin and Light Pathways, Immunol Rev., 2008, 223:186-201.
Gonzalez, et al., A Coreceptor Interaction Between the CD28 and TNF Receptor Family Members B and T Lymphocyte Attenuator and Herpesvirus Entry Mediator, Pro. Natl. Acad. Sci., 2005, 102(4):1116-1121.
Kobrin, et al.; A V Region Mutation in a Phosphocholine-Binding Monoclonal Antibody Results in Loss of Antigen Binding, The Journal of Immunology, 1991, 146:2017-2020.
Sedy, et al., B and T Lymphocyte Attenuator Regulates T Cell Activation Through Interaction With Herpesvirus Entry Mediator, Nature Immunology, 2005, 6(1):90-98.
Singh, et al., Modeling and Predicting Clinical Efficacy for Drugs Targeting the Tumor Milieu, Nature Biotechnology, 2012, 30(7):648-657.

* cited by examiner

*Primary Examiner* — Agnieszka Boesen
(74) *Attorney, Agent, or Firm* — Pillsbury Winthrop Shaw Pittmann LLP

(57) ABSTRACT

The invention provides HVEM cis complexes which include, for example, HVEM/BTLA, HVEM/CD160 and HVEM/gD cis complexes. The invention provides ligands and agents that bind to HVEM cis complexes, such as antibodies. The invention further provides methods of use of the HVEM cis complexes, and the ligands and agents (e.g., LIGHT polypeptide sequence) that bind to the HVEM cis complexes.

11 Claims, 42 Drawing Sheets

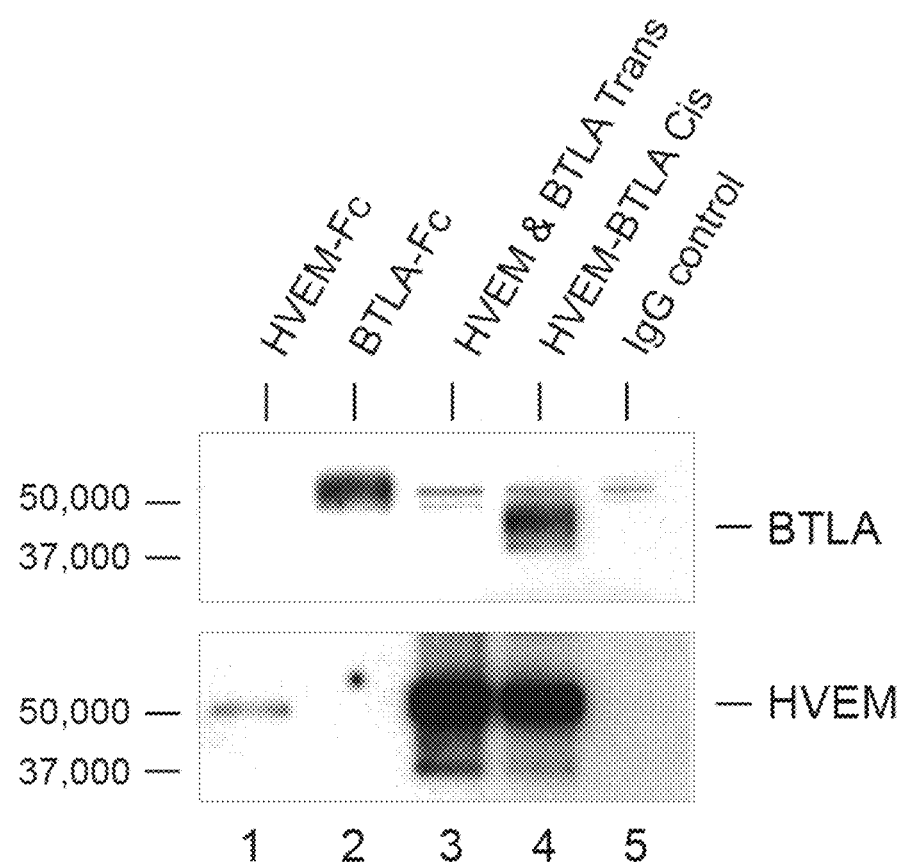

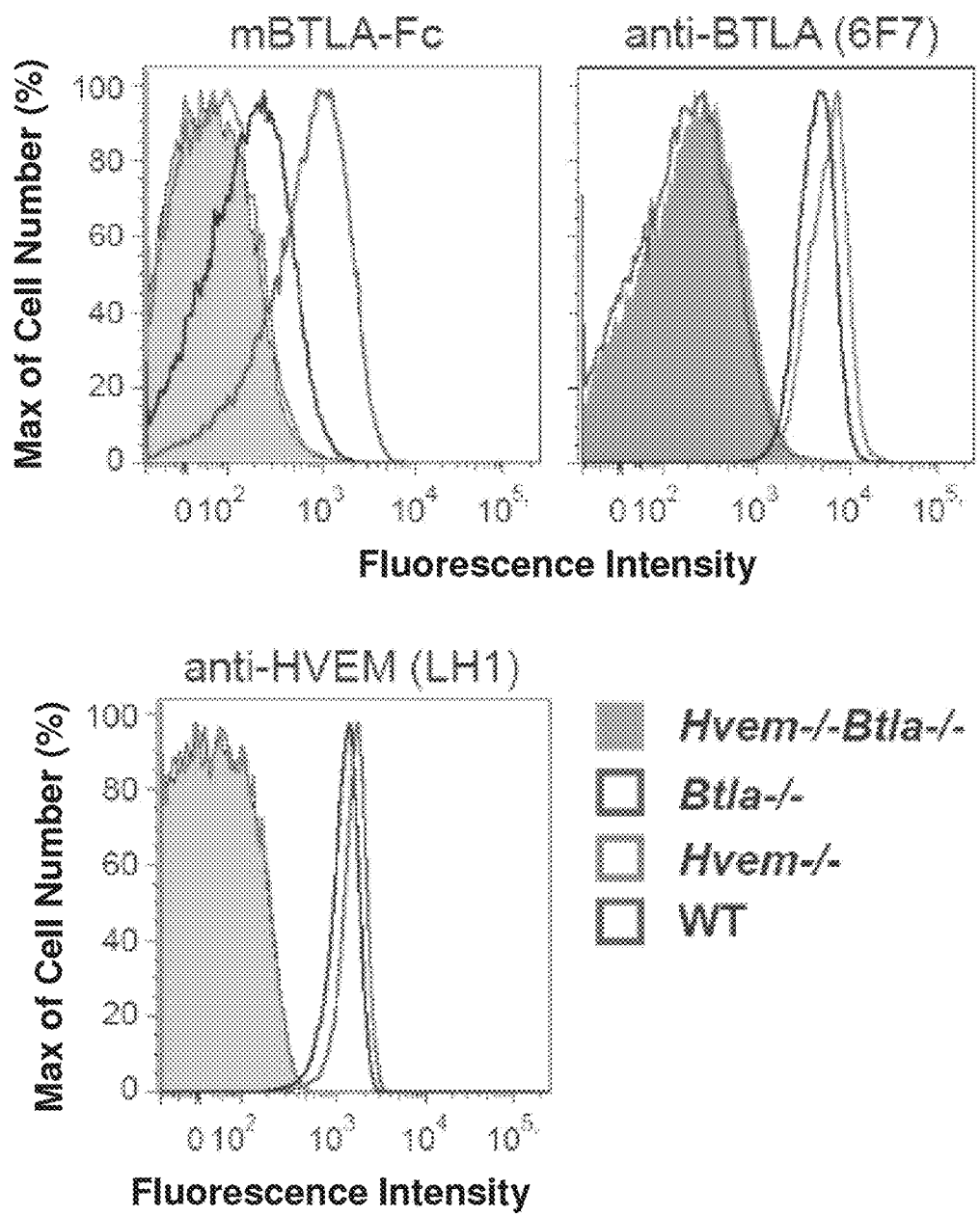

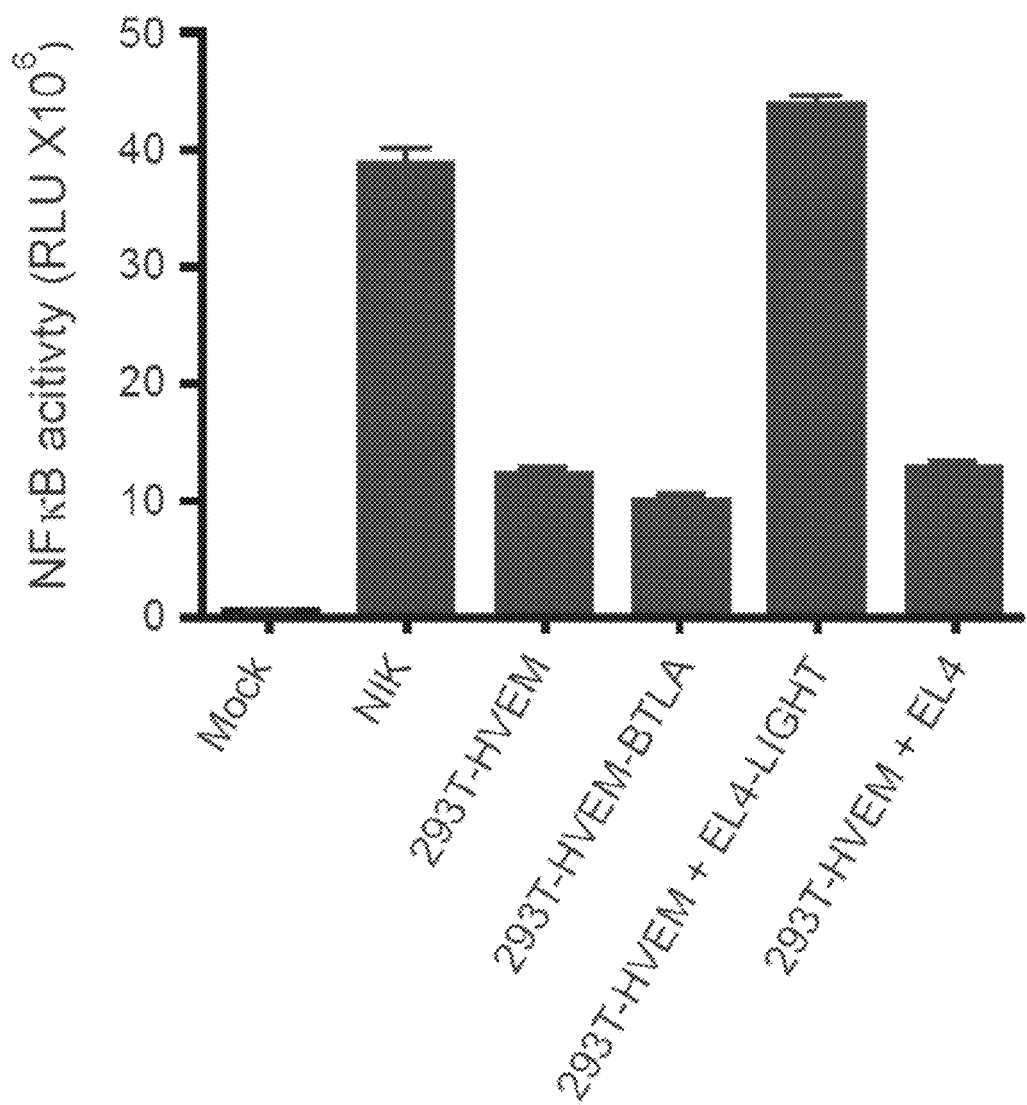

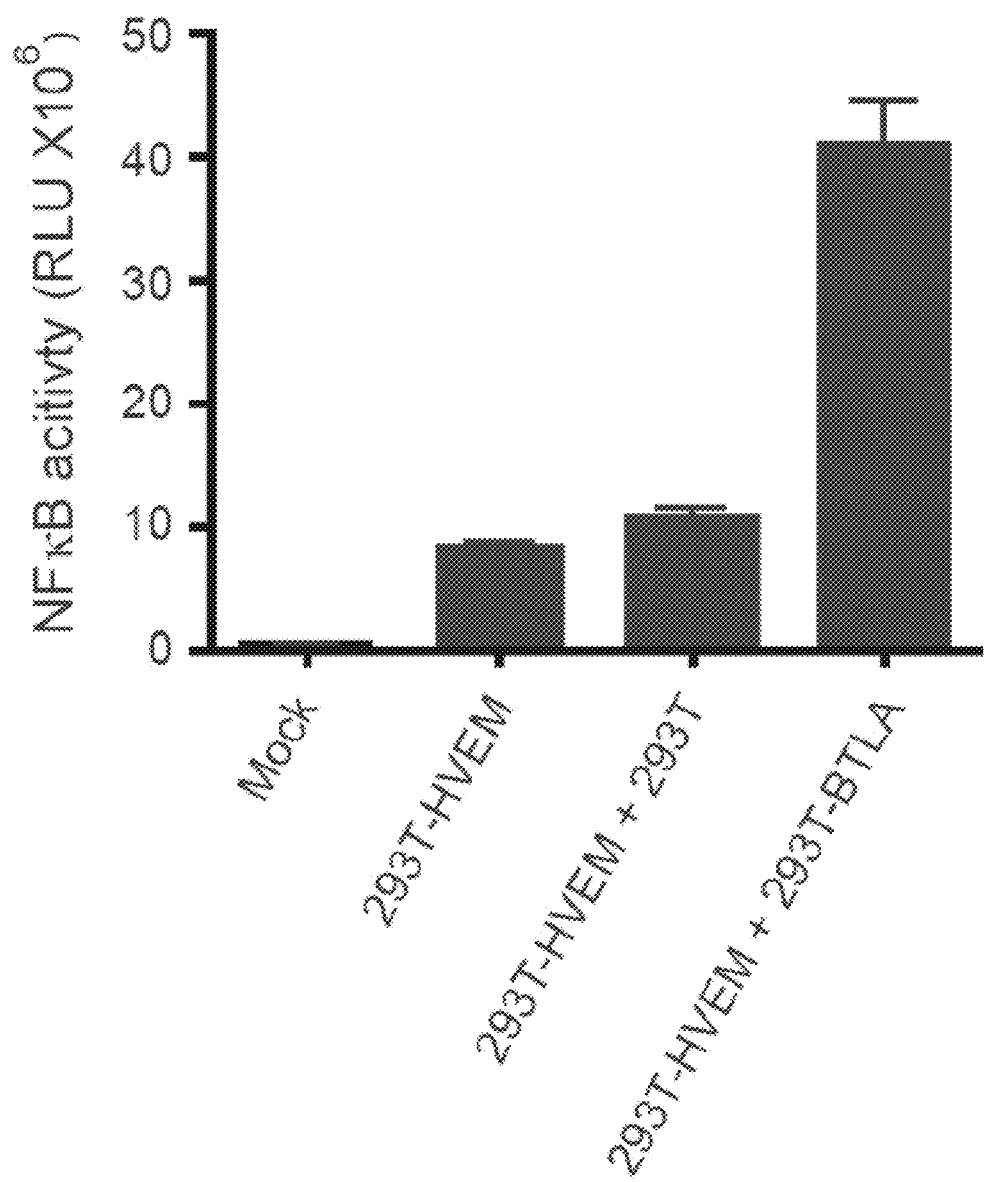

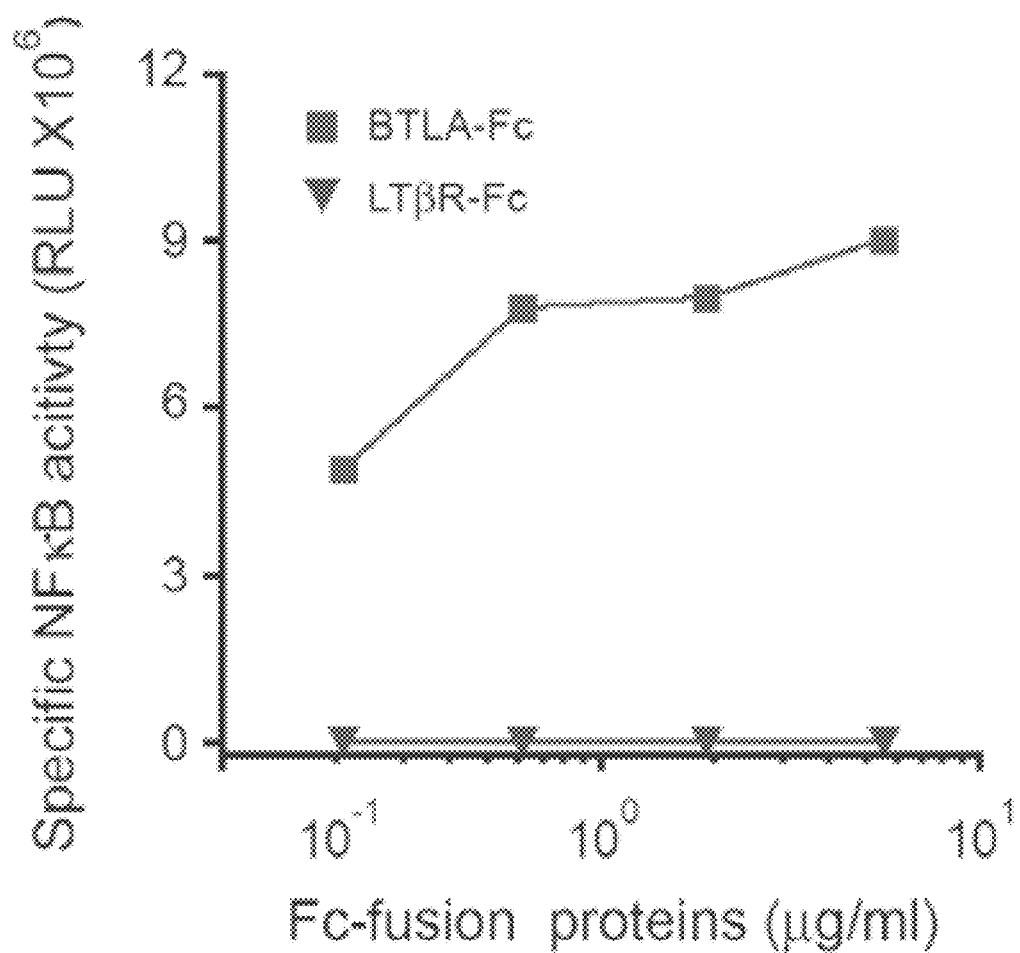

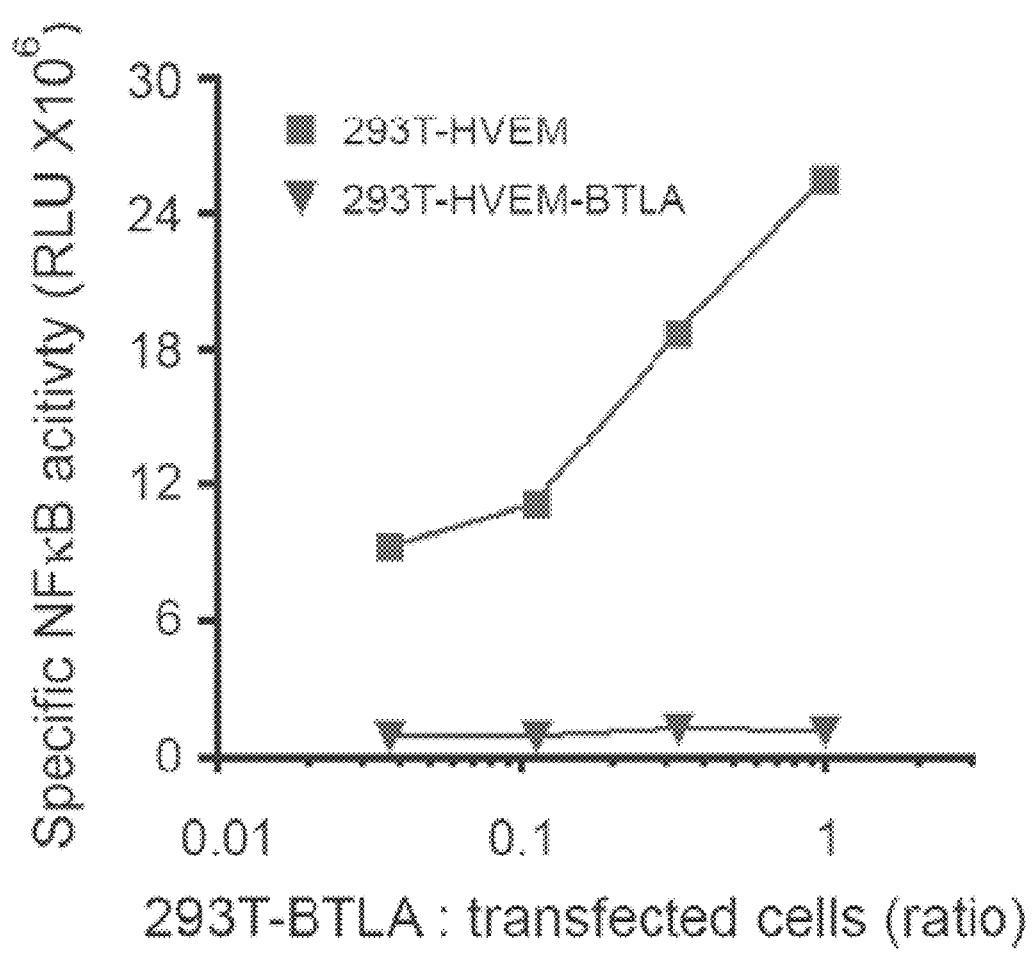

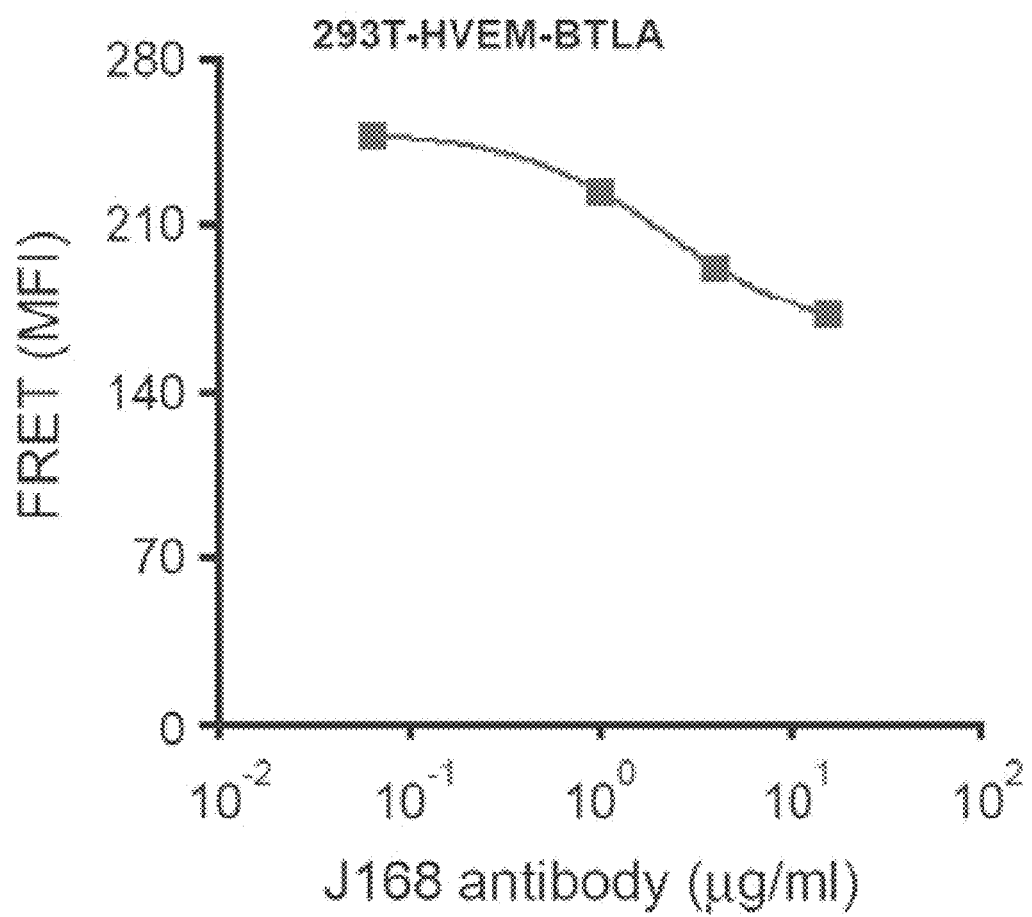

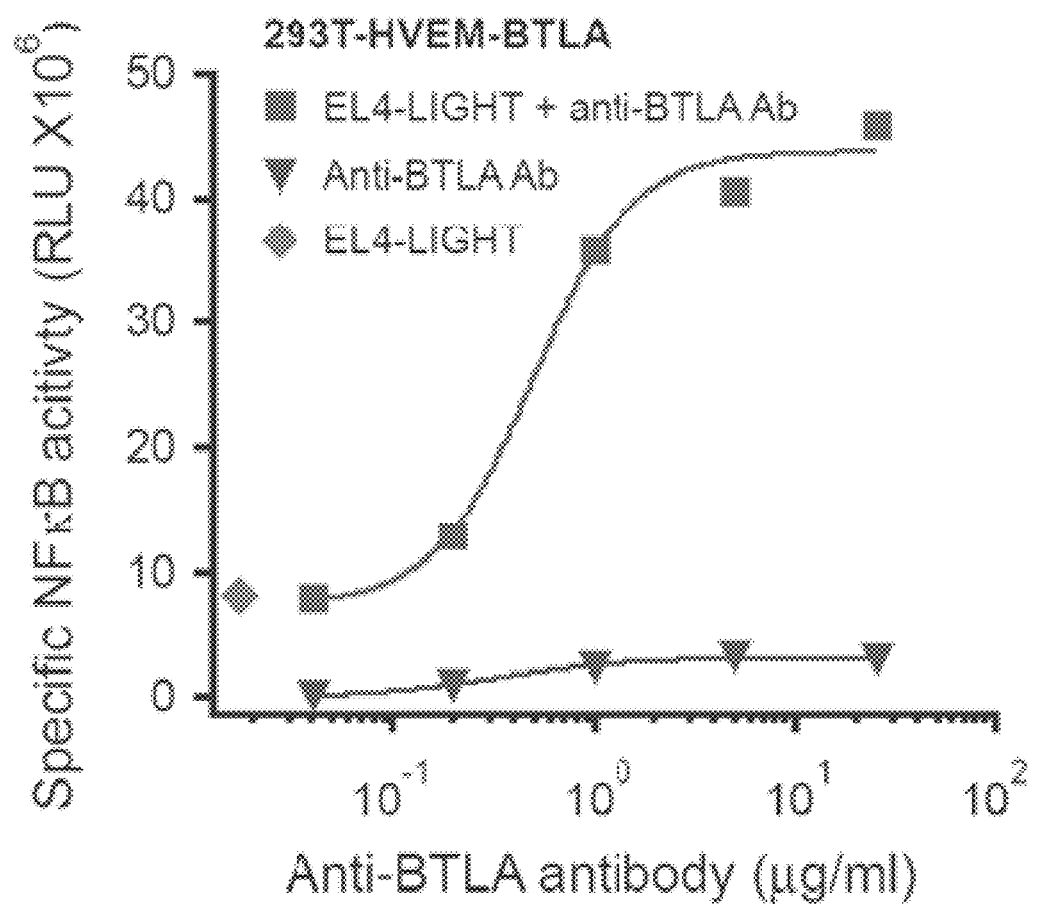

METHODS OF MODULATING HVEM, BTLA AND CD160 CIS COMPLEX RESPONSE OR SIGNALING ACTIVITY WITH SOLUBLE LIGHT POLYPEPTIDE SEQUENCES

RELATED APPLICATIONS

This application is a continuation of application Ser. No. 12/534,658, filed Aug. 3, 2009, which is a continuation-in-part and claims the benefit of priority of PCT international application no. PCT/US2009/49968, filed Jul. 8, 2009, application Ser. No. 61/078,997, filed Jul. 8, 2008, and is a continuation in part of application Ser. No. 11/721,308, completed Jun. 22, 2009, PCT international application no. PCT/US2005/044296, filed Dec. 9, 2005, and which also claims priority to application Ser. No. 60/770,636, filed Jul. 19, 2005, and application Ser. No. 60/635,034, filed Dec. 9, 2004, all of which applications are expressly incorporated herein by reference in their entirety.

GOVERNMENT SUPPORT

This work was supported in part by Grants R37AI33068 and AI067890 from the National Institutes of Health. The government has certain rights in the invention.

TECHNICAL FIELD

The invention relates to HVEM cis complexes. Such HVEM cis complexes include, for example, HVEM/BTLA, HVEM/CD160 and HVEM/gD cis complexes. Furthermore, the invention relates to ligands and agents that bind to HVEM cis complexes, such as antibodies. Also, the invention relates to methods of use of the HVEM cis complexes, and the ligands and agents (e.g., antibodies) that bind to the HVEM cis complexes.

INTRODUCTION

Both TCR and cooperating signaling pathways that activate either stimulatory or inhibitory responses contribute to T cell homeostasis. Manipulation of cosignaling pathways can affect the outcome of some autoimmune diseases, such as rheumatoid arthritis, Crohn's disease and psoriasis, but not other diseases, such as lupus erythematosus. The mechanisms of action of some of these cosignaling pathways are poorly understood and have resulted in unsafe application such as in the case of CD28 targeted therapy (Suntharalingam, G. et al. *N Engl J Med* 355:1018 (2006)). Thus understanding the mechanism of action of cosignaling pathways can be useful in discovery of new or modify existing therapeutics.

Cosignaling pathways initiated by members in the Ig superfamily or the TNF Receptor superfamily can independently initiate either positive or inhibitory signaling pathways. An important intersection between these cosignaling families occurs in the engagement of the TNFR, herpesvirus entry mediator (HVEM, TNFRSF14) (Montgomery, et al., *Cell* 87:427 (1996)) with the Ig superfamily member, B and T lymphocyte attenuator (BTLA) (Sedy, et al., *Nat Immunol* 6:90 (2005), Gonzalez, et al., *Proc Natl Acad Sci USA* 102:1116 (2005)). HVEM binds the TNF-related ligands, LIGHT (homologous to lymphotoxins, exhibits inducible expression, and competes with HSV glycoprotein D for HVEM, a receptor expressed by T lymphocytes, or TNFSF14) and lymphotoxin (LT)-α (Mauri, et al., *Immunity* 8:21 (1998)), and two additional Ig superfamily members, CD160 (Cai, et al., *Nat Immunol* 9:176 (2008)) and the herpes simplex virus envelope glycoprotein D (gD) (Montgomery, et al., *Cell* 87:427 (1996)).

HVEM serves as a molecular switch activating both stimulatory and inhibitory pathways for immune homeostasis. The LIGHT-HVEM system initiates a strong costimulatory signal promoting inflammation and enhancing immune responses (Gommerman, et al., *Nat Rev Immunol* 3:642 (2003), Ware, C. F. *Immunol Rev* 223:186 (2008)), by initiating activation of the prosurvival transcription factor nuclear factor-κB (NF-κB) through a TRAF-dependent serine kinase cascade (Hsu, et al., *J. Biol. Chem.* 272:13471 (1997), Rooney, et al., *J. Biol. Chem.* 275:14307 (2000)). By contrast, HVEM engagement of BTLA and CD160 activates inhibitory signaling in lymphoid cells (Sedy, et al., *Nat Immunol* 6:90 (2005), Cai, et al., *Nat Immunol* 9:176 (2008), Murphy, et al., *Nat Rev Immunol* 6:671 (2006)) through recruitment of SHP1 and SHP2 phosphatases, which attenuate tyrosine kinases activated by TCR antigen recognition (Sedy, et al., *Nat Immunol* 6:90 (2005), Watanabe, et al., *Nat Immunol* 4:670 (2003), Chemnitz, et al., *J Immunol* 176:6603 (2006)). LIGHT engages HVEM at a topographically distinct site from the common site bound by BTLA (Sedy, et al., *Nat Immunol* 6:90 (2005), (Sedy, et al., *Nat Immunol* 6:90 (2005), Gonzalez, et al., *Proc Natl Acad Sci USA* 102:1116 (2005), Carfi, et al., *Molecular Cell* 8:169 (2001), Nelson, et al., *J Immunol* 180:940 (2008), Compaan, et al., *J Biol Chem* 280:39553 (2005), Cheung, et al., *Proc Natl Acad Sci USA* 102:13218 (2005), Watts, et al., *Proc Nati Acad Sci USA* 102:13365 (2005), CD160 (Cai, et al., *Nat Immunol* 9:176 (2008)) and gD (Carfi, et al., *Molecular Cell* 8:169 (2001)). However, membrane LIGHT noncompetitively inhibits HVEM-BTLA interaction suggesting a role for LIGHT as a regulator of HVEM-BTLA inhibitory signaling.

The physiological context of inhibitory signaling initiated through the HVEM-BTLA pathway proceeds in a unidirectional fashion, with HVEM activating inhibitory trans signaling in adjacent cells expressing BTLA. In a model of colitis, trans signaling between HVEM in host intestinal cells and BTLA in T cells prevented accelerated colitis (Steinberg, et al., *J Exp Med* 205:1463 (2008)). However, reports indicate that BTLA can also initiate survival signals for effector T cells (Hurchla, et al., *J Immunol* 178:6073 (2007)). Indeed, Btla$^{-/-}$ T cells reactive to alloantigens in a graft vs host disease setting failed to survive, although the initial response was normal. The colitis model also revealed BTLA as a survival factor based on the findings that Btla$^{-/-}$ T cells transferred into Rae hosts failed to accumulate, with the reduced number of effector T cells in the recipients, ultimately affecting the onset of colitis (Steinberg, et al., *J Exp Med* 205:1463 (2008)). Although the structural features of BTLA raised doubts of whether it could activate HVEM, there is evidence that BTLA, CD160, and gD function as activating ligands for HVEM promoting NF-κB activation and cell survival. Moreover, Btla$^{-/-}$ T cells survived poorly following activation, but a soluble surrogate of BTLA, BTLA-Fc, activated NF-κB and rescued Btla$^{-/-}$ T cells from activation-induced apoptosis. These results indicate the HVEM-BTLA trans complex forms a bidirectional signaling system that may serve as an inhibitory and cell survival system for lymphoid and epithelial cells.

The specific context of ligand receptor engagement dramatically alters signaling by HVEM. HVEM-BTLA limits the proliferation of conventional dendritic cell subsets in the spleen, countering the proliferation signals mediated through LTR (De Trez, et al., *J Immunol* 180:238 (2008), Kabashima, et al., *Immunity* 22:439 (2005)). In the absence of HVEM or BTLA, CD4+ DC showed a dramatic increase in repopulation compared to wild type DC (De Trez, et al., *J Immunol* 180:238 (2008)). Enhanced proliferative DC phenotype required intrinsic expression of HVEM and BTLA, but was partially influenced by HVEM and BTLA in the supporting stroma, suggesting both cis and trans acting effects between HVEM and BTLA in limiting DC proliferation.

SUMMARY

As disclosed herein, BTLA and HVEM form a "cis" complex, and CD160 and HVEM form a "cis" complex. HVEM cis complex formation with BTLA limits the activation HVEM by its cellular ligands. Naïve T cells (e.g., human and mouse) express a stable heterodimeric "cis" complex of HVEM and BTLA that uses the same binding interaction as the trans complex. This HVEM-BTLA "cis" complex competitively inhibits trans signaling by all cellular ligands of HVEM, which can provide, among other things, a mechanism to maintain T cells in a resting state. Thus, the context of HVEM expression (cis or trans) with its various ligands determines signaling outcome: bidirectional signaling of HVEM in a trans complex can provide survival signaling for activated T cells, and HVEM in cis interactions in naïve T cells limits receptivity to signals from cells, such as those in the surrounding microenvironment.

As also disclosed herein, the conformation of HVEM in cis or trans with its Ig superfamily ligands (BTLA, CD160, LIGHT, gD, etc.) changes the signaling activity of HVEM, which determines receptivity to cellular or other signals. The data disclosed herein reveal a signaling paradigm, the HVEM-BTLA cis complex—a cell autonomous heterodimer that inhibits signaling from adjacent cells. In cis conformation, BTLA not only inhibits trans activation of HVEM by its cellular ligands, but also inhibits or prevents spontaneous multimerization of HVEM, (consistent with the finding that the cis conformation prevented recruitment of TRAF2, an early biochemical step in HVEM signal activation). HSV ligand gD co-expressed with HVEM constitutively activated NF-κB, yet blocked trans signaling by the other ligands. The inhibitory function of HVEM cis complexes is likely important for naïve T cells to limit trans signaling by LIGHT, BTLA and CD160, expressed in adjacent activated cells, which could be establish peripheral tolerance.

In accordance with the invention, there are provided isolated and/or purified cis complexes, including, for example, herpes virus entry mediator (HVEM) polypeptide binding to B-and T-lymphocyte attenuator (BTLA) polypeptide cis complex, and herpes virus entry mediator (HVEM) polypeptide binding to CD160 polypeptide cis complex. Cis complexes can be biochemically, structurally, functionally or immunochemically distinct from trans complexes. In various embodiments, a HVEM/BTLA cis complex does not substantially bind to a soluble HVEM polypeptide or a soluble BTLA polypeptide, or does not substantially bind to an HVEM polypeptide or a BTLA polypeptide to form a trans complex. In various embodiments, a HVEM/CD160 cis complex does not substantially bind to soluble HVEM, soluble CD160, soluble BTLA or soluble gD to form a trans complex.

In further various embodiments, a BTLA/HVEM cis complex inhibits, reduces, decreases, attenuates, suppresses, prevents or blocks activation of the HVEM polypeptide, or inhibits, reduces, decreases, attenuates, suppresses, prevents or blocks binding of the HVEM polypeptide in the cis complex to one or more of CD160, or glycoprotein D (gD) of herpes simplex virus polypeptides, in trans; a BTLA/HVEM cis complex is not disrupted by soluble LIGHT binding to the HVEM polypeptide in the cis complex; the HVEM polypeptide binding to the BTLA polypeptide in a cis complex is enhanced by soluble LIGHT or LTα binding to the HVEM polypeptide in the cis complex; or a BTLA/HVEM cis complex inhibits, reduces, decreases, attenuates, suppresses, prevents or blocks signaling induced by the HVEM polypeptide binding in the cis complex to one or more of LIGHT, BTLA, gD, or LTα. In additional various embodiments, the HVEM polypeptide binding to the BTLA polypeptide in a cis complex enhances or stimulates activation of the BTLA polypeptide; binding of the HVEM polypeptide to the BTLA polypeptide in a cis complex is greater or more stable than binding of an HVEM polypeptide to a BTLA polypeptide in a trans complex; HVEM polypeptide binding to BTLA polypeptide in said cis complex is disrupted by contact with membrane LIGHT; or HSV gD does not appreciably bind to HVEM polypeptide in the cis complex.

In further various embodiments, a CD160/HVEM cis complex inhibits, reduces, decreases, attenuates, suppresses, prevents or blocks binding of HVEM to one or more of BTLA, LIGHT, glycoprotein D (gD) of herpes simplex virus, or LTα (lymphotoxin-α) in trans; a CD160/HVEM cis complex is not disrupted by soluble LIGHT binding or LTα binding to the HVEM polypeptide in the cis complex; or a CD160/HVEM cis complex inhibits, reduces, decreases, attenuates, suppresses, prevents or blocks signaling induced by binding of the HVEM polypeptide in the cis complex to one or more of LIGHT, BTLA, CD160, gD, or LTα in trans. In additional various embodiments, binding of the HVEM polypeptide to the CD160 polypeptide in a cis complex is greater or more stable than binding of an HVEM polypeptide to a CD160 polypeptide in a trans complex; or HSV gD does not appreciably bind to HVEM polypeptide in the cis complex.

The invention also provides antibodies (monoclonal, polyclonal, human, non-human, humanized, etc.) that bind to a cis complex. In one embodiment, an antibody binds to HVEM/BTLA cis complex. In another embodiment, an antibody binds to HVEM/CD160 cis complex. Antibodies include those having a binding affinity for binding to a cis complex that is greater than binding affinity for the antibody for binding to a corresponding trans complex. Antibodies also include those having a binding affinity for binding to a cis complex that do not detectably bind to membrane bound HVEM, BTLA, or CD160, or a corresponding trans complex (e.g., HVEM bound BTLA, HVEM bound CD160, or HVEM bound HSV gD). Antibodies further include those having a agonist or antagonist activity or function, such as HVEM, BTLA, CD160 or LIGHT binding, signaling or activity. Antibodies moreover include those that inhibit, reduce, decrease, attenuate, suppress, prevent or block, or induce, stimulate, enhance or increase an activity, function or expression of HVEM, BTLA or CD160; and those that modulate a response mediated or associated with HVEM, BTLA or CD160 activity or expression (e.g., lymphocyte or hematopoetic cell proliferation or inflammation; proliferation, survival, differentiation, death, or activity of T cells, antigen presenting cells or B cells).

The invention further provides compositions including pharmaceutical formulations. Invention compositions include, for example, cis complexes and antibodies that bind to cis complexes.

The invention moreover provides methods of modulating a HVEM, BTLA or CD160 response or signaling activity, in vitro, in vivo or ex vivo. In various embodiments, a method includes contacting a HVEM/BTLA cis complex, or a HVEM/CD160 cis complex with a soluble LIGHT polypeptide sequence that binds to the cis complex, thereby modulating a HVEM, BTLA or CD160 response or signaling activity.

The invention additionally provides methods of treatment of an undesirable or aberrant immune response, immune disorder or an immune disease, such as an undesirable or aberrant acute or chronic inflammatory response or inflammation, or autoimmune disease. In various embodiments, a method includes administering to a subject a ligand that binds to a HVEM/BTLA cis complex, or binds to a HVEM/CD160 cis complex, in a sufficient amount for treatment of the undesirable or aberrant immune response, immune disorder or an immune disease.

The invention still further provides methods for screening for the presence of a cis complex. In one embodiment, a method includes analyzing a sample (e.g., a biological sample) for the presence of a cis complex (e.g., HVEM/BTLA or HVEM/CD160 cis complex), for example, by contacting a sample with an antibody that binds to a cis complex (e.g., HVEM/BTLA or HVEM/CD160 cis complex), and determining whether the antibody binds to the cis complex.

The invention still additionally provides in vitro, in vivo and ex vivo methods of inhibiting, reducing, decreasing, attenuating, preventing or blocking proliferation, survival, differentiation, death, activity or signaling of T cells, antigen presenting cells or B cells. In various methods embodiments, cells are contacted with a soluble LIGHT polypeptide sequence that binds to a cis complex in an amount sufficient to inhibit, reduce, decrease, attenuate, prevent or block proliferation, survival, differentiation, death, or activity of T cells, antigen presenting cells or B cells. In particular aspects, the contacting is in a subject in need of inhibiting, reducing, decreasing, attenuating, preventing or blocking proliferation, survival, differentiation, death, or activity of T cells, antigen presenting cells or B cells.

The invention yet further provides methods of inhibiting, reducing, decreasing, attenuating, preventing or blocking acute or chronic inflammation, methods of treating an undesirable or aberrant immune response, immune disorder or immune disease, and methods of inhibiting, reducing, decreasing, attenuating, preventing or blocking an immune response or inflammatory response. In various embodiments, a method includes administering to a subject an amount of a soluble LIGHT polypeptide sequence that binds to a cis complex comprising herpes virus entry mediator (HVEM) polypeptide binding to B- and T-lymphocyte attenuator (BTLA) polypeptide, sufficient to inhibit, reduce, decrease, attenuate, prevent or block an immune response or inflammatory response.

The invention yet additionally provides methods of treating neoplasias, tumors, and cancers. In one embodiment, a method includes administering to a subject an amount of an agent that inhibits, reduces, decreases, attenuates, prevents, blocks formation, or disrupts a cis complex (e.g., HVEM/BTLA or HVEM/CD160), sufficient to treat the neoplasia, tumor, or cancer.

Methods of stimulating, enhancing or increasing survival of a cell that express HVEM, but express less BTLA (relative to HVEM) or no BTLA are yet moreover provided. In one embodiment, a method includes contacting the cell with an activator of HVEM, thereby stimulating, enhancing or increasing survival of the cell. Such cell(s) include epithelial cells (e.g., an intestinal epithelial cell).

DESCRIPTION OF THE DRAWINGS

FIG. 1A to FIG. 1E show Cis-interaction between HVEM and BTLA. (A) Co-immunoprecipitation of HVEM and BTLA. 293T cells were transfected with HVEM (Flag tagged) and BTLA, or individually with expression plasmids. HVEM was isolated by immunoprecipitation using anti-Flag mAb (M2) and Western blotted to visualize BTLA with anti-human BTLA mAb (J168) (upper panel) and HVEM with biotinylated mouse anti-human HVEM (lower panel). 293T cells individually transfected with HVEM or BTLA were mixed at 1:1 ratio, centrifuged to establish contact, incubated for 30 min and subjected to immunoprecipitation as above. (B) Schema of the FRET system using HVEM-CFP (donor fluorophore) and BTLA-DsRed (acceptor fluorophore) to detect HVEM-BTLA cis interaction. 293T cells were transfected individually or cotransfected with these fluorophores. Fluorescence was detected at the FRET channel with the detection window at 564-606 nm using a BD LSRII flow cytometry system. (C) Subcellular localization of HVEM-CFP and BTLA-DsRed detected by confocal microscopy. HVEM-CFP and BTLA-DsRed expressing 293T cells were visualized using an Kr—Ar laser with the laser line set at 488 nm, and the fluorescence is colored in cyan for CFP and in red for DsRed. Cells expressing CFP or DsRed 293T cells were used as controls (lower panel). (D) Assessment of the cis-association of HVEM and BTLA by FRET assay. HVEM-CFP and BTLA-DsRed coexpressing cells, HVEM-CFP cells, and BTLA-DsRed cells were detected at the CFP channel (excitation at 405 nm, emission at 425-475 nm), DsRed channel (excitation at 488 nm, emission at 562-588 nm), and FRET channel (excitation at 405 nm, emission at 564-606 nm). HVEM-CFP and BTLA-DsRed coexpressing cells (blue), HVEM-CFP cells (cyan) and BTLA-DsRed cells (red). Note that at similar levels of CFP and DsRed expression with reference to the HVEM-CFP and BTLA-DsRed coexpressing cells (left upper panel), there was minimal CFP spectral overlap and DsRed coexcitation detected in the FRET channel (left lower panel). The right panel (D) shows an overlay of the FRET channel. (E) Endogenous BTLA-HVEM complex was isolated from mouse T cell hybridoma by immunoprecipitation using mouse anti-mBTLA mAb (6F7 clone) and Western blotted to visualize HVEM with goat anti-mHVEM Ab.

FIG. 2A to FIG. 2E show that HVEM-BTLA cis complex inhibits trans interactions. (A) (Left panel) BTLA expressing 293T cells (293T-BTLA) or BTLA and HVEM coexpressing 293T cells (293T-BTLA-HVEM) were prepared by transfection. 293T-BTLA and 293T-BTLA-HVEM were stained with rat anti-BTLA monoclonal antibody (5 µg/ml; 6F4) or goat anti-HVEM antibody (25 µg/ml). Mock transfected 293T cells were used as negative controls (filled histogram). (Right panel) Saturation binding assay for HVEM-Fc binding to 293T-BTLA or 293T-BTLA-HVEM. Graded concentrations of HVEM-Fc were added to the cells in binding buffer (PBS with 2% FBS) for 45 min, washed and stained with RPE conjugated goat anti-human IgG Feγ. (B) BTLA binding site on HVEM in cis and trans. (Upper panel) Flow cytometric staining of 293T-HVEM, 293T-HVEM-Y61F and 293T-HVEM-Y61A with goat anti-HVEM antibody (10 µg/ml) (unfilled histogram) or mock transfected 293T cells (filled) or (lower panel) BTLA-Fc (25 µg/ml) to the HVEM mutants. (C) Competition of cis- and trans-interaction between wild type HVEM, HVEM-Y61A, and BTLA. BTLA and HVEM-Y61A mutant were cotransfected into 293T cells (293T-BTLA-HVEM-Y61A). (Left panel) Flow cytometric staining of 293T-BTLA-HVEM cells with rat anti-BTLA monoclonal antibody (6F4 clone, 5 µg/ml, unfilled histogram) or goat anti-HVEM antibody (10 µg/ml, unfilled histogram) or mock transfected 293T cells (filled histogram). (Right panel) Saturation binding analysis for HVEM-Fc binding to 293T-BTLA-HVEM-Y61A. Graded concentrations HVEM-Fc were added to the cells in binding buffer, and the saturation binding assay was carried as in (A). (D) Competition of cis- and trans-interaction between wild type HVEM, HVEM-Y61F and BTLA. BTLA and HVEM-Y61F mutant were cotransfected into 293T cells (293T-BTLA-HVEM-Y61F). Cell surface staining for BTLA and HVEM was performed as in (C, left panel). Saturation binding assay for HVEM-Fc binding to 293T-BTLA-HVEM-Y61F was carried out as in (C, right panel). (E) Staining of purified mouse T cells with mBTLA-Fc or anti-BTLA (6F7) and anti-HVEM (LH1) antibodies. Splenic T cells isolated from Hvem$^{-/-}$Btla$^{-/-}$ (filled histogram), Btla$^{-/-}$, Hvem$^{-/-}$ and wild type mice were stained and analyzed by flow cytometry.

FIG. 3A to FIG. 3D show that HVEM-BTLA cis complex inhibits LIGHT-mediated HVEM signaling. (A) Schematic illustration of soluble LIGHT (LIGHTt66) binding to HVEM-BTLA cis-association complex (left panel). Binding of LIGHTt66 to HVEM and BTLA coexpressing 293T cells (right panel). 293T cells stably expressing HVEM (293T-HVEM), and 293T cells stably coexpressing HVEM and BTLA (293T-HVEM-BTLA) with equivalent HVEM expression were incubated with soluble Flag tagged LIGHTt66 (10 µg/ml) and detected with anti-FLAG antibody. Untransfected 293T cells were used as a negative control. (B) The HVEM-BTLA cis-interaction alters HVEM signaling. NF-κB dependent luciferase reporter vector was transfected into 293T-HVEM and 293T-HVEM-BTLA coexpressing cells. LIGHT expressing EL4 cells (EL4-LIGHT) were cocultured with 239T-HVEM cells for 24 hrs and then assessed for luciferase activity in cell lysates. (C) Dose response of EL4-LIGHT cells or soluble LIGHTt66 were incubated at the indicated ratio or concentration with 293T-HVEM (left panel) or 293T-HVEM-BTLA cells (right panel) and HVEM signaling was assessed using luciferase reporter assay as in (B). (D) Soluble LIGHT inhibited the activation HVEM when added to cultures with EL4-LIGHT cells (right panel) suggesting soluble LIGHT functions as a competitive inhibitor of membrane LIGHT in cells coexpressing HVEM and BTLA, as shown in the schematic representation (left panel).

FIG. 4A to FIG. 4J show inhibition of NF-κB activation by HVEM through BTLA and CD160 cis complexes and activation by herpesvirus gD. (A) 293T-BTLA cells mixed with 293T-HVEM cells expressing the NF-κB reporter (trans configuration) induced a specific, dose-dependent activation of NF-κB Luciferase expression. (B) The HVEM-Y61A mutant, which does not bind BTLA, failed to activate NF-κB when membrane BTLA was expressed in trans (FIG. 4B, left panel). Membrane LIGHT induced dose-dependent luciferase activity in HVEM-Y61A cells (right panel) demonstrating this mutation specifically impacts BTLA-dependent activation of NF-κB. (C) Mouse anti-human BTLA mAb (J168 clone) was incubated with HVEM-Fc and binding assessed on fibroblasts by flow cytometry. Mouse anti-human BTLA mAb (J168) blocked binding of HVEM-Fc to BTLA (left panel) and inhibited HVEM dependent NF-κB signaling induced by 293T-BTLA cells, confirming the specificity of BTLA-mediated HVEM signaling (right panel). (D) Soluble BTLA-Fc induced NF-κB dependent luciferase activity in 293T-HVEM cells mimicking cell expressed BTLA BTLA-Fc activated HVEM signaling in a dose dependent manner while LTβR-Fc failed to activate NF-κB activation. (E) BTLA-Fc-mediated HVEM signaling was enhanced when anti-Fc antibody was added to oligomerize BTLA-Fc bound to HVEM. (F) CD160 stably expressed in EL4 cells when mixed in trans with HVEM expressing 293T cells specifically activated NF-κB luciferase reporter, similarly to BTLA. (G) HVEM-Fc containing Y61A mutation failed to bind CD160 expressed on EL4 cells. (H) The Y61A mutation in HVEM failed to activate in the presence of EL4-CD160 cells. (I) Trans signaling by either HVEM or LTβR specific antibodies revealed in Western blots that HVEM ligation in HT29 cells activated the RelA form of NF-κB, whereas LTβR was competent in activating both RelA and RelB forms of NF-κB, and inducing p100 processing. (J) Visualized by immunohistochemistry, ligation of HVEM in HT29 cells with BTLA-Fc, but not LTβR-Fc, induced nuclear RelA translocation, as did EL4-CD160 expressing EL4 cells, but not by control cells.

FIG. 5A to FIG. 5D show that effector T cell survival requires HVEM and BTLA. (A) Cells that coexpressed HVEM and BTLA failed to recruit TRAF2 to HVEM suggesting HVEM-BTLA cis configuration limits NF-κB activation at the initial activation step in HVEM signaling. (B) HVEM-BTLA cis-interaction inhibits CD160-mediated HVEM signaling. EL4-CD160 cells were cocultured with 293T-HVEM, 293T-HVEM-CD160, or 293T-HVEM-BTLA cells that were transfected with NF-κB reporter plasmid. Luciferase activities were measured after 24 hours. (C) Recruitment of TRAF molecules to HVEM in the context of BTLA-mediated HVEM signaling. 293T-LTβR, 293T-HVEM-Flag, 293T-BTLA, and 293T-HVEM-BTLA cells (cis) were lysed and immunoprecipitated with anti-Flag (M2) or with anti-LTβR and Western blotted for TRAF2 and TRAF3 (lane 3). 293T-HVEM and 293T-BTLA cells were cocultured at 1:1 ratio and incubated for 30 minutes prior to lysis (lane 6). (D) Inhibition of HVEM trans activation by HVEM-BTLAΔcyto cis complex. NF-κB dependent luciferase reporter was transfected into 293T-HVEM, 293T-HVEM-BTLA, and 293T-HVEM-BTLAΔcyto coexpressing cells. BTLA-Fc (5 µg/ml) and anti-Fcγ antibody (1:1 ratio) were incubated with the transfected cells for 24 hrs and then assessed for luciferase activity in cell lysates.

FIG. 6A to FIG. 6H show differential effects of membrane and soluble LIGHT on HVEM/BTLA cis complex. (A) Soluble LIGHT increased membrane BTLA activation of HVEM-dependent NF-κB activation. (B) Disruption of HVEM-BTLA cis-interaction with antagonist anti-BTLA mAb (J168). (C) The HVEM-BTLA cis complex attenuated the signaling capability of LIGHT. (D) EL4-LIGHT cells strongly inhibited growth of the parental EL4 cells. (E) Soluble LIGHT expressing EL4 (EL4-LIGHTt66) cells were unable to stimulate an immune response that prevented tumor growth. (F) and (G) Both EL4-LIGHT and EL4-LIGHTt66 cells acquired the ability to stimulate tumor rejection in BTLA−/− mice, in contrast to wild type B6 mice. (H) Soluble LIGHT can enhance attenuation of immune responses mediated by membrane LIGHT when HVEM associates with BTLA in cis.

DETAILED DESCRIPTION

Figure 1B:
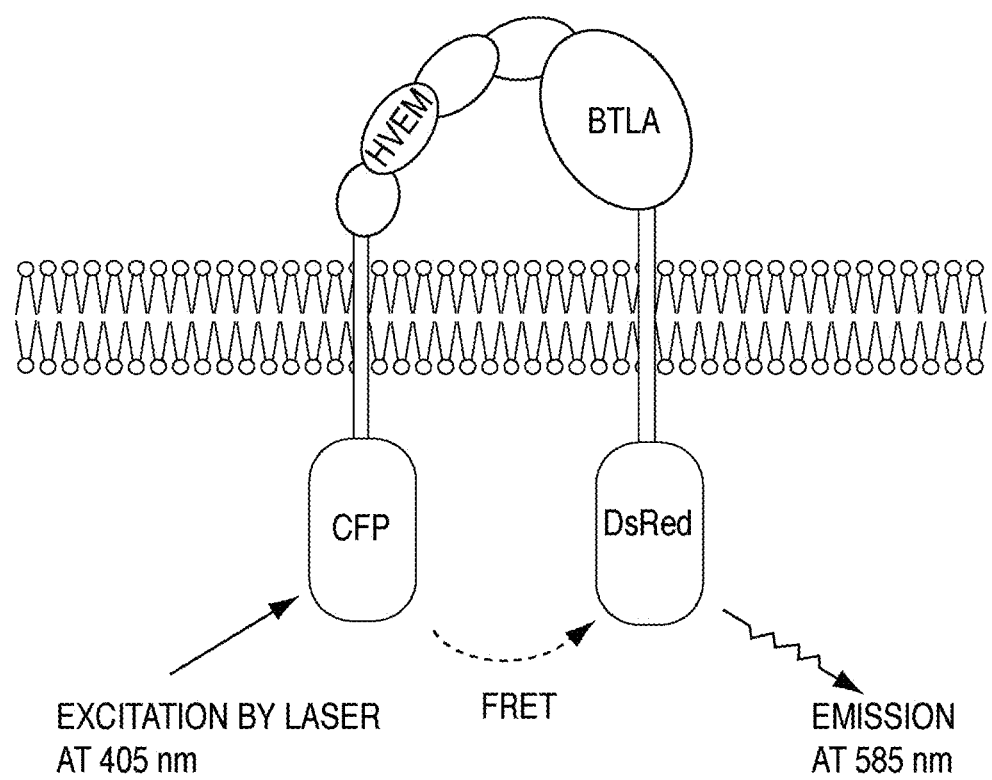

The invention provides, among other things, cis complexes, including isolated or purified cis complexes, as well as compositions that include cis complexes (e.g., compositions including not isolated or not purified cis complexes, as well as compositions including isolated or purified cis complexes). Invention cis complexes are distinct from trans complexes. In one embodiment, a cis complex includes a herpes virus entry mediator (HVEM) polypeptide binding to B- and T-lymphocyte attenuator (BTLA) polypeptide, wherein the cis complex does not substantially bind to a soluble HVEM polypeptide or a soluble BTLA polypeptide, or does not substantially bind to an HVEM polypeptide or a BTLA polypeptide to form a trans complex. In another embodiment, a cis complex includes a herpes virus entry mediator (HVEM) polypeptide binding to a CD160 polypeptide, wherein the cis complex does not substantially bind to a soluble HVEM polypeptide, a soluble CD160 polypeptide, a soluble HSV gD polypeptide, or a soluble BTLA polypeptide to form a trans complex.

As used herein, the term "cis" when used in reference to a complex, configuration, interaction of two or more entities (e.g., HVEM, BTLA, CD160, HSV gD polypeptide sequences), means that the two or entities bind to each other as when they are expressed in the same cell (e.g., cell membrane or lipid bilayer). Thus, in a cis complex or configuration, the entities interact (bind) to form a complex such as that which occurs when each entity is expressed in the same cell. A cis interaction need not result from expression within a cell, but may occur through attachment or insertion of both cis-interacting entities into the same lipid bilayer, such as in a liposome. Thus, although exemplary cis complexes (e.g., HVEM/BTLA, HVEM/CD160 and HVEM/gD) were identified by virtue of expression in the same cell, such cis complexes can be free of a cell membrane, as they form a stable, energy favorable interaction.

As used herein, the term "trans" when used in reference to a complex, configuration or interaction of two or more entities (e.g., HVEM, BTLA, CD160, HSV gD polypeptide sequences), means that the two or entities bind as when they are not expressed in the same cell, such as the same cell membrane, but instead are each expressed in different cells, such as in two different membranes of two different cells. For example, a first entity is expressed in a first cell, and a second entity is expressed in a second cell, and the trans interaction formed is between the two entities on the two different cell membranes. Alternatively, one entity is expressed in a first cell, and the second entity is expressed in a soluble or free form, and the trans interaction formed is between the first entity in the first cells, and a second entity that is in a soluble or free form, but is outside the cell. Thus, in a trans complex or configuration, the entities are expressed in different bilayers (cell membranes) and form a complex such as that which would occur when each entity is expressed in a different cell or membrane (e.g., lipid bilayer), or one entity is expressed in a cell, and a second entity is expressed in a soluble or free form (not a lipid bylayer, such as in a cell).

The cis complex, configuration, interaction or binding need not maintain the presence of a bilayer or membrane (cell) in order to maintain the cis structure. Thus, a cis complex can be separated (e.g., isolated or purified) from all or a part of the lipid bilayer or membrane in which the cis complex forms without destroying the cis complex. Thus, once a cis complex forms, at least one or more of the structural, biochemical, immunochemical, physical and functional features or attributes of the cis complex distinct from the trans complex is maintained without the presence of all or a part of the membrane in which the cis complex formed. Accordingly, a cis complex does not require a bilayer or membrane (cell) in order for the cis complex to be stable.

There are structural, biochemical, immunochemical and physical features of cis complexes. One or more non-limiting examples include one or more of the components of the cis complex not substantially binding to a soluble HVEM polypeptide, soluble CD160 or a soluble BTLA polypeptide to form a trans complex. Other non-limiting examples include that a cis complex (e.g., HVEM/BTLA or HVEM/CD160) is not disrupted by soluble LIGHT or LTα (lymphotoxin-α) binding to the HVEM polypeptide in the cis complex; the HVEM polypeptide binding to the BTLA polypeptide or the HVEM polypeptide binding to the CD160 polypeptide in the cis complex is enhanced by soluble LIGHT or LTα binding to the HVEM polypeptide in the cis complex. Additional non-limiting examples are that a cis complex inhibits, reduces, decreases, attenuates, suppresses, prevents or blocks binding of HVEM to one or more of BTLA, LIGHT, glycoprotein D (gD) of herpes simplex virus, or LTα (lymphotoxin-α) in trans. A further non-limiting example is that a hamster anti-mouse BTLA antibody denoted 6A6 does not specifically bind to the mouse BTLA polypeptide in the cis complex. Another non-limiting example is that anti-human BTLA antibody J168 has reduced ability to specifically bind to the human BTLA polypeptide in the cis complex, as compared to binding of the antibody to a BTLA polypeptide bound to an HVEM polypeptide in a trans complex. Still another non-limiting example is that HSV gD does not appreciably bind to HVEM polypeptide in a cis complex.

There are also functional features of cis complexes. One or more non-limiting examples include that the BTLA polypeptide binding to the HVEM polypeptide or CD160 polypeptide binding to the HVEM polypeptide in a cis complex inhibits, reduces, decreases, attenuates, suppresses, prevents or blocks activation of the HVEM polypeptide. Other non-limiting examples include that the HVEM polypeptide binding to the BTLA polypeptide or CD160 polypeptide binding to the HVEM polypeptide in the cis complex enhances or stimulates activation of the BTLA polypeptide (as an agonist of BTLA suppressive function), or that formation of the cis complex in activated T cells inhibits, reduces, decreases, attenuates, suppresses, prevents or blocks infection of said T cells by a Herpes Simplex Virus (HSV). Additional non-limiting examples include that the cis complex inhibits, reduces, decreases, attenuates, suppresses, prevents or blocks signaling induced by binding of the HVEM polypeptide in the cis complex to one or more of LIGHT, BTLA, CD160, gD, or LTα in trans. Further non-limiting examples include that the cis complex inhibits, reduces, decreases, attenuates, suppresses, prevents or blocks binding of the HVEM polypeptide in the cis complex to one or more of CD160, or glycoprotein D (gD) of herpes simplex virus polypeptides, in trans. Non-limiting particular examples of signaling include NF-κB signaling, such as signaling induced by soluble LIGHT, membrane bound LIGHT, soluble BTLA, membrane bound BTLA, soluble CD160, membrane bound CD160, soluble gD, or membrane bound gD binding to the HVEM polypeptide, TRAF recruitment to HVEM. (e.g., TRAF2 recruitment), etc. In particular, for example, a cis complex inhibits, reduces, decreases, attenuates, suppresses, prevents or blocks signaling (e.g., NF-κB signaling) induced by the HVEM polypeptide binding in the cis complex to one or more of LIGHT, BTLA, gD, or LTα. NF-κB signaling includes, for example, signaling induced by soluble LIGHT, membrane bound LIGHT, soluble BTLA, membrane bound BTLA, soluble CD160, membrane bound CD160, soluble gD, or membrane bound gD binding to the HVEM polypeptide.

Invention cis complexes include cis complexes with one or more structural, biochemical, immunochemical, physical or functional features or attributes that distinguish a cis complex from a trans complex. One non-limiting example is that binding of the HVEM polypeptide to the BTLA polypeptide in a cis complex is greater or more stable than binding of an HVEM polypeptide to a BTLA polypeptide in a trans complex. Another non-limiting example is that binding of the HVEM polypeptide to the CD160 polypeptide in a cis complex is greater or more stable than binding of an HVEM polypeptide to a CD160 polypeptide in a trans complex. Relative binding affinity or strength, for example to determine the relative binding affinity or strength of cis compared to trans complexes, can be determined by a competition binding assay. For example, HVEM polypeptide expressed in the same cells as BTLA (e.g., 293 T cells) can inhibit or block trans interaction between the membrane BTLA and a soluble HVEM (e.g., HVEM-Fc).

Further, invention cis complexes include cis complexes with one or more structural, biochemical, immunochemical, physical or functional features or attributes in common with a cis complex from a trans complex. For example, both HVEM/BTLA and HVEM/CD160 cis and trans complexes are mediated, at least in part, by cysteine rich domain 1 (CRD1) of the HVEM polypeptide sequence. Biochemical features in common include binding to ligands. In another example, soluble LIGHT bind to both HVEM/BTLA and HVEM/CD160 cis and trans complexes. In yet another example, HVEM polypeptide binding to BTLA polypeptide in a cis or trans complex is disrupted by contact with membrane bound LIGHT.

As used herein, the term "membrane" refers to an entity that is bound to or present on a lipid bilayer, such as a cell membrane. Thus, a membrane HVEM is bound to or present in a lipid bilayer, such as in a cell membrane or a liposome; a membrane LIGHT is bound to or present in a lipid bilayer, such as in a cell membrane or a liposome; a membrane BTLA is bound to or present in a lipid bilayer, such as in a cell membrane or a liposome; a membrane CD160 is bound to or present in a lipid bilayer, such as in a cell membrane or a liposome; and a membrane HSV gD is bound to or present in a lipid bilayer, such as in a cell membrane or a liposome.

A cis complex may include three or more entities. For example, an HVEM/BTLA cis complex can include soluble LIGHT as the third entity. Soluble LIGHT can bind to HVEM polypeptide sequence in the HVEM/BTLA cis complex without destroying the binding (cis interaction) between the HVEM and BTLA polypeptide sequences in the cis complex.

As used herein, the term "soluble" refers to an entity that is not in a lipid bilayer or cell membrane. When the entity is a polypeptide sequence, the term soluble typically refers to a polypeptide sequence that lacks a membrane binding or transmembrane domain (e.g., soluble LIGHT). Such soluble forms may include entities that facilitate solubility, or to inhibit or prevent aggregation. A specific non-limiting example is the Fc region of an immunoglobulin molecule. Specific non-limiting examples include HVEM-Fc, BTLA-Fc, CD160-Fc, LIGHT-Fc and HSV gD-Fc.

A "polypeptide" refers to two- or more amino acids linked by an amide bond. A polypeptide can also be referred to herein, inter alia, as a protein, peptide, or an amino acid sequence. Polypeptides include any length of two- or more amino acids bound by an amide bond that has been conjugated to a distinct moiety. Polypeptides can form ultra or intermolecular disulfide bonds. Polypeptides can also form higher order multimers or oligomers with the same or different polypeptide, or other molecules.

Cis complexes that include polypeptide sequences (e.g., HVEM, BTLA, LIGHT, CD160, LTα, gD, etc.) that can be mammalian (e.g., primate, murine, rattus, rabbit, guinea pig, etc.) sequences. In particular embodiments, a primate sequence includes a human, chimpanzee, gorilla, gibbon, or macaque sequence.

Cis complexes that include polypeptide sequences (e.g., HVEM, BTLA, LIGHT, CD160, LTα, gD, etc.) can include subsequences or fragments of full length (native or wild type) polypeptide sequences. Thus, for example, a cis complex that includes HVEM/BTLA, HVEM/CD160 or HVEM/ gD (as well as LIGHT as an optional third entity of a cis complex), can include a subsequence or fragment of any of HVEM, BTLA, CD160, gD or LIGHT. Such subsequences or fragments need only contain a sufficient sequence to be able to form a cis complex, i.e., a binding site for the other entity in the cis complex (e.g., a binding site for one or more of HVEM, BTLA, CD160, LIGHT, LTα, or glycoprotein D (gD) of herpes simplex virus). Thus, for example, an HVEM polypeptide sequence can include a cysteine-rich domain I (CRD1), such as a sequence that includes, consists of or is a portion of CPMCNPGYHVKQVCSEHTGTVCAPC.

Exemplary lengths of such sequences include a portion of HVEM, BTLA, CD160, LIGHT, LTα or gD polypeptide includes or consist of from about 5 to 15, 20 to 25, 25, to 50, 50 to 100, 100 to 150, 150 to 200, or 200 to 280 amino acids in length, provided that said portion is less than full-length of HVEM, BTLA, CD160, LIGHT, LTα or gD polypeptide sequence (native or wild type).

Cis complexes that include polypeptide sequences (e.g., HVEM, BTLA, LIGHT, CD160, gD, etc.) can also include substitutions of polypeptide sequences in the cis complex. Substituted sequences include HVEM, BTLA, CD160, gD, etc. binding sites that retain at least partial binding to the other entity in the cis complex (e.g., HVEM, BTLA, CD160, gD). Exemplary HVEM polypeptides include one or more amino acid substitutions of, an F for a Y residue (Y47F or Y61F), an A for an S residue (S58A), an A for an E residue (E65A or E76A) or an A for an R residue (R113A). In various embodiments, a modified polypeptide can have one or more amino acid residues substituted with another residue, added to the sequence or removed from the sequence. Specific examples include one or more amino acid substitutions, additions or deletions (e.g., 1-3, 3-5, 5-10, 10-20, or more), for example, a conservative amino acid substitution. A modified (variant) peptide can have a sequence with 50%, 60%, 70%, 75%, 80%, 85%, 90%, 95%, 96%, 97%, 98%, or more identity to a reference sequence.

Amino acid substitutions may be with the same or a different amino acid. An amino acid substitution can be where an L-amino acid is substituted with a D-form amino acid. Modifications therefore include one or more D-amino acids substituted for L-amino acids, or mixtures of D-amino acids substituted for L-amino acids.

Modifications include cyclic structures such as an end-to-end amide bond between the amino and carboxy-terminus of the molecule or ultra- or inter-molecular disulfide bond. Polypeptides may be modified in vitro or in vivo, e.g., post-translationally modified to include, for example, sugar residues, phosphate groups, ubiquitin, fatty acids, lipids, etc.

Cis complexes of the invention also include chimeras or fusions with one or more additional domains covalently linked to a polypeptide to impart a distinct or complementary function or activity. A polypeptide can have one or more non-natural or derivatized amino acid residues linked to the amide linked amino acids. Cis complex polypeptides include chimeric proteins in which two or more amino acid sequences are linked together that do not naturally exist in nature.

Exemplary fusions include domains facilitating isolation, which include, for example, metal chelating peptides such as polyhistidine tracts and histidine-tryptophan modules that allow purification on immobilized metals; protein A domains that allow purification on immobilized immunoglobulin; and the domain utilized in the FLAGS extension/ affinity purification system (Immunex Corp, Seattle Wash.). Optional inclusion of a cleavable sequence such as Factor Xa or enterokinase (Invitrogen, San Diego Calif.) between a purification domain and the peptide can be used to facilitate peptide purification. For example, an expression vector can include a peptide-encoding nucleic acid sequence linked to six histidine residues followed by a thioredoxin and an enterokinase cleavage site (see e.g., Williams, *Biochemistry* 34:1787 (1995); and Dobeli, *Protein Expr. Purif.* 12:404 (1998)). The histidine residues facilitate detection and purification of the fusion protein while the enterokinase cleavage site provides a means for purifying the peptide from the remainder of the fusion protein. Technology pertaining to vectors encoding fusion proteins and application of fusion proteins is known in the art (see e.g., Kroll, *DNA Cell. Biol.* 12:441 (1993)).

Invention cis complexes therefore include subsequences, substituted sequences (variants) and modified forms of HVEM, BTLA, CD160, gD of herpes simplex virus, LIGHT, etc. sequence that retain detectable (at least partial) binding to one or more of HVEM, BTLA, CD160, LTα, glycoprotein D (gD) of herpes simplex virus, LIGHT, etc.

Host cells can be used to produce cis complexes of the invention. For example, nucleic acids encoding polypeptides included in the cis complex (e.g., two or more of HVEM, BTLA, CD160, gD, LIGHT) can be expressed in cells. Thus, host cells that express cis complexes of the invention are also provided. In one embodiment, the host cell is a prokaryotic cell. In another embodiment, the host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded peptide or antibody expressed. The term also includes any progeny or subclones of the host cell. Progeny cells and subclones need not be identical to the parental cell since there may be mutations that occur during replication and proliferation. Nevertheless, such cells are considered to be host cells of the invention.

The invention provides isolated or purified cis complexes. In particular embodiments, complexes include two or more of HVEM, BTLA, CD160, gD, LIGHT, or LTα.

The term "isolated," when used as a modifier of an invention composition (e.g., cis complex, antibody, etc.), means that the composition ismade by the hand of man or are separated, substantially completely or at least in part, from their naturally occurring in vivo environment. Generally, isolated compositions are substantially free of one or more materials with which they normally associate with in nature (e.g., one or more protein, nucleic acid, lipid, carbohydrate, cell membrane). The term "isolated" does not exclude alternative physical forms of the composition, such as multimers/oligomers, modifications (e.g., phosphorylation, glycosylation, lipidation) or derivatized forms, or forms expressed in host cells produced by the hand of man. The term "isolated" also does not exclude forms (e.g., pharmaceutical formulations and combination compositions) in which there are combinations therein, any one of which is produced by the hand of man.

An "isolated" composition can also be "purified" when free of some, a substantial number of, most or all of the materials with which it typically associates with in nature. Thus, an isolated cis complex that also is substantially pure does not include polypeptides or polynucleotides present among millions of other sequences, such as proteins of a protein library or nucleic acids in a genomic or cDNA library, for example. A "substantially pure" composition can be combined with one or more other molecules. Thus, "substantially pure" does not exclude compositions such as pharmaceutical formulations and combination compositions.

The invention also provides antibodies (e.g., polyclonal and monoclonal antibodies) that specifically bind to invention cis complexes. Such antibodies include those specific for an HVEM/BTLA cis complex, an HVEM/CD160 cis complex, an HVEM/gD cis complex, a trimeric HVEM/BTLA/LIGHT cis complex, or a trimeric HVEM/CD160/LIGHT cis complex. In various embodiments, binding affinity of an antibody for binding to the cis complex is greater than binding affinity for the antibody for binding to a trans complex. In particular aspects, binding affinity for a cis complex including HVEM polypeptide binding to BTLA polypeptide is greater than binding affinity for a trans complex including HVEM polypeptide binding to BTLA polypeptide; binding affinity for a cis complex including HVEM polypeptide binding to CD160 polypeptide is greater than binding affinity for a trans complex including HVEM polypeptide binding to CD160 polypeptide; binding affinity for a cis complex including HVEM polypeptide binding to gD polypeptide is greater than binding affinity for a trans complex including HVEM polypeptide binding to gD polypeptide; or binding affinity for a HVEM/BTLA/LIGHT cis complex is greater than binding affinity for a trans complex including HVEM/BTLA/LIGHT (e.g., at least 10-fold, 50-fold, 100-fold, 500-fold, 1.000-fold, 5.000-fold, 10.000-fold, 50.000-fold, or 1000.000-fold greater binding affinity for the cis than trans complex). In more particular aspects, an antibody of the invention does not detectably bind to membrane bound HVEM, BTLA, or CD160, or a trans complex comprising HVEM bound BTLA, or a trans complex comprising HVEM bound CD160, or a trans complex comprising HVEM bound HSV gD. In further particular aspects, an antibody of the invention does not detectably bind to HVEM, BTLA, CD160, LIGHT or gD individually expressed in a cell (e.g., that is not in a cis complex, such as available to form a trans complex with HVEM, BTLA, CD160, LIGHT or gD).

Antibodies of the invention are useful in detecting cis complexes. Antibodies of the invention are also useful in the methods of the invention. For example, administering an invention antibody (e.g., human, humanized or chimeric) to a subject in need thereof that specifically binds to a cis complex can modulate (stimulate or increase, or inhibit, reduce or decrease) a response mediated by or associated with HVEM, BTLA, CD160, LIGHT, gD or LTα cis complex activity or function, for example, inflammation, or an immuno disorder or disease, lymphocyte or hematopoetic cell proliferation, among other things.

The invention therefore provides antibodies that bind to a cis complex and that modulate an activity, function or expression of one or more components in the cis complex (agonist or antagonist antibodies). In particular embodiments, an antibody modulates an activity, function or expression of HVEM, BTLA, CD160, LIGHT, gD or LTα. In further particular embodiments, an antibody inhibits, reduces, decreases, attenuates, suppresses, prevents or blocks, or induces, stimulates, enhances or increases an activity, function or expression of HVEM, BTLA, CD160, LIGHT, gD or LTα. In additional particular embodiments, an antibody modulates a response mediated or associated with HVEM, BTLA, CD160, LIGHT, gD or LTα activity or expression. In particular aspects, a response mediated or associated with HVEM, BTLA, CD160, LIGHT, gD or LTα activity or expression includes lymphocyte or hematopoetic cell proliferation or inflammation, proliferation, survival, differentiation, death, or activity of T cells, antigen presenting cells (e.g., dendritic cells) or B cells.

An "antibody" refers to any monoclonal or polyclonal immunoglobulin molecule, such as IgM, IgG, IgA, IgE, IgD, and any subclass thereof. Exemplary subclasses for IgG are $IgG_1$, $IgG_2$, $IgG_3$ and $IgG_4$.

Antibodies include mammalian, human, humanized or primatized forms of heavy or light chain, $V_H$ and $V_L$, respectively, immunoglobulin (Ig) molecules. Antibodies also include functional (binding) subsequences or fragments of immunoglobulins, such as Fab, Fab', $(Fab')_2$, Fv, Fd, scFv and sdFv, disulfide-linked Fv, light chain variable (VL) or heavy chain variable (VH) sequence, unless otherwise expressly stated.

As used herein, the term "monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

A cis complex antibody specifically binds to HVEM, BTLA, CD160, gD or LIGHT, in a cis complex, such as an epitope that is produced by cis interaction (binding). Such antibodies may be specific for cis complexes since the epitope(s) forms upon cis complex formation, and is therefore absent from the corresponding trans complex, or is less available for binding, than in the trans complex. Specific binding therefore includes antibodies that bind preferentially to a cis complex (e.g., one or more of HVEM/BTLA, HVEM/CD160, HVEM/gD, trimeric HVEM/BTLA/LIGHT, or trimeric HVEM/CD160/LIGHT) as compared to a corresponding trans complex (e.g., HVEM/BTLA, HVEM/CD160, HVEM/gD, trimeric HVEM/BTLA/LIGHT, or trimeric HVEM/CD160/LIGHT). Such antibodies also include those specific for binding to a cis complex that includes entities that may be a part of the cis complex, such as LIGHT in a trimeric HVEM/BTLA/LIGHT cis complex or trimeric HVEM/CD160/LIGHT cis complex. Thus, a cis complex that includes other entities such as LIGHT forms epitopes absent or less available for binding than when in a corresponding trans complex. Specific binding can be distinguished from non-specific binding using assays known in the art (e.g., immunoprecipitation, ELISA, Western blotting).

Antibodies also include antibodies that bind to cis and trans complexes. Such antibodies having the ability to bind both cis and trans complexes are also useful in the methods of the invention.

The term "human" when used in reference to an antibody, means that the amino acid sequence of the antibody is fully human, i.e., human heavy and human light chain variable and human constant regions. Thus, all of the antibody amino acids are human or exist in a human antibody. An antibody that is non-human may be made fully human by substituting the non-human amino acid residues with amino acid residues that exist in a human antibody. Amino acid residues present in human antibodies, CDR region maps and human antibody consensus residues are known (see, e.g., Kabat, *Sequences of Proteins of Immunological Interest*, 4th Ed. US Department of Health and Human Services. Public Health Service (1987); Chothia and Lesk (1987). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991). Human antibodies therefore include antibodies in which one or more amino acid residues have been substituted with one or more amino acids present in any other human antibody.

Human antibodies can be produced by immunizing human transchromosomic KM Mice™ (WO 02/43478) or HAC mice (WO 02/092812), which express human immunoglobulin genes. Using conventional hybridoma technology, splenocytes from immunized mice that respond to the antigen can be isolated and fused with myeloma cells. A monoclonal antibody can be obtained that binds to the antigen. An overview of the technology for producing human antibodies is described in Lonberg and Huszar (*Int. Rev. Immunol.* 13:65 (1995)). Transgenic animals with one or more human immunoglobulin genes (kappa or lambda) that do not express endogenous immunoglobulins are described, for example in, U.S. Pat. No. 5,939,598. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Human FR residues of the immunoglobulin can be replaced with corresponding non-human residues. Residues in the human FRs can therefore be substituted with a corresponding residue from the non-human CDR donor antibody to alter, generally to improve, antigen affinity or specificity, for example. A humanized antibody may include residues, which are found neither in the human antibody nor in the donor CDR or FR sequences. For example, a FR substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332:323 (1988)).

Antibodies referred to as "primatized" are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

Antibodies can be humanized using a variety of techniques known in the art including, for example, CDR-grafting (EP 239,400; WO91/09967; U.S. Pat. Nos. 5,225, 539; 5,530,101; and 5,585,089), veneering or resurfacing (EP 592,106; EP 519,596; Padlan, *Mol. Immunol.* 28:489 (1991); Studnicka et al., *Protein Engineering* 7:805 (1994); Roguska et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have been used to humanize antibodies (Carter et al., *Proc. Natl. Acad. Sci. USA* 89:4285 (1992); and Presta et al., *J. Immunol.* 151:2623 (1993)).

As used herein, the term "chimeric" and grammatical variations thereof, when used in reference to an antibody, means that the amino acid sequence of the antibody contains one or more portions that are derived from, obtained or isolated from, or based upon two or more different species. That is, for example, a portion of the antibody may be human (e.g., a constant region) and another portion of the antibody may be non-human (e.g., a murine heavy chain variable region or murine light chain variable region). Thus, an example of a chimeric antibody is an antibody in which different portions of the antibody are of different species origins. Unlike a humanized or primatized antibody, a chimeric antibody can have the different species sequences in any region of the antibody.

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Protein suitable for generating antibodies can be produced by any of a variety of standard protein purification or recombinant expression techniques known in the art. For example, a cis complex can be isolated from cis complex producing cells, for example, by immunoprecipitation. The polypeptides of the cis complex may be expressed by recombinant methods. A portion of the polypeptide sequence may contain an amino acid sequence such as a T7 tag or polyhistidine sequence to facilitate purification of expressed or synthesized protein. The protein may be expressed in a cell and purified.

Monoclonal antibodies can be readily generated using techniques including hybridoma, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). Suitable techniques that additionally may be employed in the method including antigen affinity purification, non-denaturing gel purification, HPLC or RP-HPLC, purification on protein A column, or any combination of these techniques. The antibody isotype can be determined using an ELISA assay, for example, a human Ig can be identified using mouse Ig-absorbed anti-human Ig.

Animals which may be immunized include mice, rabbits, rats, sheep, cows or steer, goats, or guinea pigs; such animals also include those genetically modified to include human IgG gene loci. Such animals can therefore be used to produce antibodies in accordance with the invention. Additionally, to increase the immune response, antigen can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of antigen preparation, and may be at regular or irregular intervals.

In order to screen for antibodies that bind to cis complexes, such as HVEM/BTLA or HVEM/CD160 cis complexes, cells expressing cis complexes can be used to screen antibodies. Cis complex expressing cells can be produced by recombinant technology. Exemplary cells include HVEM and BTLA expressing 293T cells (293T-HVEM-BTLA), and HVEM-CD160 co-expressing 293T cells (293T-HVEM-CD160). Bonding to such cells, including 293T-HVEM-BTLA cells and 293T-HVEM-BTLA cells can be identified by flow cytometry. To identify antibodies that bind to cells expressing cis complexes, but exhibit little or no binding to trans complexes, or membrane HVEM, BTLA or CD160, 5 types of cells for this screening procedures: (1) HVEM and BTLA expressing cells (e.g., 293T-HVEM-BTLA), (2) HVEM-CD160 coexpressing cells (e.g., 293T-HVEM-CD160), (3) HVEM expressing cells (e.g., 293T-HVEM), (4) BTLA expressing cells (e.g., 293T-BTLA), and (5) CD160 expressing cells (e.g., 293T-CD160). Antibody clones that only bind to 293T-HVEM-BTLA cells or 293T-HVEM-CD160 cells but do not substantially bind to 293T-HVEM, 293T-BTLA, and 293T-CD160 cells can be identified by flow cytometry. This screening will identify cis complex specific antibodies. Such antibodies are likely to interact with specific structures of HVEM/BTLA, HVEM/CD160, trimeric HVEM/BTLA/LIGHT, or trimeric HVEM/CD160/LIGHT cis complexes.

Cis complexes of the invention and invention antibodies can be used to modulate a HVEM, BTLA, CD160, LIGHT, gD or LTα response or signaling activity or function, selectively or non-selectively using ligands or antibodies, in solid phase, in solution, in vitro, ex vivo and in vivo. The HVEM, BTLA, CD160, LIGHT, gD or LTα can be in a cis complex or be affected by a cis complex, such as an activity or function mediated by or associated with a cis complex or an associated signaling pathway(s).

In accordance with the invention, there are provided methods of modulating a HVEM, BTLA, CD160, LIGHT, gD or LTα response or signaling activity. In one embodiment, a method includes contacting a cis complex comprising HVEM polypeptide binding to BTLA polypeptide, or a cis complex comprising a HVEM polypeptide binding to CD160 polypeptide, or a cis complex comprising HVEM polypeptide binding to gD polypeptide with a soluble LIGHT polypeptide sequence that binds to the cis complex, thereby modulating a HVEM, BTLA, CD160, LIGHT, gD or LTα response or signaling activity.

Non-limiting exemplary responses and signaling activities modulated according to the invention include lymphocyte or hematopoetic cell (e.g., T cells, antigen presenting cells or B cells) proliferation, survival, differentiation, death, or activity; an inflammatory response or inflammation (chronic or acute); secretion of a cytokine, chemokine, interleukin, or interferon (e.g., TNF, lymphotoxin (LT)-alpha, LT-beta, LIGHT, or a ligand for CD27, OX40, 41BB; CCL21, 19, or CXCL13; IL10, IL2, IL7, or IL15; or interferon type 1, or Interferon-gamma. Additional non-limiting exemplary responses and signaling activities modulated according to the invention include cytotoxic or helper activity of activated T cells, or B cell production of antibody.

Thus, in accordance with the invention, methods for inhibiting, reducing, decreasing, attenuating, preventing or blocking proliferation, survival, differentiation, death, activity or signaling of T cells, antigen presenting cells or B cells are provided. In one embodiment, a method includes contacting cells with a soluble LIGHT polypeptide sequence that binds to a HVEM/BTLA cis complex, or a HVEM/CD160 cis complex, in an amount sufficient to inhibit, reduce, decrease, attenuate, prevent or block proliferation, survival, differentiation, death, or activity of T cells, antigen presenting cells or B cells.

Compositions and methods of the invention are applicable to treating numerous disorders or undesirable conditions. Disorders and undesirable conditions treatable in accordance with the invention include disorders and undesirable conditions in which modulating a response, function or signaling activity mediated or associated with HVEM, BTLA, CD160, LIGHT, gD or LTα activity or expression, such as a cis complex that includes one or more of HVEM, BTLA, CD160, LIGHT, gD or LTα, can provide a subject with a benefit. Disorders include undesirable or aberrant, chronic or acute, immune responses, immune disorders, immune diseases, inflammatory responses and inflammation.

In accordance with the invention, additionally provided are methods for treating undesirable and aberrant, chronic and acute, immune responses, immune disorders, immune diseases, inflammatory responses and inflammation. In one embodiment, a method includes administering to a subject an amount of a composition of the invention, such as a ligand or an antibody that binds to a cis complex, effective to treat the undesirable immune response, autoimmune disorder or immune disease in the subject. In various embodiments, methods include treating chronic and acute forms of undesirable or aberrant inflammatory responses and inflammation; treating chronic and acute forms of undesirable or aberrant proliferation, survival, differentiation, death, or activity of a T cell, antigen presenting cell (e.g., dendritic cell) or B cell; and treating an autoimmune disease.

As used herein, an "undesirable immune response" or "aberrant immune response" refers to any immune response, activity or function that is greater or less than desired or physiologically normal. An undesirable immune response, function or activity can be a normal response, function or activity. Thus, normal immune responses so long as they are undesirable, even if not considered aberrant, are included within the meaning of these terms. An undesirable immune response, function or activity can also be an abnormal response, function or activity. An abnormal (aberrant) immune response, function or activity deviates from normal. Undesirable and aberrant immune responses can be humoral, cell-mediated or a combination thereof, either chronic or acute.

One non-limiting example of an undesirable or aberrant immune response is where the immune response is hyper-responsive, such as in the case of an autoimmune disorder or disease. Another example of an undesirable or aberrant immune response is where an immune response leads to acute or chronic inflammatory response or inflammation in any tissue or organ (e.g., gut). Yet another example of an undesirable or aberrant immune response is where an immune response leads to destruction of cells, tissue or organ, such as Crohn's disease, IBD or US, or a transplant, as in graft vs. host disease. Still another example of an undesirable or aberrant immune response is where the immune response is hypo-responsive, such as where response to an antigen is less than desired, e.g., tolerance has occurred. For example, tolerance to a pathogen can result in increased susceptibility to or a more severe infection, and tolerance to a tumor-associated antigen (TAA) is thought to contribute to the ability of tumors to evade immune surveillance thereby surviving and proliferating in afflicted subjects.

The terms "immune disorder" and "immune disease" mean, an immune function or activity, that is greater than (e.g., autoimmunity) or less than (e.g., immunodeficiency) desired, and which is characterized by different physiological symptoms or abnormalities, depending upon the disorder or disease. Particular non-limiting examples of immune disorders and diseases to which the invention applies include autoimmune disorders and immunodeficiencies. Autoimmune disorders are generally characterized as an undesirable or aberrant increased or inappropriate response, activity or function of the immune system Immunodeficiencies are generally characterized by decreased or insufficient humoral or cell-mediated immune responsiveness or memory, or undesirable tolerance. Disorders and diseases that can be treated in accordance with the invention include, but are not limited to, disorders and disease that cause cell or tissue/organ damage in the subject.

In accordance with the invention, there are further provided methods for inhibiting, reducing, decreasing, attenuating, preventing or blocking an immune response or inflammatory response. In one embodiment, a method includes administering to a subject an amount of a soluble LIGHT polypeptide sequence that binds to a cis complex comprising herpes virus entry mediator (HVEM) polypeptide binding to B-and T-lymphocyte attenuator (BTLA) polypeptide, sufficient to inhibit, reduce, decrease, attenuate, prevent or block an immune response or inflammatory response. In particular aspects, the immune response or inflammatory response comprises an acute or chronic inflammatory response or inflammation, or an inflammatory or autoimmune disease.

Exemplary inflammatory responses and inflammation treatable in accordance with the invention include inflammatory responses and inflammation caused by or associated with proliferation, survival, differentiation, death, or activity of T cells, antigen presenting cells (e.g., dendritic cells) or B cells. In one aspect, an inflammatory response or inflammation is, at least in part, mediated by a T cell. Methods (e.g., treatment) can result in a reduction in occurrence, frequency, severity, progression, or duration of a symptom of an inflammatory response or inflammation. Exemplary symptoms include one or more of swelling, pain, rash, headache, fever, nausea, skeletal joint stiffness, or tissue or cell damage.

Undesirable or aberrant inflammation or an inflammatory response, mediated by cellular or humoral immunity, may cause, directly or indirectly, cell, tissue or organ damage, either to multiple cells, tissues or organs, or specifically to a single cell type, tissue type or organ. Exemplary tissues and organs that can exhibit damage include epidermal or mucosal tissue, gut, bowel, pancreas, thymus, liver, kidney, spleen, skin, or a skeletal joint (e.g., knee, ankle, hip, shoulder, wrist, finger, toe, or elbow). Treatment in accordance with the invention can result in reducing, inhibiting or preventing progression or worsening of tissue damage. Such treatments can in turn lead to regeneration of a damaged organ or tissue, e.g., skin, mucosum, liver.

Undesirable or aberrant inflammation or an inflammatory response, mediated by cellular or humoral immunity, may cause, directly or indirectly, damage to a cell, tissue or organ transplant. Treatment in accordance with the invention can result in reducing, inhibiting or preventing damage to a cell or tissue or organ, including a transplanted cell, tissue or organ.

As used herein, the terms "transplant," "transplantation" and grammatical variations thereof mean grafting, implanting, or transplanting a cell, tissue or organ from one part of the body to another part, or from one individual or animal to another individual or animal. The transplanted cell, tissue or organ may therefore be an allograft or xenograft. Exemplary transplant cells include neural cells. Exemplary transplant tissues include skin, blood vessel, eye and bone marrow. Exemplary transplant organs include heart, lung, liver and kidney. The term also includes genetically modified cells, tissue and organs, e.g., by ex vivo gene therapy in which the transformed cells, tissue and organs are obtained or derived from a subject (e.g., human or animal) who then receives the transplant from a different subject (e.g., human or animal).

In accordance with the invention, there are provided methods for inhibiting, reducing, decreasing, attenuating, preventing or blocking acute or chronic inflammation or an inflammatory response. In one embodiment, a method includes administering to a subject a soluble LIGHT polypeptide sequence that binds to a cis complex, sufficient to inhibit, reduce, decrease, attenuate, prevent or block acute or chronic inflammation or an inflammatory response in the subject.

Methods of the invention that include treatment of inflammation or an inflammatory response include reducing, inhibiting or preventing occurrence, progression, severity, frequency or duration of a symptom or characteristic of an inflammatory response or inflammation. At the whole body, regional or local level, an inflammatory response or inflammation is generally characterized by swelling, pain, headache, fever, nausea, skeletal joint stiffness or lack of mobility, rash, redness or other discoloration. At the cellular level, inflammation or an inflammatory response is characterized by one or more of cell infiltration of the region, production of antibodies (e.g., autoantibodies), production of cytokines, lymphokines, chemokines, interferons and interleukins, cell growth and maturation factors (e.g., differentiation factors), cell proliferation, cell differentiation, cell accumulation or migration and cell, tissue or organ damage. Thus, treatment will reduce, inhibit or prevent occurrence, progression, severity, frequency or duration of any one or more of such symptoms or characteristics of inflammation or an inflammatory response.

In accordance with the invention, additionally provided are methods for treating autoimmune disorders and diseases in a subject having or at risk of having an autoimmune disorder or disease. In one embodiment, a method includes administering to a subject a composition of the invention, such as a ligand or an antibody that binds to a cis complex, sufficient to treat the autoimmune disorder or disease.

Exemplary autoimmune disorders treatable in accordance with the invention include rheumatoid arthritis, juvenile rheumatoid arthritis, osteoarthritis, psoriatic arthritis, diabetes mellitus, multiple sclerosis (MS), encephalomyelitis, myasthenia gravis, systemic lupus erythematosus (SLE), autoimmune thyroiditis, atopic dermatitis, eczematous dermatitis, psoriasis, Sjögren's Syndrome, Crohn's disease, inflammatory bowel disease (IBD), aphthous ulcer, iritis, conjunctivitis, keratoconjunctivitis, ulcerative colitis, asthma, allergic asthma, cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type II diabetes), immune-mediated infertility, autoimmune Addison's disease, pemphigus vulgaris, pemphigus foliaceus, dermatitis herpetiformis, autoimmune alopecia, Vitiligo, autoimmune hemolytic anemia, autoimmune thrombocytopenic purpura, pernicious anemia, Guillain-Barre syndrome, Stiff-man syndrome, acute rheumatic fever, sympathetic ophthalmia, Goodpasture's syndrome, systemic necrotizing vasculitis, antiphospholipid syndrome, allergies (e.g., allergic asthma) and graft vs. host disease.

Compositions and methods of the invention can be used to stimulate, increase, enhance, promote or induce proliferation, survival, differentiation, or activity of a T cell, antigen presenting cell (e.g., dendritic cell) or B cell can be stimulated, increased, enhanced, promoted or induced using compositions of the invention. In accordance with the invention, additionally provided are methods of stimulating, enhancing or increasing survival of a cell (in vitro, ex vivo or in vivo, such as in a subject) that express HVEM, but express less or no BTLA are provided. In one embodiment, a method includes contacting the cell with an activator of HVEM, thereby stimulating, enhancing or increasing survival of the cell. In various aspects, the cell is in a subject, such as a subject having or at risk of having an undesirable or aberrant immune response, immune disorder or immune disease, or hyperproliferative disorder. In more particular aspects, an immune disorder or immune disease includes an acute or chronic inflammatory response or inflammation or an autoimmune disorder or autoimmune disease. Exemplary cells that express little or no BTLA include epithelial cells, such as intestinal epithelial cells.

Compositions and methods of the invention can also be used to stimulate, increase, enhance, promote or induce an immune response. Thus, compositions and methods are also applicable to treat hyperproliferative disorders.

In accordance with the invention, additionally provided are methods for treating a hyperproliferative disorder. In one embodiment, a method includes administering to a subject an amount of an agent that inhibits, reduces, decreases, attenuates, prevents, blocks formation, or disrupts a cis complex sufficient to treat the neoplasia, tumor, or cancer. In various aspects, target cis complex include a cis complex that includes herpes virus entry mediator (HVEM) polypeptide binding to B-and T-lymphocyte attenuator (BTLA) polypeptide, or a herpes virus entry mediator (HVEM) polypeptide binding to CD160 polypeptide. Exemplary agents include an antibody of the invention (e.g., that binds to a cis complex that includes HVEM polypeptide, BTLA polypeptide or CD160 polypeptide), a membrane LIGHT or a combination thereof.

A "hyperproliferative disorder" refers to any undesirable or aberrant cell survival (e.g., failure to undergo programmed cell death or apoptosis), growth or proliferation. Such disorders include benign hyperplasias, non-metastatic tumors and metastatic tumors. Such disorders can affect any cell, tissue, organ in a subject. Such disorders can be present in a subject, locally, regionally or systemically.

Compositions and methods of the invention are applicable to metastatic or non-metastatic tumor, cancer, malignancy or neoplasia of any cell, organ or tissue origin. As used herein, the terms "tumor," "cancer," "malignancy," and "neoplasia" are used interchangeably and refer to a cell or population of cells whose growth, proliferation or survival is greater than growth, proliferation or survival of a normal counterpart cell, e.g. a cell proliferative or differentiative disorder. Such disorders can affect virtually any cell or tissue type, e.g., carcinoma, sarcoma, melanoma, neural, and reticuloendothelial or haematopoietic neoplastic disorders (e.g., myeloma, lymphoma or leukemia). A tumor can arise from a multitude of tissues and organs, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, which may or may not metastasize to other secondary sites.

The tumor may be in any stage, e.g., early or advanced, such as a stage I, II, III, IV or V tumor. The tumor may have been subject to a prior treatment or be stabilized (non-progressing) or in remission.

Cells comprising a tumor may be aggregated in a cell mass or be dispersed. A "solid tumor" refers to neoplasia or metastasis that typically aggregates together and forms a mass. Specific non-limiting examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterine cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Melanoma, which refers to malignant tumors of melanocytes and other cells derived from pigment cell origin that may arise in the skin, the eye (including retina), or other regions of the body, include the cells derived from the neural crest that also gives rise to the melanocyte lineage. A pre-malignant form of melanoma, known as dysplastic nevus or dysplastic nevus syndrome, is associated with melanoma development.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma A "liquid tumor," which refers to neoplasia that is diffuse in nature, as they do not typically form a solid mass. Particular examples include neoplasia of the reticuloendothelial or haematopoetic system, such as lymphomas, myelomas and leukemias. Non-limiting examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Compositions and methods of the invention include anti-proliferative, anti-tumor, anti-cancer, anti-neoplastic treatments, protocols and therapies, which include any other composition, treatment, protocol or therapeutic regimen that inhibits, decreases, retards, slows, reduces or prevents a hyperproliferative disorder, such as tumor, cancer or neoplastic growth, progression, metastasis, proliferation or survival, in vitro or in vivo. Particular non-limiting examples of an anti-proliferative (e.g., tumor) therapy include chemotherapy, immunotherapy, radiotherapy (ionizing or chemical), local thermal (hyperthermia) therapy and surgical resection. Any composition, treatment, protocol, therapy or regimen having an anti-cell proliferative activity or effect can be used in combination with a composition or method of the invention.

Anti-proliferative or anti-tumor compositions, therapies, protocols or treatments can operate by biological mechanisms that prevent, disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative and anti-tumor activities include alkylating agents, anti-metabolites, plant extracts, plant alkaloids, nitrosoureas, hormones, nucleoside and nucleotide analogues. Specific examples of drugs having anti-cell proliferative and anti-tumor activities include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds such as decitabine (5-aza-2' deoxycytidine), cytarabine, 1-beta-D-arabinofuranosyl-5-azacytosine and dihydro-5-azacytidine, bleomycin, actinomycin D, mithramycin, mitomycin C, carmustine, lomustine, semustine, streptozotocin, hydroxyurea, cisplatin, mitotane, procarbazine, dacarbazine, taxol, vinblastine, vincristine, doxorubicin and dibromomannitol.

Additional agents that are applicable in the invention compositions and methods are known in the art and can be employed. For example, monoclonal antibodies that bind tumor cells or oncogene products, such as Rituxan® and Herceptin (Trastuzumab)(anti-Her-2 neu antibody), Bevacizumab (Avastin), Zevalin, Bexxar, Oncolym, 17-1A (Edrecolomab), 3F8 (anti-neuroblastoma antibody), MDX-CTLA4 (Ipilimumab, Medarex, N.J.), Campath®, Mylotarg, IMC-C225 (Cetuximab), aurinstatin conjugates of cBR96 and cAC10 (Doronina et al. (2003). Nat Biotechnol 21:778) can be used in combination with an agent that binds to a cis complex in accordance with the invention.

Accordingly, the invention provides methods of treating a tumor, methods of treating a subject having or at risk of having a tumor, and methods of increasing effectiveness or improving an anti-tumor therapy. In respective embodiments, a method includes administering to a subject with or at risk of a tumor an amount of an agent that binds to a cis complex, sufficient to treat the tumor; an agent that binds to a cis complex sufficient to treat the subject; and administering to a subject that is undergoing or has undergone tumor therapy, an agent that binds to a cis complex sufficient to increase effectiveness of the anti-tumor therapy.

The term "contacting" means direct or indirect binding or interaction between two or more entities (e.g., between a cis complex and a ligand or agent such as an antibody, or a cis complex bearing cell and a ligand or agent such as an antibody). Contacting as used herein includes in solution, in solid phase, in vitro, ex vivo, in a cell and in vivo. Contacting in vivo can be referred to as administering, or administration.

Methods of the invention may be practiced prior to (i.e. prophylaxis), concurrently with or after evidence of the response, disorder, disease or condition begins (e.g., one or more symptoms). For example, a method may be performed before an undesirable or aberrant immune response, immune disorder, immune disease, inflammation or an inflammatory response, etc. Administering prior to, concurrently with or immediately following development of a symptom may decrease the occurrence, frequency, severity, progression, or duration of one or more symptoms of the response, disorder, disease or condition in the subject. In addition, administering a composition prior to, concurrently with or immediately following development of one or more symptoms may decrease or prevent damage to cells, tissues and organs that occurs, for example, during an undesirable or aberrant immune response, disorder or disease (e.g., an autoimmune disease), inflammation or an inflammatory response.

Compositions and the methods of the invention, such as treatment methods, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject. Therapeutic benefits and improvements include, but are not limited to, reducing or decreasing occurrence, frequency, severity, progression, or duration of one or more symptoms or complications associated with a response, disorder, disease or condition, or an underlying cause or consequential effect of the response, disorder, disease or condition. Compositions and methods of the invention therefore include providing a therapeutic benefit or improvement to a subject.

In the methods of the invention in which a therapeutic benefit or improvement is a desired outcome, a composition of the invention such as a ligand or an agent (e.g., an antibody), can be administered in a sufficient or effective amount to a subject in need thereof. An "amount sufficient" or "amount effective" refers to an amount that provides, in single or multiple doses, alone or in combination, with one or more other compositions (therapeutic agents such as a drug), treatments, protocols, or therapeutic regimens agents, a detectable response of any duration of time (long or short term), a desired outcome in or a benefit to a subject of any measurable or detectable degree or for any duration of time (e.g., for minutes, hours, days, months, years, or cured). The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is a satisfactory outcome.

The term "ameliorate" means a detectable improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatment can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods affecting one or more underlying causes of the condition, disorder, disease or symptom are therefore considered to be beneficial. Stabilizing a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

An amount sufficient or an amount effective can but need not be provided in a single administration and, can but need not be, administered alone or in combination with another composition (e.g., agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., agent), treatment, protocol or therapeutic regimen, since additional doses, amounts or duration above and beyond such doses, or additional compositions (e.g., agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, or a majority of treated subjects in a given group or population. An amount sufficient or an amount effective means sufficiency or effectiveness in a particular subject, not a group or the general population. As is typical for such methods, some subjects will exhibit a greater or less response to a treatment method.

In the case of an immune disorder or disease, treatment methods include reducing or increasing numbers or an activity of lymphocytes (e.g., T cells, antigen presenting cells or B cells) towards physiologically normal baseline levels is considered a successful treatment outcome. Similarly, a reduction or increase of circulating antibodies (e.g., auto-antibodies) considered physiologically normal or beneficial is considered a successful treatment outcome.

Additional examples of a therapeutic benefit for an undesirable or aberrant immune response, immune disorder or immune disease, inflammation or an inflammatory response is an improvement in a histopathological change caused by or associated with the immune response, disorder or disease, inflammation or an inflammatory response. For example, preventing further or reducing skeletal joint infiltration or tissue destruction, or pancreas, thymus, kidney, liver, spleen, epidermal (skin) or mucosal tissue tissue, gut or bowel (mucosal or epithelial cell) infiltration or tissue destruction.

A therapeutic benefit can also include reducing susceptibility of a subject to an acute or chronic undesirable or aberrant immune response, immune disorder or immune disease (e.g., autoimmunity, inflammation, immunodeficiency, etc.) or hastening or accelerating recovery from undesirable or aberrant immune response, immune disorder or immune disease (e.g., autoimmunity, inflammation, immunodeficiency, etc.)

Particular examples of therapeutic benefit or improvement for a hyperproliferative disorder include a reduction in cell volume (e.g., tumor size or cell mass), inhibiting an increase in cell volume, a slowing or inhibition of hyperproliferative disorder worsening or progression, stimulating cell lysis or apoptosis, reducing or inhibiting tumor metastasis, reduced mortality, prolonging lifespan. Adverse symptoms and complications associated with a hyperproliferative disorder (e.g., tumor, neoplasia, and cancer) that can be reduced or decreased include, for example, pain, nausea, lack of appetite, weakness and lethargy. Thus, inhibiting or delaying an increase in tumor cell mass or metastasis (stabilization of a disease) can increase lifespan (reduce mortality) even if only for a few days, weeks or months, even though complete ablation of the tumor has not resulted. A reduction in the occurrence, frequency, severity, progression, or duration of the underlying disorder or disease, or a symptom of the disorder or disease, such as an improvement in subjective feeling (e.g., increased energy, appetite, reduced nausea, improved mobility or psychological well being, etc.), are all examples of therapeutic benefit or improvement. A reduction in a chemotherapeutic drug, radiation or immunotherapy for treatment of a hyperproliferative disorder (e.g., a tumor) is considered as having a therapeutic effect.

As is typical for treatment or therapeutic methods, some subjects will exhibit greater or less response to a given treatment, therapeutic regiment or protocol. Thus, appropriate amounts will depend upon the condition treated (e.g., the type or stage), the therapeutic effect desired, as well as the individual subject (e.g., the bioavailability within the subject, gender, age, etc.).

The term "subject" refers to an animal, typically mammalian animal, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of immune disorders or diseases, such as CIA, EAE or BXSB animal models, as well as neoplasia, tumor and cancer models, for studying in vivo a composition of the invention.

Subjects appropriate for treatment include those having or at risk of having an undesirable or aberrant immune response, immune disorder or immune disease, those undergoing treatment for an undesirable or aberrant immune response, immune disorder or immune disease as well as those who are undergoing or have undergone treatment or therapy for an undesirable or aberrant immune response, immune disorder or immune disease, including subjects where the undesirable or aberrant immune response, immune disorder or immune disease is in remission. Specific non-limiting examples include subjects having or at risk of having an acute or chronic symptom (inflammatory response or inflammation) associated with an undesirable or aberrant immune response, immune disorder or immune disease, e.g., a subject at risk of an acute or chronic symptom associated with an autoimmune disorder or an autoimmune disease (e.g., SLE, rheumatoid arthritis, multiple sclerosis, inflammatory bowel disease, ulcerative colitis, or Crohn's disease). Further non-limiting examples include subjects having or at risk of having an immunodeficiency, such as that caused by chemotherapy or radiotherapy (ionizing or chemical) or immune-suppressive therapy following a transplant (e.g., organ or tissue such as heart, liver, lung, bone marrow, etc.). Additional non-limiting examples include subjects having or at risk of having a graft vs. host disease, e.g., a subject that is a candidate for a transplant or a subject undergoing or having received a transplant.

Subjects appropriate for treatment include those having or at risk of having a neoplasia, tumor or cancer, those undergoing as well as those who are undergoing or have undergone anti-tumor therapy, including subjects where the neoplasia, tumor or cancer is in remission. The invention is therefore applicable to treating a subject who is at risk of a neoplasia, tumor or cancer or a complication associated with a neoplasia, tumor or cancer, for example, due to neoplasia, tumor or cancer reappearance or regrowth following a period of remission.

"At risk" subjects typically have risk factors associated with undesirable or aberrant immune response, immune disorder or immune disease, inflammation or an inflammatory response, development of hyperplasia (e.g., a neoplasia, tumor or cancer). Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing neoplasia, tumor or cancer can therefore be identified by lifestyle, occupation, environmental factors, family history, and genetic screens for tumor associated genes, gene deletions or gene mutations. Subjects at risk for developing breast cancer lack Brca1, for example. Subjects at risk for developing colon cancer have early age or high frequency polyp formation, or deleted or mutated tumor suppressor genes, such as adenomatous polyposis coli (APC), for example. Susceptibility to autoimmune disease is frequently associated with MHC genotype. For example, in diabetes there is an association with HLA-DR3 and HLA-DR4.

Compositions can be administered to provide the intended effect as a single or multiple dosages, for example, in an effective or sufficient amount. Exemplary doses range from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 mg/kg, on consecutive days, or alternating days or intermittently. Single or multiple doses can be administered on the same day, consecutive days, alternating days or intermittently (e.g., every 1-5, days, 1-7 days, etc.).

Compositions can be administered and methods may be practiced via systemic, regional or local administration, by any route. For example, an antibody may be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods of the invention including pharmaceutical formulations can be administered via a (micro) encapsulated delivery system or packaged into an implant for administration.

Invention compositions and methods include pharmaceutical formulations and compositions, which refer to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical formulations and compositions can be formulated to be compatible with a particular route of administration. Formulations and compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical formulations and compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions.

Pharmaceutical formulations and delivery systems are known in the art and are applicable in the methods of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

In accordance with the invention, there are provide methods of screening a sample for the presence of an HVEM polypeptide sequence that binds to BTLA. In one embodiment, a method includes analyzing the sample for the presence of an HVEM polypeptide sequence that binds to BTLA. In various aspects, the analysis is done by nucleic acid sequencing or nucleic acid hybridization. In additional aspects, the analysis is done by contacting the sample with BTLA, or contacting an HVEM sequence (e.g., a portion or a subsequence or variant of HVEM) with BTLA in order to ascertain (measure) binding between the HVEM sequence and BTLA. Exemplary HVEM sequences include, for example, an HVEM sequence which has an arginine at position 62, a lysine at position 64, or glutamate at position 65. Further aspects include analyzing HVEM for binding to glycoprotein D of herpes simplex virus (gD), binding to LIGHT or for binding to LTα.

In accordance with the invention, there are provide methods of screening for the presence of a cis complex. In one embodiment, a method includes analyzing a sample for the presence of the cis complex comprising HVEM polypeptide bound to BTLA polypeptide. In another embodiment, a method includes analyzing a sample for the presence of the cis complex comprising HVEM polypeptide bound to CD160 polypeptide. Analyzing can be performed using ligands or agents, such as antibodies that bind to the cis complex. Thus, in various aspects, a sample is analyzed by contact of the sample with an antibody that binds to a cis complex comprising HVEM polypeptide bound to BTLA polypeptide, or an antibody that binds to a cis complex comprising HVEM polypeptide bound to CD160 polypeptide, and determining whether the antibody binds to the cis complex, or another antibody that binds to a cis complex as set forth herein.

A sample as used herein is a physical material. Samples include biological samples or materials, such as any fluid or solid material derived from or that includes a biological material, cells, proteins, etc. (e.g., blood, plasma, a tissue or organ biopsy, urine, sputum, mucous, stool, etc.)

In accordance with the invention, there are provided, methods of identifying (screening) an agent that binds to a cis complex. In one embodiment, a method includes contacting a cis complex (e.g., HVEM/BTLA polypeptide, HVEM/CD160, HVEM/gD) with a test agent; and measuring binding of the test agent to the cis complex. Binding of the test agent to the cis complex identifies the test agent as an agent that binds to the cis complex. Specificity of binding to a cis complex can be further ascertained by measuring binding of the test agent to a corresponding trans complex. Agents suitable for identifying (screening) in the methods of the invention include small molecules (e.g., organic molecules), ligands and polypeptides (e.g., antibodies).

The invention provides kits including compositions of the invention (e.g., cis complexes, corresponding binding antibodies, etc.), combination compositions and pharmaceutical formulations thereof, packaged into suitable packaging material. A kit typically includes a label or packaging insert including a description of the components or instructions for use in vitro, in vivo, or ex vivo, of the components therein. A kit can contain a collection of such components (e.g., cis complexes, antibodies that bind to cis complexes, alone, or in combination).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, a method protocol (e.g., a screening method) clinical pharmacology of an active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include, instructions for treating an undesirable or aberrant immune response, immune disorder, immune disease, inflammation or an inflammatory response, or hyperproliferative disorder. Kits of the invention therefore can additionally include labels or instructions for practicing any of the methods of the invention described herein including detection (screening), diagnostic and treatment methods.

Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can include components, in which each component is enclosed within an individual container and all of the various containers can be within a single package. Invention kits can be designed for cold storage. Invention kits can further be designed to contain host cells expressing cis complexes or antibodies of the invention. The cells in the kit can be maintained under appropriate storage conditions until the cells are ready to be used. For example, a kit including one or more cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

Several abbreviations used in the application include, for example, HVEM: herpesvirus entry mediator; BTLA: B and T lymphocyte attenuator; LIGHT: homologous to lymphotoxins, exhibits inducible expression, and competes with HSV glycoprotein D for HVEM, a receptor expressed by T lymphocytes, or TNFSF14; CRD: cysteine-rich domain(s); gD: herpes simplex virus envelope glycoprotein D; HSV-1: Herpes Simplex virus-1; LTα: lymphotoxin-α; TNFSF: tumor necrosis factor superfamily; TNFRSF: TNF receptor superfamily.

As used herein, the singular forms "a", "and," and "the" include plural referents unless the context clearly indicates otherwise. Thus, for example, reference to "a cis complex" or an "antibody" includes a plurality of such cis complexes sites or antibodies and reference to "a response, activity or function" can include reference to one or more responses, activities or functions, and so forth.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a series of ranges includes combined ranges in any combination. Thus, for example, reference to a series of ranges such as 25-250, 250-500, 500-1000, 1000-2500 or 2500-5000, 5000-25,000, 5000-50,000 pg/kg includes combined ranges, such as 25-500, 25-1000, 250-1000, 2500-25,000, 1000-50,000, 5000-50,000, etc.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressly herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This Example Describes Materials and Methods Used in Examples 2 to 12
Reagents and Cell Lines Antibodies used included: mouse anti-BTLA mAb (J168, IgG1κ; BD Bioscience, San Diego, Calif.), mouse anti-HVEM mAb (clone 94801, R&D System, Emeryville, Calif.), mouse anti-mouse BTLA mAb (6F7), Armenian Hamster anti-HVEM mAb (LH1), mouse anti-human HVEM (eBioHVEM-122), and mouse anti-human BTLA (MIH26) (eBioscience, San Diego, Calif.); mouse anti-FLAG mAb (M2 clone, Sigma-Aldrich, St. Louis, Mo.), rabbit-anti-Rel A/p65 Ab (C-20), anti-RelB (C-19) and anti-TRAF3 Ab (H-122) (Santa Cruz Biotechnology) and rat anti-TRAF2 mAb (6F8 clone, MBL, Nagoya, Japan). Rat anti-BTLA mAb (6F4, IgG1κ), goat anti-HVEM and anti-LTβR IgG were made in-house against purified receptor Fc proteins as described (Rooney, et al., *Methods Enzymol* 322:345 (2000)). Purified Fc fusion proteins: HVEM-Fc, BTLA-Fc and LTβR-Fc, of mouse or human origin, were produced and purified as described (Cheung, et al., *Proc Natl Acad Sci USA* 102:13218 (2005)). Recombinant soluble human LIGHT truncated at G66 (LIGHTt66), eliminating the cytosolic and transmembrane regions, was purified and characterized as described (Rooney, et al., *J. Biol. Chem.* 275:14307 (2000)).

Recombinant cyan fluorescent protein tagged HVEM (HVEM-CFP) plasmid was generated by inserting the full-length HVEM sequence upstream of the ECFP gene of the pECFP-N1 expression vector (Clontech Laboratories Inc., Mountain View, Calif.). Recombinant red fluorescent protein tagged BTLA plasmid (BTLA-DsRed) was constructed by inserting the full-length BTLA sequence into the pDsRed vector (Clontech). The BTLA-A117-pcDNA3 was used in all studies except in FIG. 2 where the BTLA-V117 variant was utilized. HVEM-Y61A and HVEM-Y61F mutants were made with a QuikChange site-directed mutagenesis kit (Stratagene, San Diego, Calif.) and confirmed by DNA sequencing of the entire coding region.

The retroviral vector, pMIG-GFP, was used to introduce LIGHT or CD160 into EL4 cells, and BTLA into human dermal fibroblasts (Cheung, et al., *Proc Natl Acad Sci USA* 102:13218 (2005)). The HVEM-pBABE retroviral vector was used for stable expression of HVEM in 293T cells, and BTLA-pMIG was used to create stable 293T-HVEM-BTLA coexpressing cells. Calcium phosphate precipitation was used to transiently transfect 293T cells with BTLA-pcDNA3 or NF-κB luciferase reporter. The mouse PE16 T cell hybridoma was derived from fusion of BW50 T thymoma cells with T cells from AND transgenic mice crossed with OX40$^{-/-}$ mice.

T Cell Cotransfers into Hvem- and Btla-Deficient Rag$^{-/-}$ Recipients

C57BL/6, Rag$^{-/-}$ (C57BL/6 background), and C57BL/6-SJL CD45.1 congenic mice were purchased from the Jackson Laboratory. Btla$^{-/-}$, Hvem$^{-/-}$ and Rae Hvem- or Btla-deficient mice have been described previously (Steinberg, et al., *J Exp Med* 205:1463 (2008)). Mice were maintained under specific pathogen-free conditions and used at 7-12 wk of age. CD4$^+$ CD45RB$^{high}$ T cells were enriched from splenocyte suspensions by positive selection using anti-CD4 (L3T4) microbeads and further purified by cell sorting. For cotransfer studies, 5×10$^5$ CD4$^+$ CD45RB$^{high}$ T cells isolated from congenic CD45.1$^+$ mice were mixed with 5×10$^5$CD4$^+$ CD45RB$^{high}$ T cells (CD45.2$^+$) obtained from Btla$^{-/-}$, Hvem$^{-/-}$, or double deficient mice, and injected i.v. into Hvem$^{-/-}$Rag$^{-/-}$ or Btla$^{-/-}$Rag$^{-/-}$ recipients as described (Steinberg, et al., *J Exp Med* 205:1463 (2008)). Transferred mice were monitored regularly for signs of disease, including weight loss, hunched appearance, piloerection of the coat, and diarrhea.

HVEM-BTLA Cis Complex Assay

T cells were enriched from mouse spleens by negative selection using biotinylated anti-mouse B220-, DX5-, CD11b-, CD11c- and Ter119 mAbs (clones RA3-6B2, DX5, M1/70, HL-3, Ter119 eBioscience/BD Bioscience) and selection with magnetic streptavidin-beads (iMAG, BD Pharmingen). The enriched T cells fraction were incubated with anti-mouse BTLA (6F7), HVEM (LH1) mAbs or mouse BTLA-Fc and analyzed by flow cytometry. Human mononuclear cells were isolated from human blood using Ficoll gradient centrifugation. T cells were identified with anti-human CD3, and costained with anti-human BTLA (MIH26) and anti-human HVEM (eBioHVEM122) mAb and analyzed by flow cytometry.

Flow cytometry-based binding assays with antibody or Fc fusion proteins were carried out as described (Cheung, et al., *Proc Natl Acad Sci USA* 102:13218 (2005)). Ligands were incubated with cells in binding buffer (PBS with 2% FBS) for 45 min, washed and stained with RPE conjugated goat anti-human IgG Fcγ (Jackson ImmunoResearch, West Grove, Pa.) or anti-mouse RPE (detection of Flag epitope). Mean fluorescence values were analyzed by nonlinear regression.

Immunoprecipitation was performed in nonionic detergent cell lysates with isolation of immune complexes with immobilized Protein-G Sepharose beads and detection of the antigen by SDS-PAGE and Western blotting as described (Rooney, et al., *J. Biol. Chem.* 275:14307 (2000)).

Cellular Assays 293T cells were cotransfected with the dual-luciferase reporter plasmids (pNF-κB, Stratagene, San Diego, Calif.; pRL-TK, Promega, Medison, Wis.) and various combinations of ligands added to cell cultures overnight. Cell lysates were prepared and the luciferase activity was measured with the Dual-Luciferase Reporter Assay System™ (Promega).

Human colon adenocarcinoma (HT29) or mouse T cell hybridoma (PE16) cells were cultured on chambered coverglass (Nalge Nunce International). Cells were treated with ligands for the indicated time, then fixed in 4% paraformaldehyde for 10 min and permeabilized with 0.2% Triton-X-100/PBS for 15 min. After blocking with 1% BSA/0.1% Triton-X-100/PBS for 1 hr, slides were incubated with anti-RelA/p65 and detected with Cy5 or Cy3 conjugated anti-rabbit antibody (Jackson ImmunoResearch Laboratory). Cells were counter stained with DAPI solution (1 µg/ml) and visualized with a Marianas fluorescence microscope using 40× or 63×1.3 numerical aperture oil immersion objective (Carl Zeiss, Inc., Oberkochen, Germany) and images were analyzed with SlideBook software (version 4.2.09). Cultures of T cells ($1 \times 10^5$/ml) negatively selected WT or Btla$^{-/-}$CD4$^+$ or CD8$^+$CD25$^-$ T cells were labeled with carboxy-fluorescein diacetate succinimidylester (CFSE) and cultured in 96 well plates coated with 1 µg/ml of anti-CD3ε mAb and in medium 0.5 µg/ml of anti-CD28 mAb and 10 µg/ml of mouse BTLA:Fc or IgG1 isotype control. Cell proliferation and apoptosis was determined by flow cytometric monitoring CFSE dilution at day 3 and 7-aminoactinomycin D cell viability dye exclusion at day 5 of culture, respectively.

Fluorescence Resonance Energy Transfer (FRET)

HVEM-CFP and BTLA-DsRed were expressed in 293T cells by transient transfection. Detection of fluorescence was performed using a LSRII flow cytometry system (BD Biosciences) fitted with solid state diode lasers (Coherent, Santa Clara, Calif.). HVEM-CFP and BTLA-DsRed coexpressing cells, HVEM-CFP cells, and BTLA-DsRed cells were detected at the CFP channel (excitation at 405 nm, emission at 425-475 nm), DsRed channel (excitation at 488 nm, emission at 562-588 nm with a 535 nm long pass filter), and FRET channel (excitation at 405 nm, emission at 564-606 nm with a 550 nm long pass filter). The data were analyzed with Flowjo software (version 8.5.3). Specific FRET fluorescence was calculated as: FRET=Total emission collection at the FRET channel—CFP spectral overlap—DsRed emission at 405 nm laser excitation. The amount of CFP fluorescence spectral overlap subtracted was derived from the mean fluorescence observed in the FRET channel from 293T cells expressing HVEM-CFP (293T-HVEM-CFP). To ensure the CFP fluorescence of the spectral overlap was subtracted from the HVEM-CFP and BTLA-DsRed coexpressing cells, 293T-HVEM-CFP should have equal or slightly higher levels of CFP expression compared to coexpressing cells. Similar accounting was considered for DsRed background fluorescence. Control studies showed no non-specific interactions between CFP and DsRed, CFP and BTLA or HVEM, or DsRed and BTLA or HVEM (Cheung, et al., *Proc. Nat. Acad. Sci. USA*. 106:6244 (2009))

HVEM-CFP and BTLA-DsRed subcellular localization in transfected 293T cells were observed by confocal microscopy utilizing a Bio-Rad confocal system (Bio-Rad, Hercules, Calif.) fitted to a Nikon microscope with a 40×1.3 numerical aperture oil immersion objective (Nikon Instruments Inc., Melville, N.Y.). The pinhole was set at 1 Airy disc unit. HVEM-CFP and BTLA-DsRed expressing cells were visualized by illumination using a Coherent Enterprise Kr—Ar-visible laser (Coherent) with the laser line set at 488 nm for CFP; 568 nm for DsRed. The fluorescence was detected at an emission window of 504-540 nm for CFP; 589-621 nm for DsRed. The image was recorded at a frame-average of five.

Example 2

This Example Includes Studies Showing Expression Patterns of Intrinsic BTLA and HVEM Complex in T Cells The possibility that HVEM and BTLA act in cis, implicated T cells may coexpress HVEM and BTLA. The expression patterns of HVEM and BTLA in mouse and human naïve T cells isolated from spleen or peripheral blood, respectively using specific mAb were studied. Indeed, the vast majority of CD3$^+$ T cells obtained from human and mouse coexpressed HVEM and BTLA, suggesting a pattern of expression conserved across species. Both major subsets of mouse T lymphocytes coexpressed HVEM and BTLA with CD4 T cells expressing relatively more BTLA than CD8 T cells.

Example 3

This Example Includes Studies Showing Cis-Interaction Between HVEM and BTLA

Dendritic cells, and T and B lymphocytes depending on their state of activation, coexpress HVEM and BTLA (De Trez, et al., *J Immunol* (2008) 180:238; Sedy, et al., *Nat Rev Immunol* (2005) 8:861) indicating the potential for ligand receptor complex formation in cis. To determine whether HVEM and BTLA form a complex when coexpressed in the same cells, 293T cells were transfected with BTLA, HVEM or both, and HVEM immunoprecipitated from lysates with aid of a Flag-epitope tag (HVEM-Flag). BTLA specifically coimmunoprecipitated with HVEM-Flag in cells coexpressing HVEM and BTLA (FIG. 1A, lane 4). In contrast, BTLA did not associate with HVEM when immunoprecipitated from a mixture of HVEM expressing 293T cells (293T-HVEM) and BTLA expressing 293T cells (293T-BTLA) (FIG. 1A, lane 3). This result indicated HVEM-BTLA forms a stable complex in cis, but not in trans.

Figure 1C:
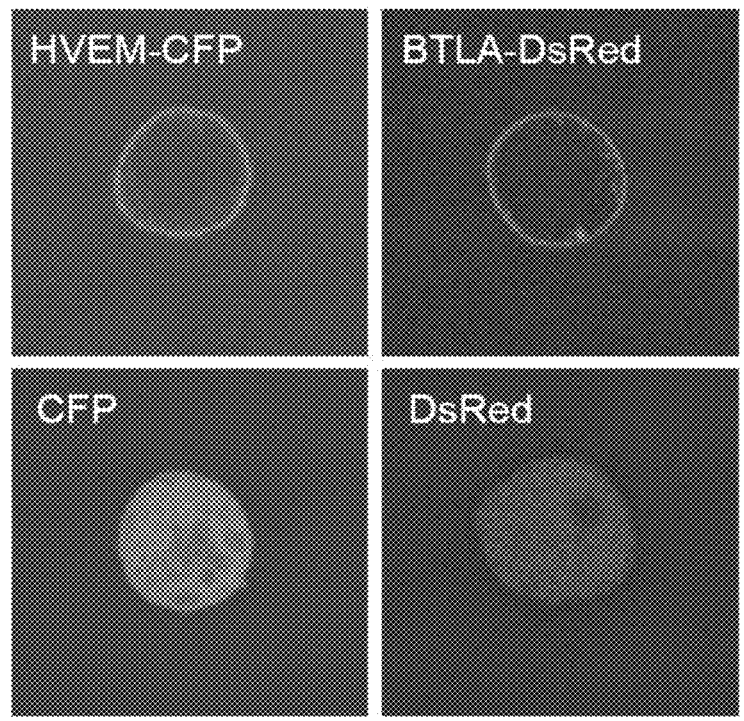
Figure 1D:
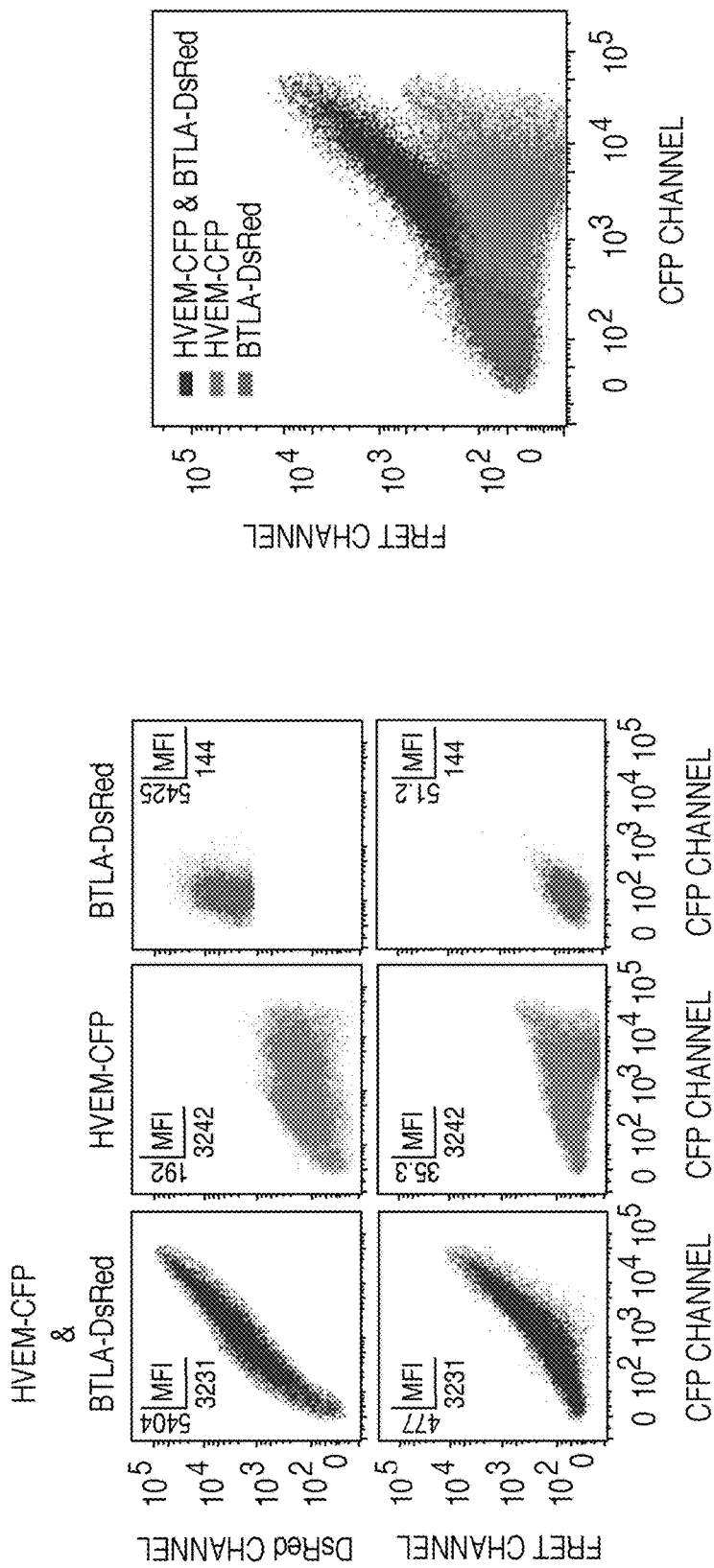
Figure 1E:
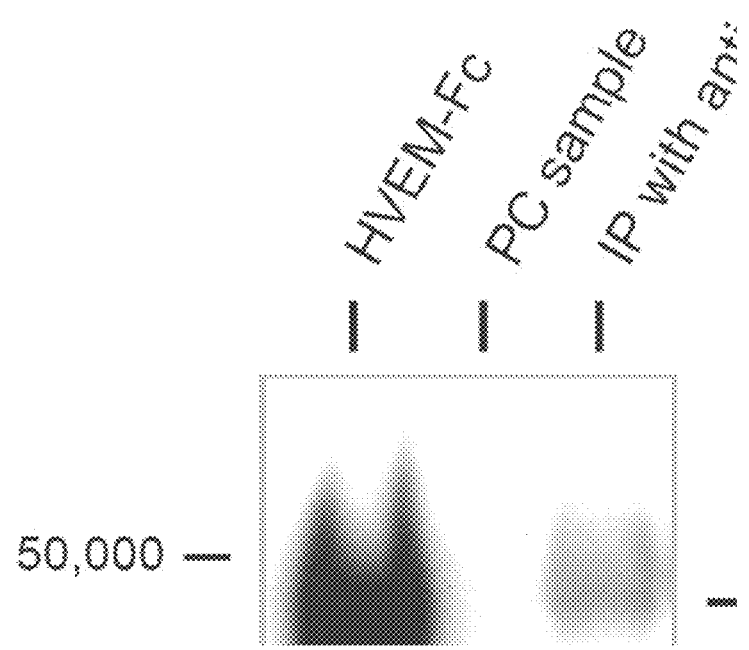

To measure HVEM and BTLA interactions in native membranes of viable cells a fluorescence resonance energy transfer (FRET) system to monitor interactions was developed. This assay utilized cyan-fluorescence protein (CFP) fused to the cytosolic tail of HVEM (HVEM-CFP) as a donor fluorophore, and DsRed fused at the C-terminus of BTLA (BTLA-DsRed) as an acceptor fluorophore (FIG. 1B). Both HVEM-CFP and BTLA-DsRed localized to the plasma membrane when visualized by confocal microscopy, although the nonconjugated CFP and DsRed proteins showed a uniform cytoplasmic pattern (FIG. 1C). To enhance quantitative aspects of FRET, a flow cytometric detection system was used in which CFP was excited by a solid state diode laser at 405 nm, and the FRET detected at 564-606 nm Flow cytometric analysis revealed strong fluorescence in HVEM-CFP and BTLA-DsRed coexpressing cells detected in the FRET channel with minimal CFP spectral overlap and DsRed coexctiation (FIG. 1D, right panel). The left panel of FIG. 1D shows the overlay of the FRET channel. Importantly, BTLA also coimmunoprecipitated with HVEM in lysates obtained from the mouse CD4$^+$ T cell hybridoma PE16, which also coexpressed both HVEM and BTLA at levels comparable to those observed in primary T cells (FIG. 1E). This result indicates formation of the HVEM-BTLA complex in cis occurs at cellular physiological levels.

Example 4

Figure 2A:
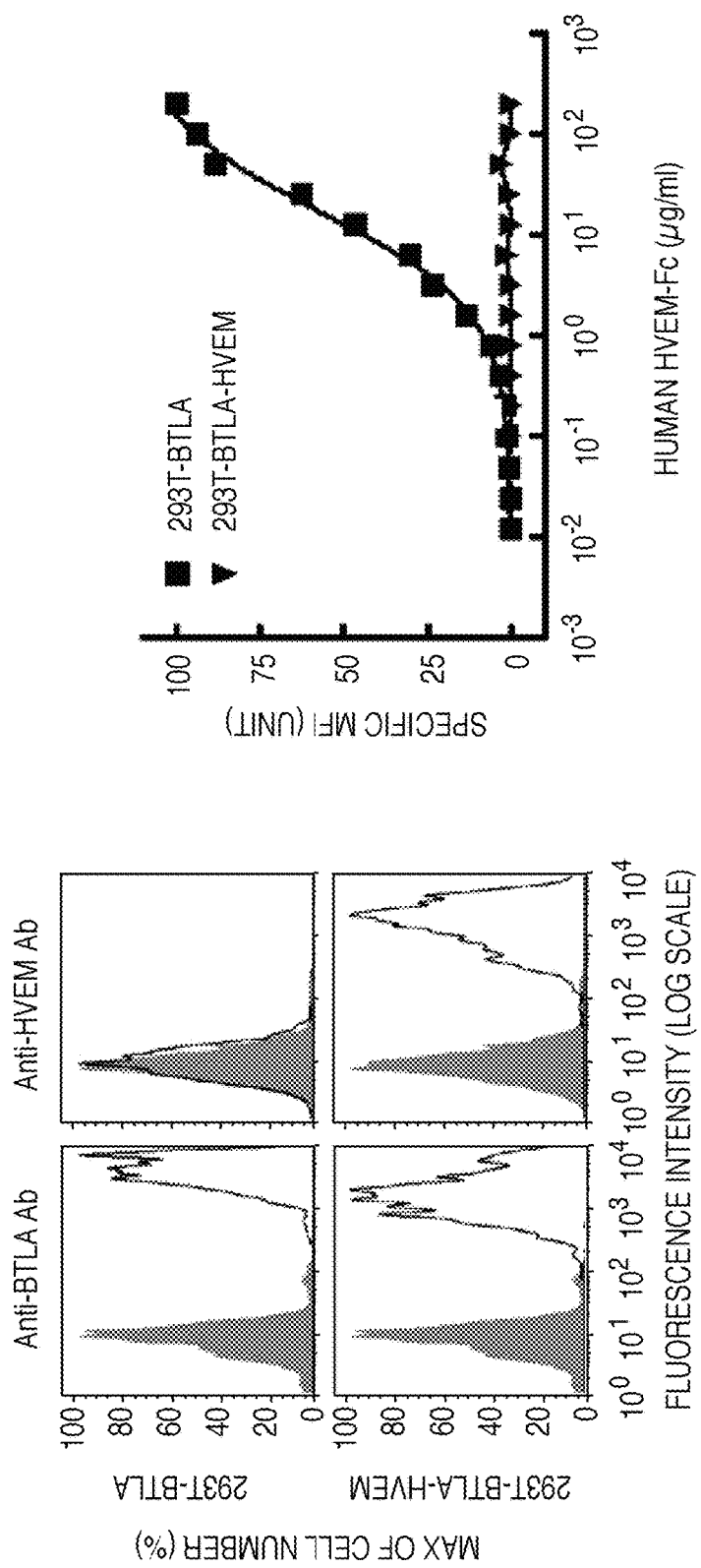

This Example Includes Studies Showing Cis-Association Restricts Trans-Interaction Between HVEM and BTLA HVEM-Fc, a soluble dimeric form of HVEM, binds specifically and with a saturable dose response to BTLA expressed in 293T cells, however in cells coexpressing HVEM and BTLA blocked binding of soluble HVEM-Fc to BTLA on the cell surface (FIG. 2A). This result indicated the HVEM-BTLA complex in cis inhibited trans-interaction between BTLA and HVEM.

Figure 2B:
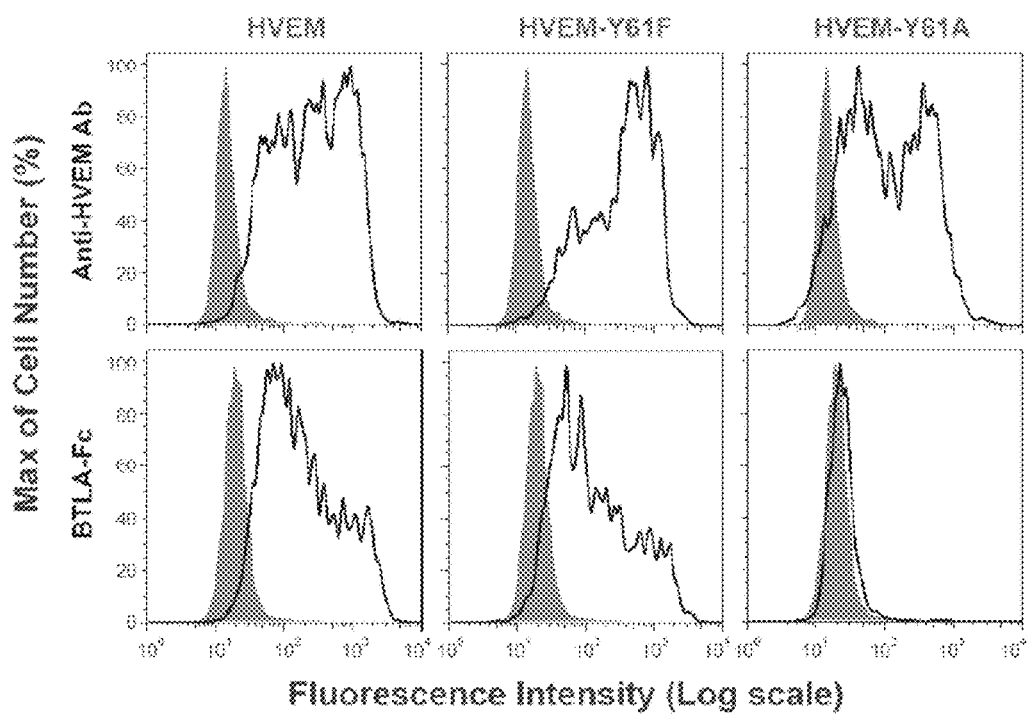
Figure 2C:
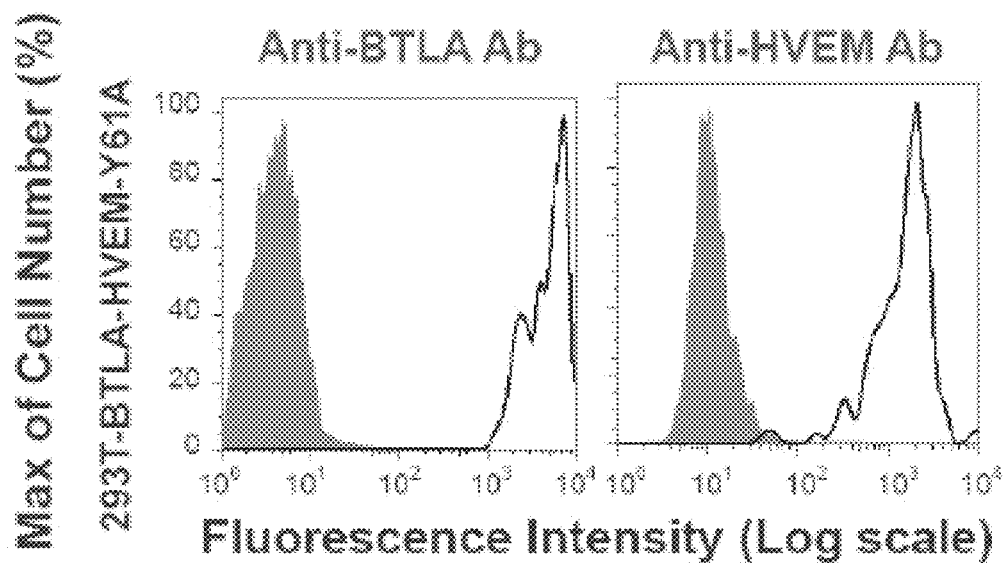
Figure 2C:
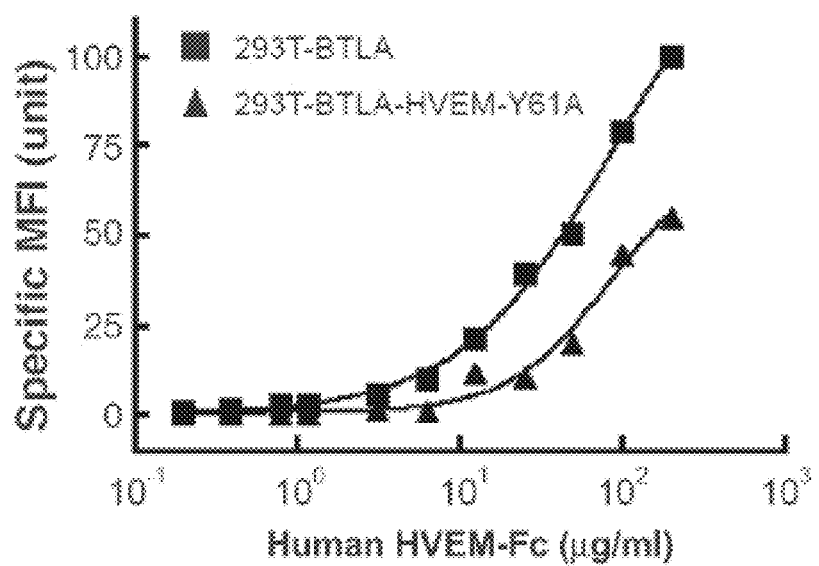

Mutation in the CRD1 region of HVEM-Fc at tyrosine-61 to alanine (Y61A), but not to phenylalanine (Y61F) abolished binding capability to BTLA without impacting cell surface expression (FIG. 2B).

Figure 2D:
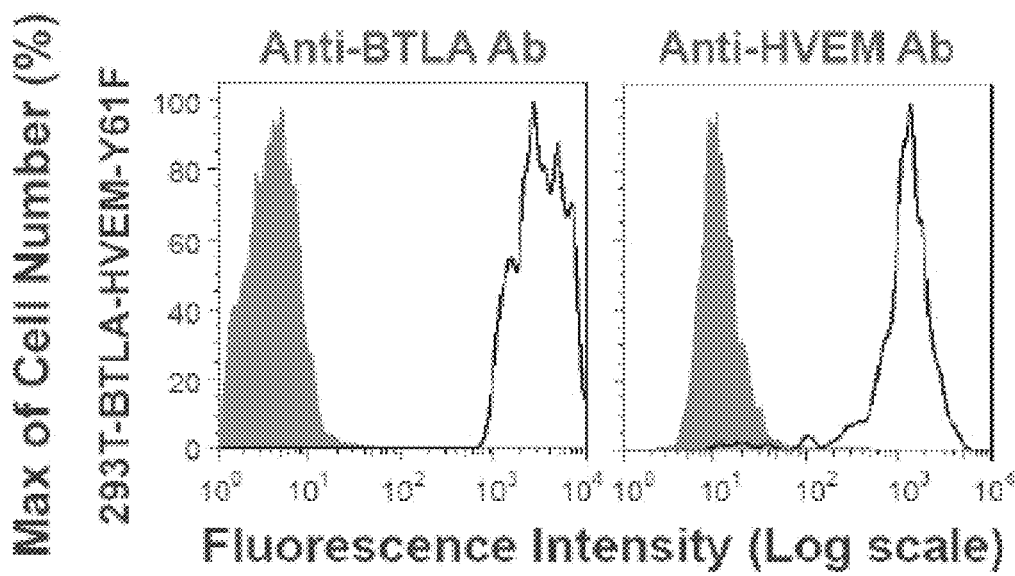
Figure 2D:
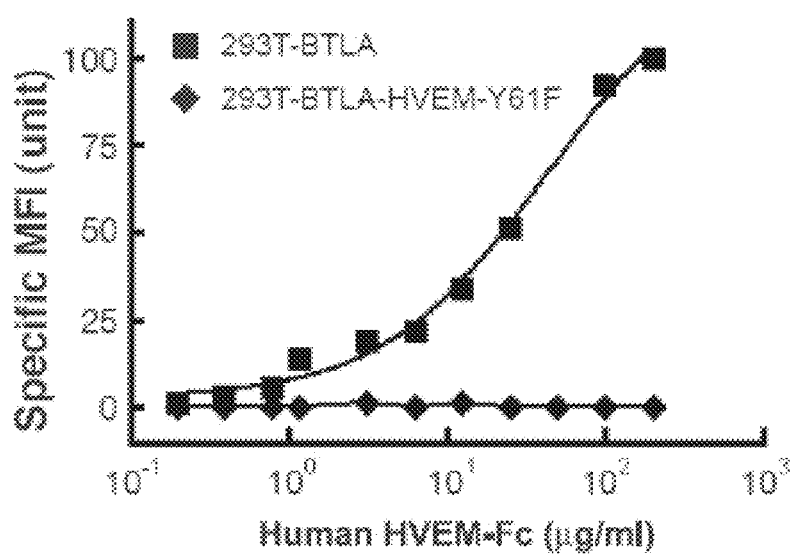

In contrast to wild type HVEM, coexpression of the HVEM-Y61A mutant with BTLA ablated the cis acting inhibitory effect of membrane BTLA binding to HVEM-Fc (FIG. 2C), suggesting that membrane BTLA was available to bind with HVEM-Fc. Coexpression of HVEM-Y61F mutant, which retains BTLA binding, like wild type HVEM, inhibited trans binding between HVEM-Fc and BTLA, indicating that membrane-BTLA molecules were occupied by HVEM-Y61F (FIG. 2D). These mutants provide strong evidence that the cis and trans binding between HVEM and BTLA occur in the same region of CRD1 of HVEM.

The cis complex in primary mouse CD3$^+$ T lymphocytes appeared to block trans interactions between HVEM and BTLA. Indeed, mouse BTLA-Fc bound to BTLA-deficient T cells with a 4-5 fold increase above WT T cells (MFI ratio of Btla$^{-/-}$ T cells to WT T cells=4.4) (FIG. 2E, left histogram). At saturating conditions, WT T cells specifically bound some BTLA-Fc suggesting naïve T lymphocytes expressed a limited amount of free HVEM on the surface not engaged in a cis interaction with BTLA (FIG. 2E, left histogram). However, when measured with specific antibodies (which do not block binding), T cells from gene-deficient mice displayed the same level of surface protein as T cells from WT mice (FIG. 2E, middle and right histograms). These results indicate the HVEM-BTLA cis complex is the predominant form of HVEM and BTLA expressed in primary naïve T cells. Furthermore, the formation of cis complex limited trans interactions between HVEM and BTLA.

The data indicate that naïve T cells constitutively coexpress HVEM and BTLA as a cis complex heterodimer which functions to limit HVEM signaling by all of its cellular ligands, including LIGHT, BTLA and CD160. The cis complex represents ~80% of HVEM and BTLA expressed on the surface a naïve T cell (FIG. 2E). Co-immunoprecipitation and FRET analyses indicated a high level of HVEM-BTLA cis complex stability, and localization of the cis complex to the cell surface. Previous structural reports implicated the trans complex as the likely primary conformation that activates signaling of the HVEM-BTLA complex (Compaan, et al., *J Biol Chem* 280:39553 (2005); however, the HVEM Y61A mutant demonstrated both the cis and trans configurations utilize the same binding motif. Moreover, deletion of the cytosolic domain of BTLA did not impact the inhibitory function of the cis complex demonstrating that the interaction of the ecto domains determines the functional outcome. Accommodating the cis complex into the structural model of HVEM suggests a distinct conformation for the interacting partners, perhaps involving conformational flexibility in HVEM. The <100 Å distance determined by FRET and the elongated structure of HVEM ectodomain compared with the compact, Ig-domain of BTLA suggests HVEM may need to "bend" to accommodate BTLA in the same membrane plane. The structural flexibility of HVEM in the membrane proximal CRD3 and 4, which contain nearly 60 residues disordered in the crystal structure (Carfi, et al., *Molecular Cell* 8:169 (2001), Compaan, et al., *J Biol Chem* 280:39553 (2005)), could theoretically contribute to a supine contortion of HVEM necessary to accommodate BTLA in cis complex form.

Example 5

Figure 3A:
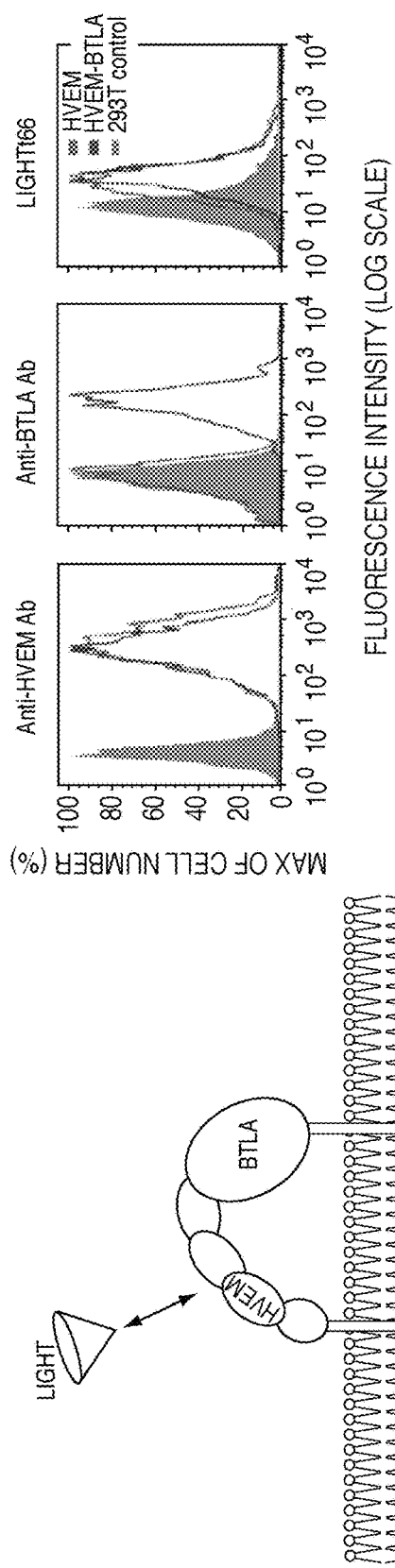

This Example Includes Studies Showing that HVEM-BTLA Cis-Interaction Modulates LIGHT-Mediated HVEM Signaling LIGHT engages HVEM in a topographically distinct site from the binding site for BTLA (Gonzalez, et al., *Proc Natl Acad Sci USA* (2005) 102:1116; Cheung, et al., *Proc Natl Acad Sci USA* (2005) 102:13218). To determine if HVEM-BTLA cis complex altered LIGHT binding the interaction of soluble LIGHT (LIGHTt66) with 293T cells coexpressing HVEM and BTLA was measured (FIG. 3A, right panel). The results show that cis-association between HVEM and BTLA allowed binding of soluble LIGHT as well as HVEM expressed without BTLA (FIG. 3A, left panel).

An NF-κB-dependent Luciferase reporter assay was used to determine the effect of coexpression of HVEM and BTLA on activation of HVEM and signaling initiated by membrane LIGHT (EL4-LIGHT) or soluble LIGHT. HVEM expressed by itself or in a cis configuration with BTLA failed to specifically activate NF-κB as compared with expression of NF-κB inducing kinase (NIK) (FIG. 3B). However, co-culture of EL4-LIGHT cells, but not EL4 cells with 239T-HVEM (at 1:1 ratio) effectively activated the NF-κB reporter (FIG. 3B).

Figure 3C:
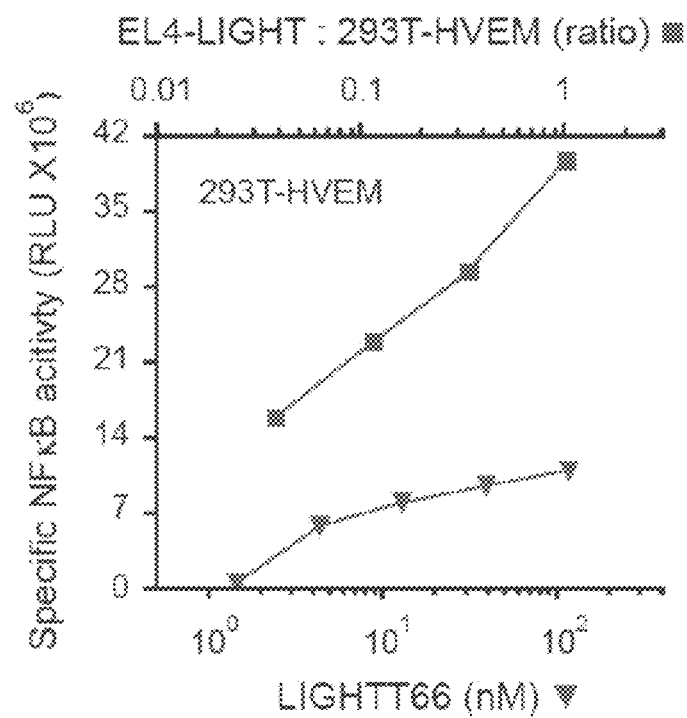
Figure 3C:
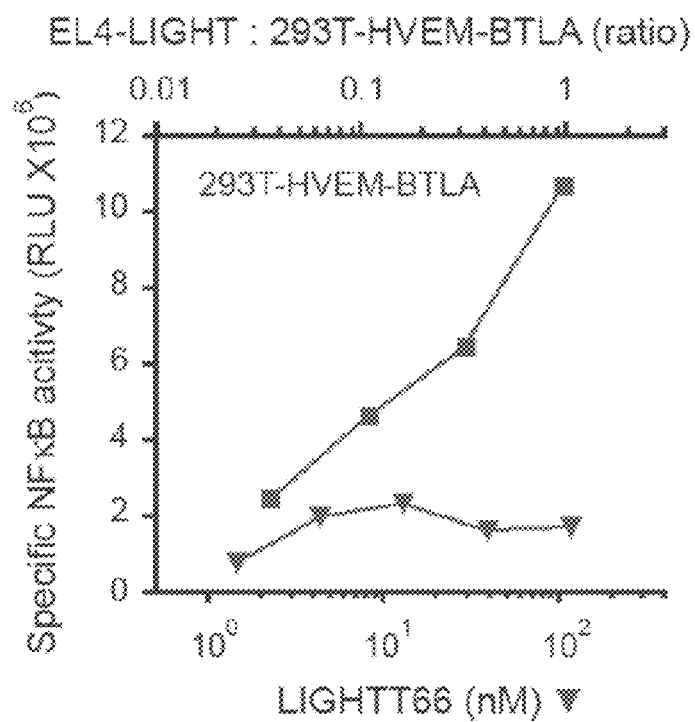
Figure 3D:
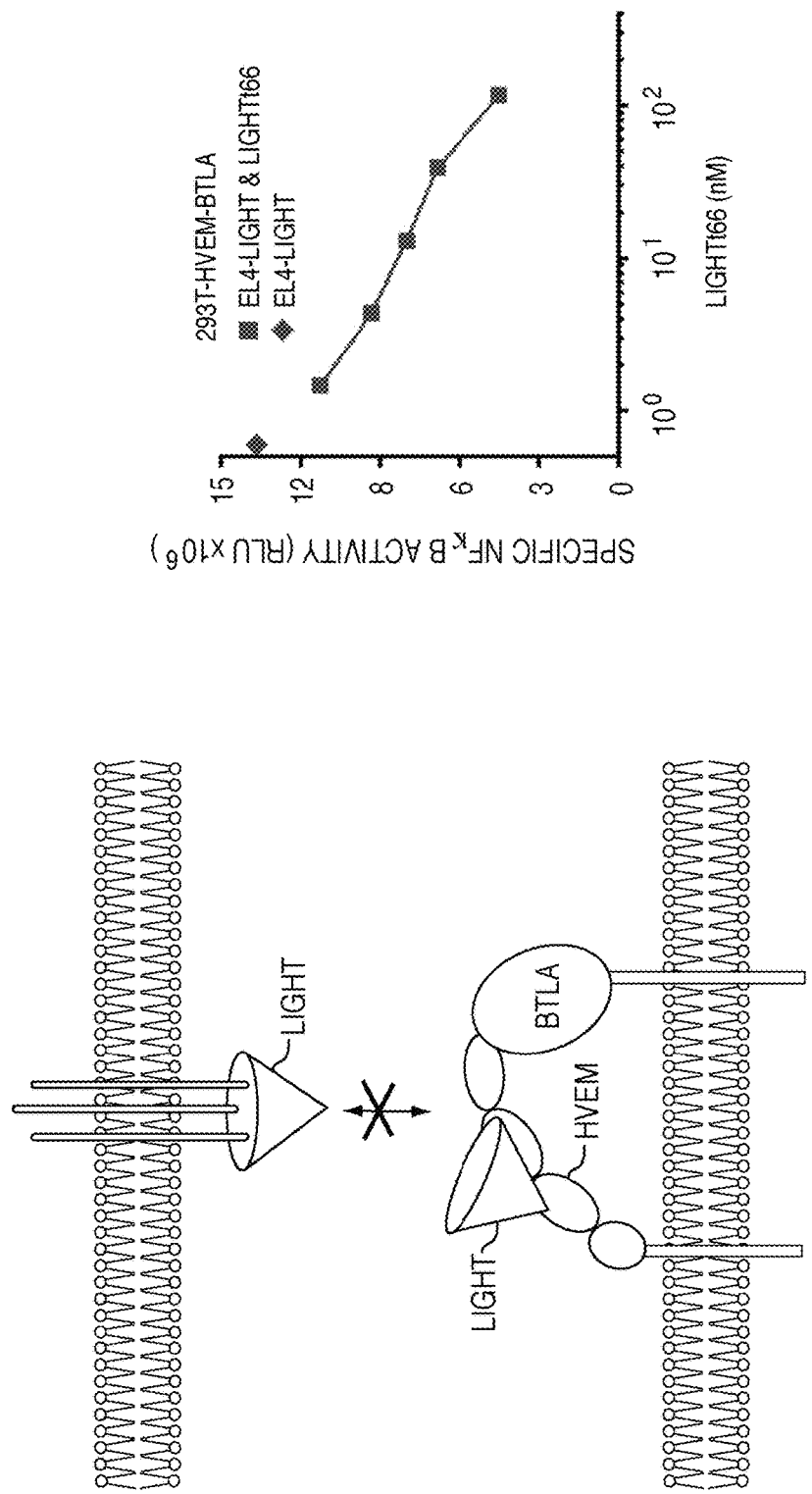

Soluble LIGHT and EL4 cells expressing membrane LIGHT both specifically and dose dependently activated the NF-κB reporter in 293T-HVEM cells (FIG. 3C, left panel), although the magnitude of the Luciferase signal was substantially greater with membrane LIGHT in EL4 cells compared with saturating levels of soluble LIGHT. However, coexpression of HVEM with BTLA completely blocked the ability of soluble LIGHT to activate HVEM signaling, even though binding of LIGHT was not blocked by BTLA coexpression (FIG. 3C, right panel). This result suggested the configuration of HVEM-BTLA cis complex may not allow soluble LIGHT to oligomerize HVEM into an active signaling complex. EL4 cells expressing membrane LIGHT retained the ability to activate NF-κB, although the magnitude was attenuated in NF-κB reporter cells that coexpressed HVEM and BTLA (FIG. 3C, right panel). Soluble LIGHT inhibited activation HVEM when added to cultures with EL4-LIGHT cells suggesting soluble LIGHT functions as a competitive inhibitor of membrane LIGHT in cells coexpressing HVEM and BTLA (FIG. 3D).

Example 6

Figure 4B:
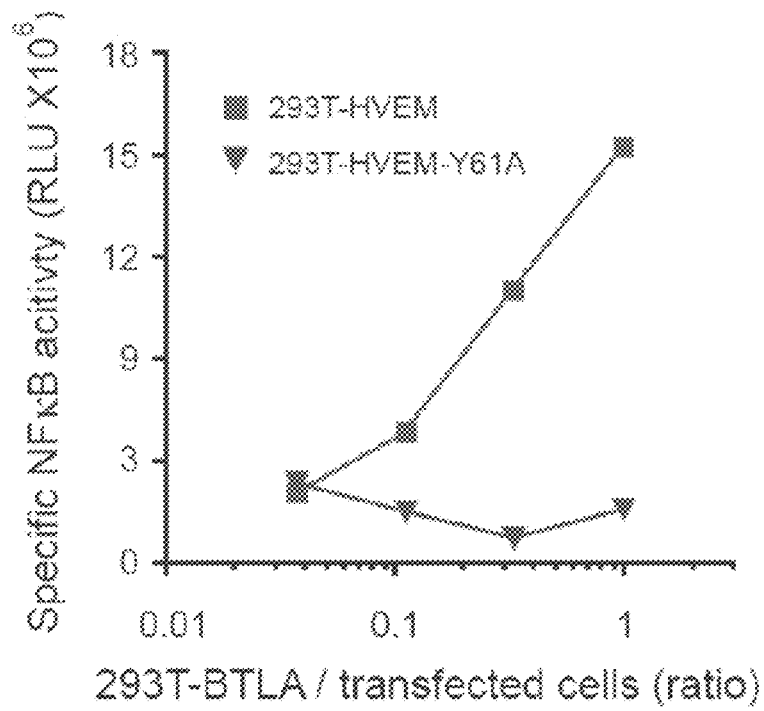
Figure 4B:
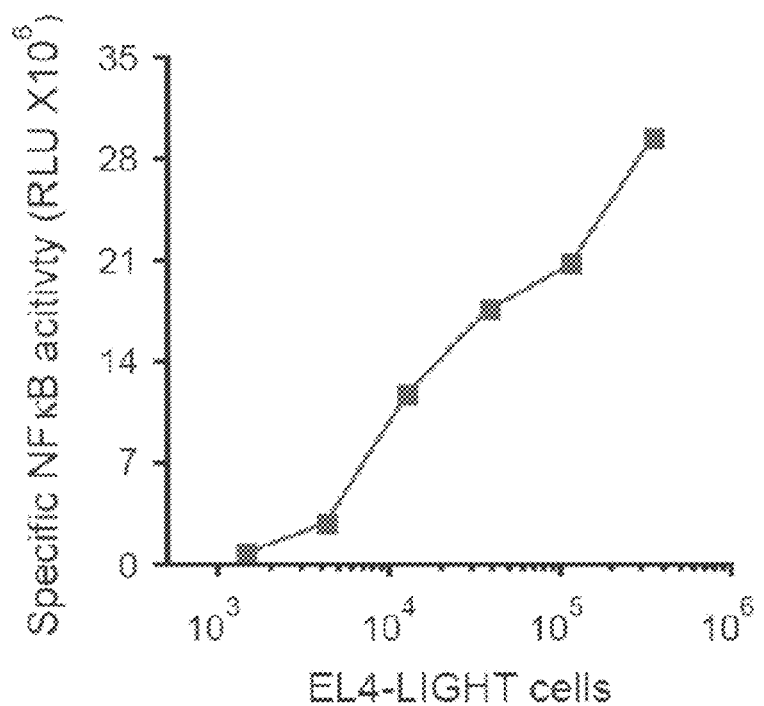
Figure 4C:
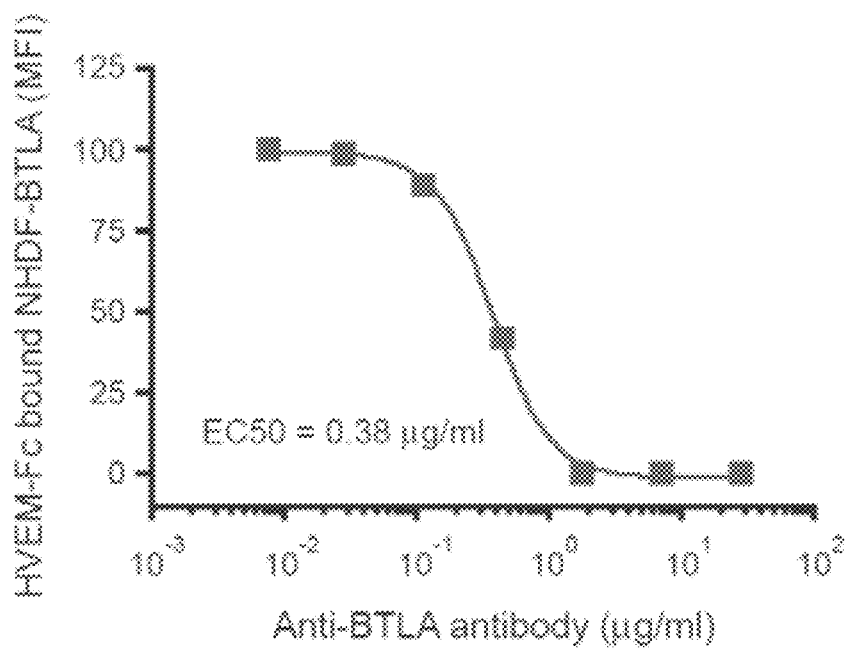
Figure 4C:
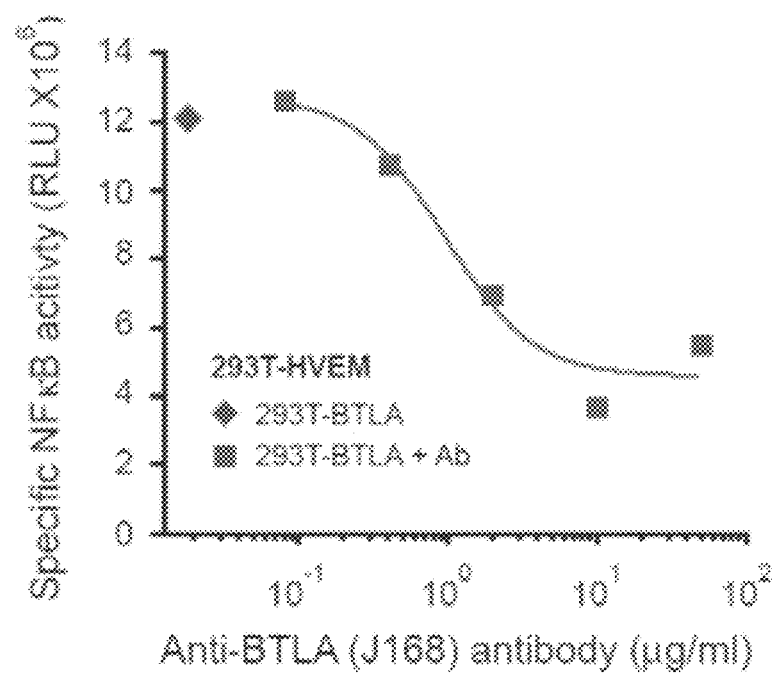

This Example Includes Studies Showing Non-Canonical Ligand Mediated HVEM Signaling BTLA did not activate HVEM signaling of NF-κB in the cis configuration (FIG. 3B); however 293T-BTLA cells mixed with 293T-HVEM cells expressing the NF-κB reporter (trans configuration) induced a specific, dose-dependent activation of NF-κB Luciferase expression (FIG. 4A). By contrast, the HVEM-Y61A mutant, which does not bind BTLA, failed to activate NF-κB when membrane BTLA was expressed in trans (FIG. 4B, left panel). However, membrane LIGHT induced dose-dependent luciferase activity in HVEM-Y61A cells (FIG. 4B, right panel) demonstrating this mutation specifically impacts BTLA-dependent activation of NF-κB. A mouse anti-human BTLA antibody (J168) blocked binding of HVEM-Fc to BTLA (FIG. 4C, left panel) and inhibited HVEM dependent NF-κB signaling induced by 293T-BTLA cells, confirming the specificity of BTLA-mediated HVEM signaling (FIG. 4C, right panel).

Figure 4E:
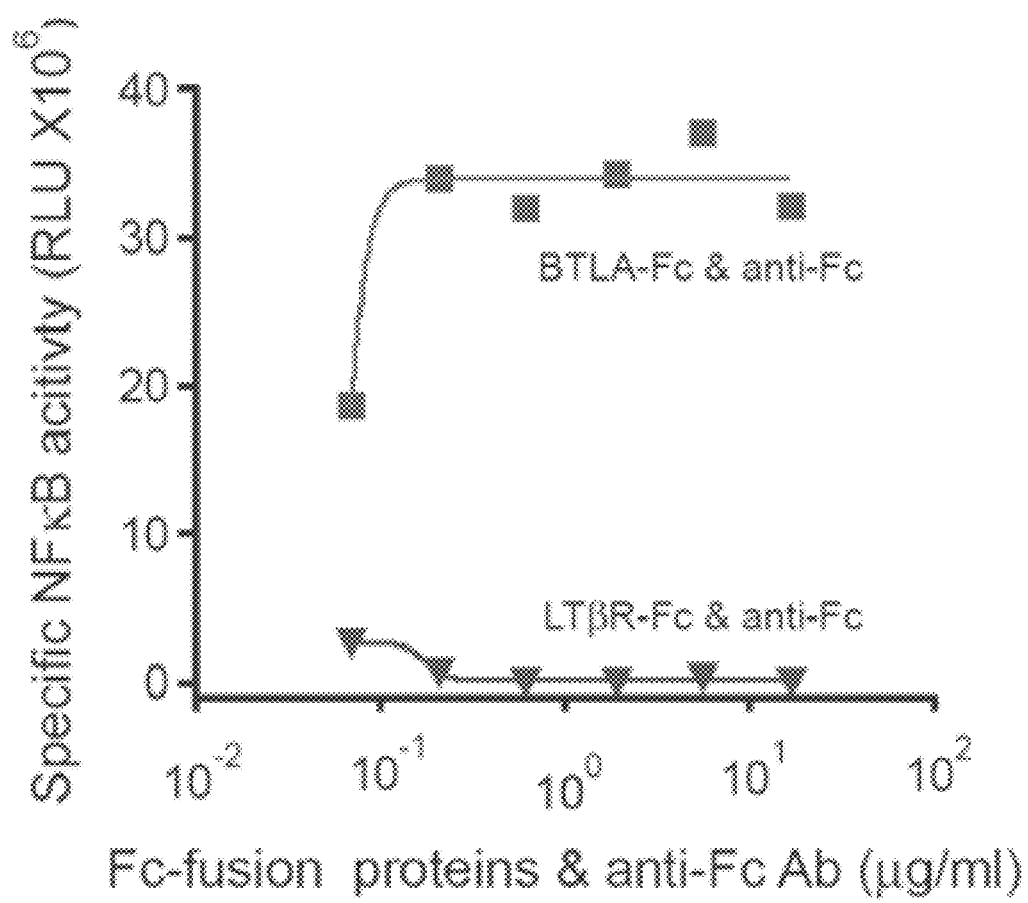

Soluble BTLA-Fc induced NF-κB dependent luciferase activity in 293T-HVEM cells mimicking cell expressed BTLA (FIG. 4D). BTLA-Fc activated HVEM signaling in a dose dependent manner while LTβR-Fc failed to activate NF-κB activation (FIG. 4D). BTLA-Fc-mediated HVEM signaling was enhanced when anti-Fc antibody was added to oligomerize BTLA-Fc bound to HVEM (FIG. 4E). These results indicate the BTLA-Fc fusion protein represents a functional surrogate of trans-interacting membrane BTLA.

Figure 4F:
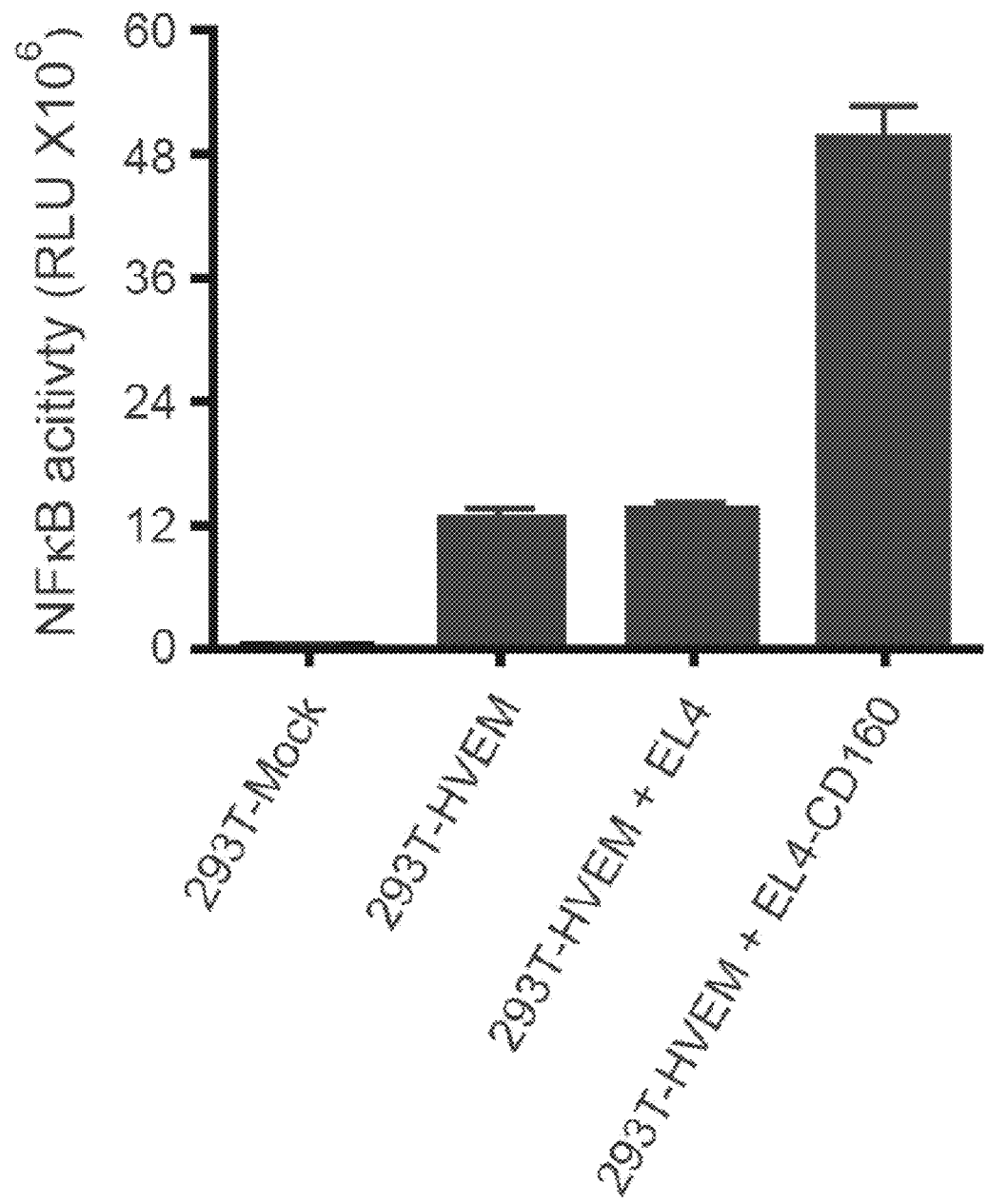
Figure 4G:
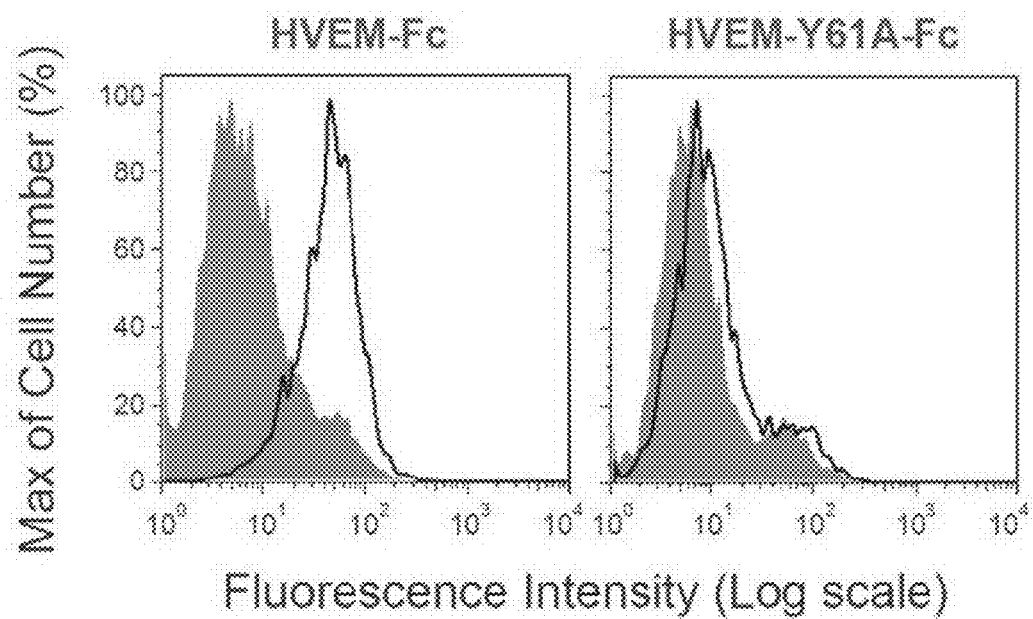
Figure 4H:
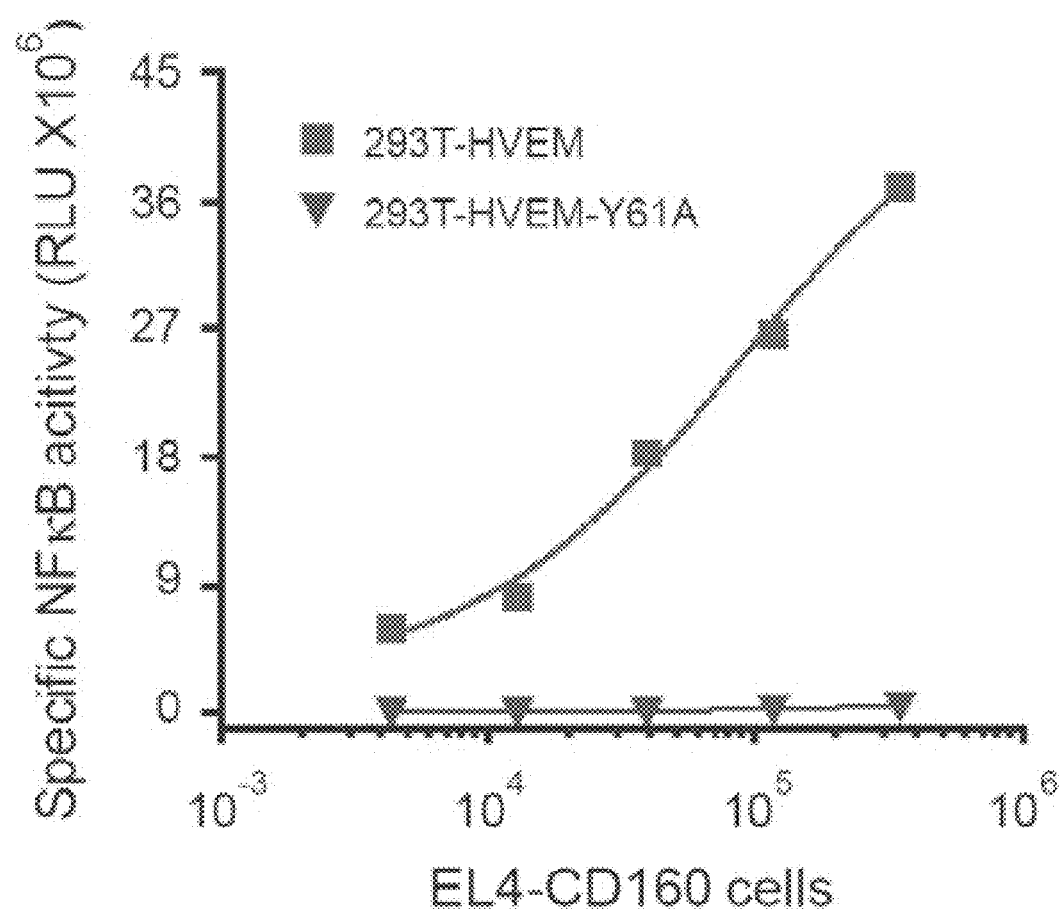

CD160, another non-canonical ligand for HVEM (Cai, et al., *Nat Immunol* (2008) 9:176), stably expressed in EL4 cells when mixed in trans with HVEM expressing 293T cells specifically activated NF-κB luciferase reporter (FIG. 4F), similarly to BTLA. HVEM-Fc containing Y61A mutation failed to bind CD160 expressed on EL4 cells (FIG. 4G) and the Y61A mutation in HVEM failed to activate in the presence of EL4-CD160 cells (FIG. 4H). These results indicate the CD160 binding site on HVEM is similar to the site recognized by BTLA.

Figure 4I:
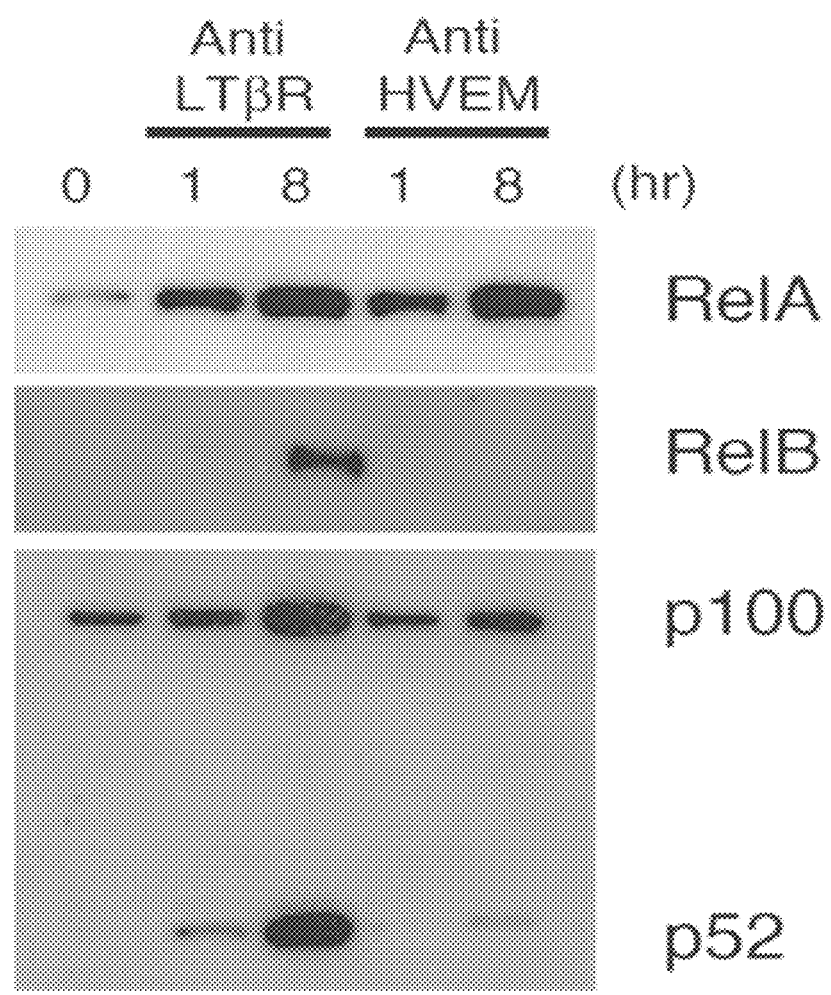
Figure 4J:
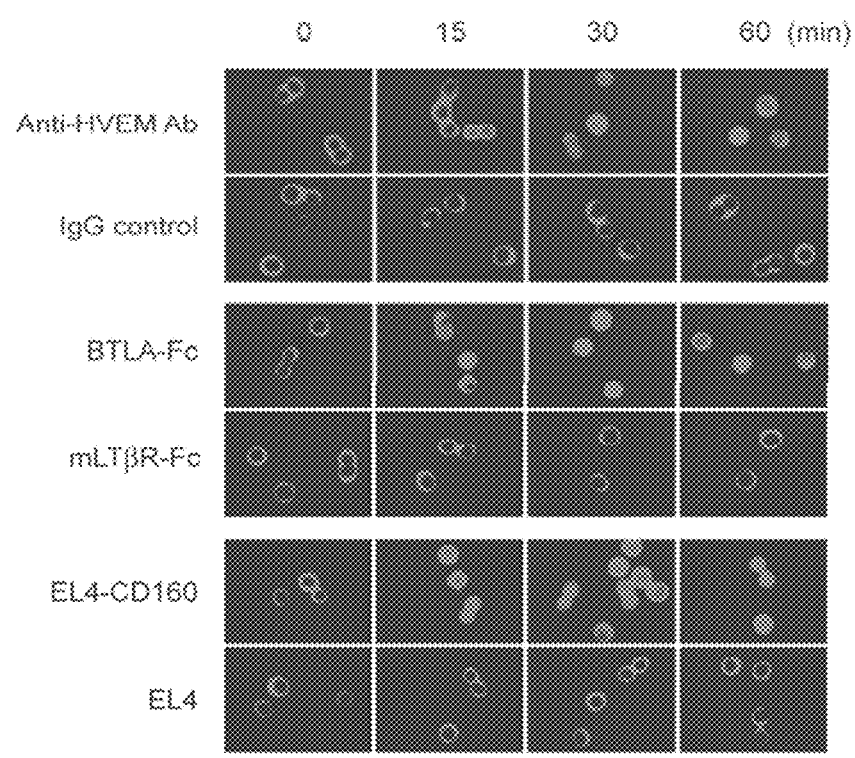

The human colon adenocarcinoma cell line, HT29, naturally expresses HVEM and LTβR (Rooney, et al., *J Biol Chem* (2000) 275:14307), but not BTLA, CD160, or LIGHT, providing a cellular system limited to trans interactions with HVEM ligands. Trans signaling by either HVEM or LTβR specific antibodies revealed in Western blots that HVEM ligation in HT29 cells activated the Rel A form of NF-κB, whereas LTβR was competent in activating both Rel A and Rel B forms of NF-κB, and inducing p100 processing (Dejardin, et al., *Immunity* (2002) 17:525) (FIG. 4I). Visualized by immunohistochemistry, ligation of HVEM in HT29 cells with BTLA-Fc, but not LTβR-Fc, induced nuclear Rel A translocation, as did EL4-CD160 expressing EL4 cells, but not by control cells (FIG. 4J).

Example 7

Figure 5B:
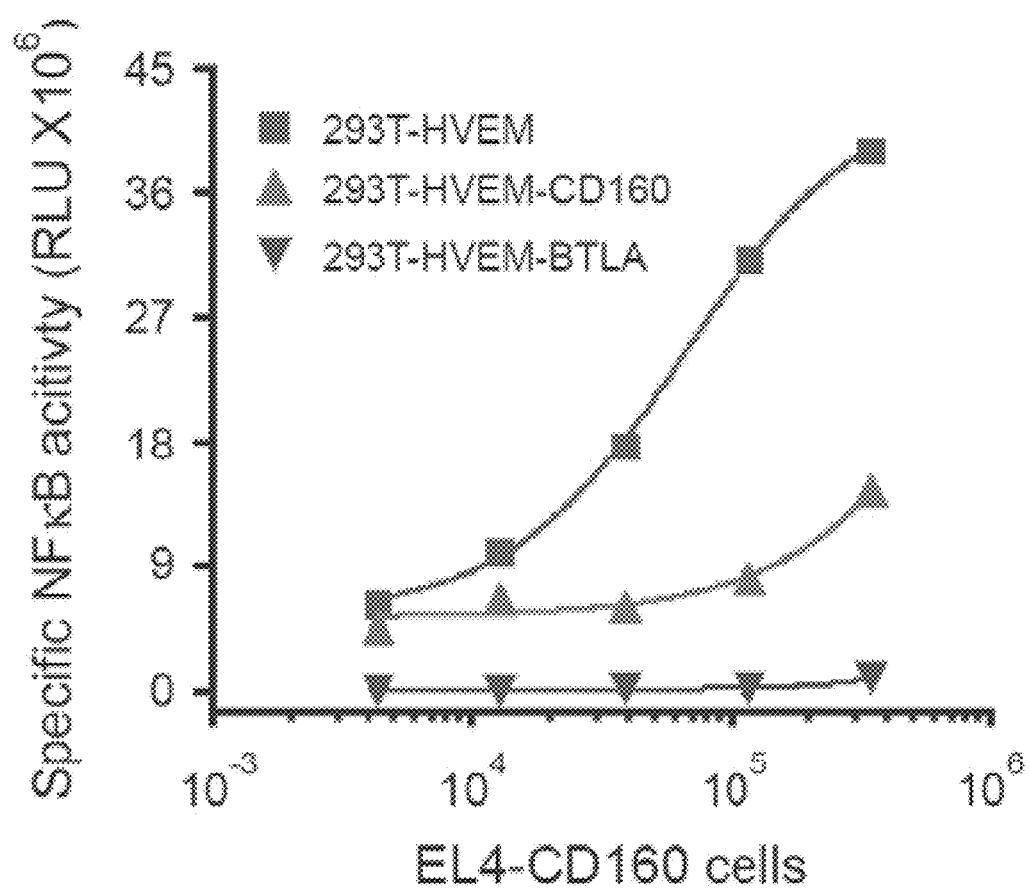

This Example Includes Studies Showing that HVEM-BTLA Cis Interaction Ablates NF-κB Activation HVEM ligated in trans with BTLA or CD160 activated NF-κB Rel A as efficiently as membrane LIGHT. However, HVEM configured in cis with BTLA failed to activate NF-κB when ligated with BTLA in trans (FIG. 5A) or with CD160 expressing cells (FIG. 5B). HVEM coexpressed with CD160 also suppressed NF-κB activation when ligated with CD160, but less than HVEM-BTLA in cis (FIG. 5B).

Figure 5C:
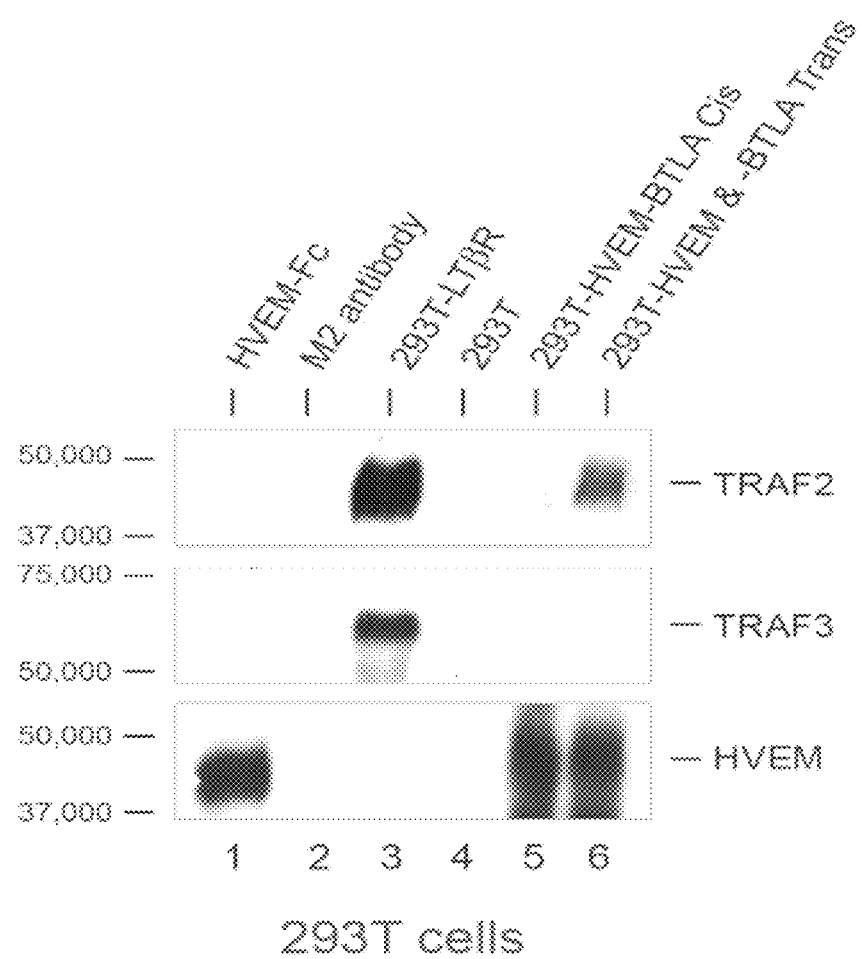

LIGHT-mediated HVEM signal transduction recruits TRAF2 the cytoplasmic tail of HVEM (Rooney, et al., *J Biol Chem* (2000) 275:14307). TRAF recruitment to HVEM was examined by coimmunoprecipitation and Western blot in HVEM expressing cells ligated with BTLA in cis or trans. Following incubation of cells for 30 min at room temperature, HVEM was immunoprecipitated and individual TRAF molecules detected by Western blotting. TRAF2 but not TRAF3 specifically coimmunoprecipitated with HVEM following BTLA stimulation in trans (FIG. 5C). The functionality of TRAF3 recruitment to LTβR, but not with HVEM, indicated HVEM signals specifically through TRAF2 accounting for selective RelA activation, as TRAF3-NIK is the primary pathway for Rel B activation (Basak, et al., *Cell* (2007) 128(2):369). In contrast, cells that coexpressed HVEM and BTLA failed to recruit TRAF2 to HVEM suggesting HVEM-BTLA cis configuration limits NF-κB activation at the initial activation step in HVEM signaling (FIG. 5A).

Figure 5D:
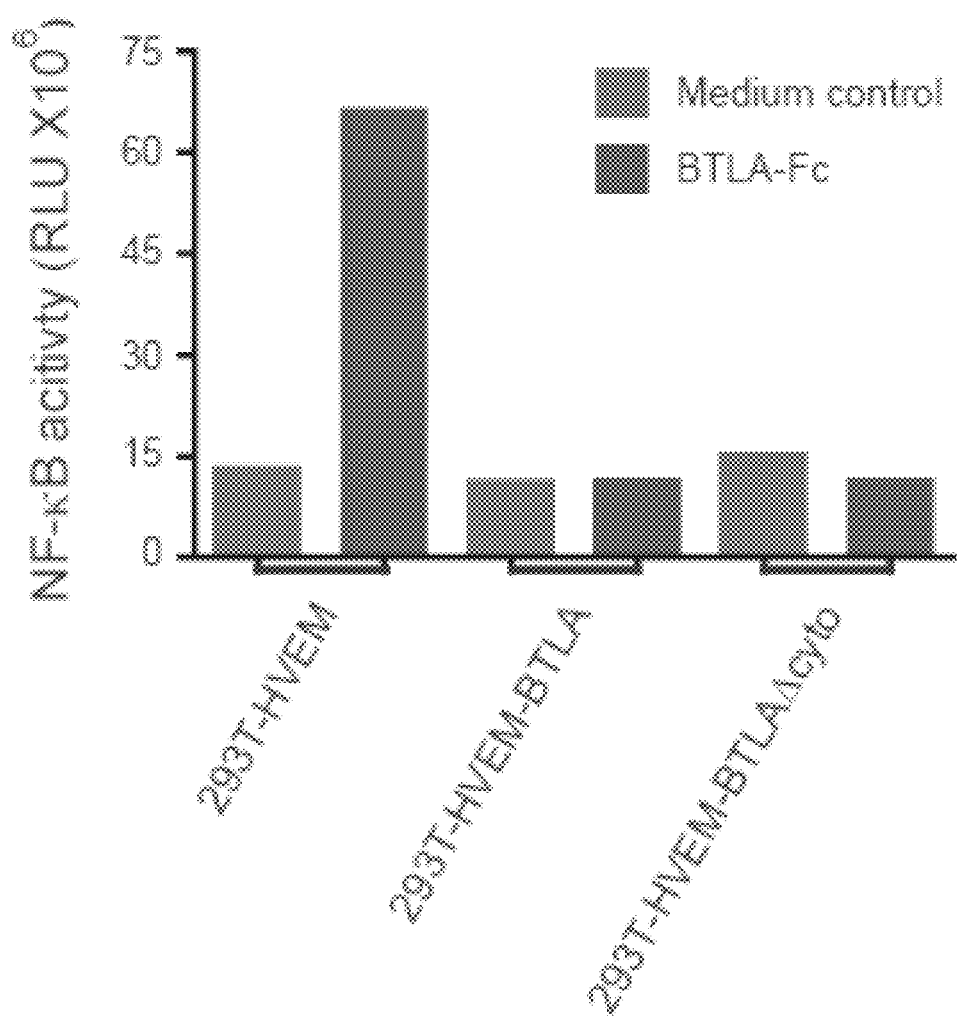

The foregoing results indicate that BTLA activation of HVEM signaling in trans, but not cis, is qualitatively similar to LIGHT, raising the question of whether LIGHT modifies BTLA activation of HVEM. Furthermore, the results indicate that HVEM-BTLA cis complex limited NF-κB activation at the initial activation step in HVEM signaling, principally interfering in TRAF2 recruitment to HVEM. In addition, BTLAΔcyto (a BTLA mutant lacking the cytoplasmic domain) when cotransfected with HVEM revealed the sufficiency of the BTLA ectodomain to inhibit HVEM signaling in trans (FIG. 5D).

The data indicate that in cis conformation, BTLA may prevent multimerization of HVEM, consistent with the observation that the cis conformation prevented recruitment of TRAF2, the earliest biochemical step in the process of HVEM signal activation. The HVEM-BTLA cis complex parallels regulatory receptors that recognize MHC, including the human leukocyte immunoglobulin-like receptors, which inhibit signaling via ITIM (Held, et al., *Nat Rev Immunol* 8:269 (2008)). The inhibitory receptor and MHC (e.g., Ly49A with H2-$D^d$) form both cis and trans complexes using the same binding site. Cis interactions may serve as a prominent feature of immunoreceptors that prevent activation of NK and T cells, thus aiding immune homeostasis.

Example 8

Figure 6A:
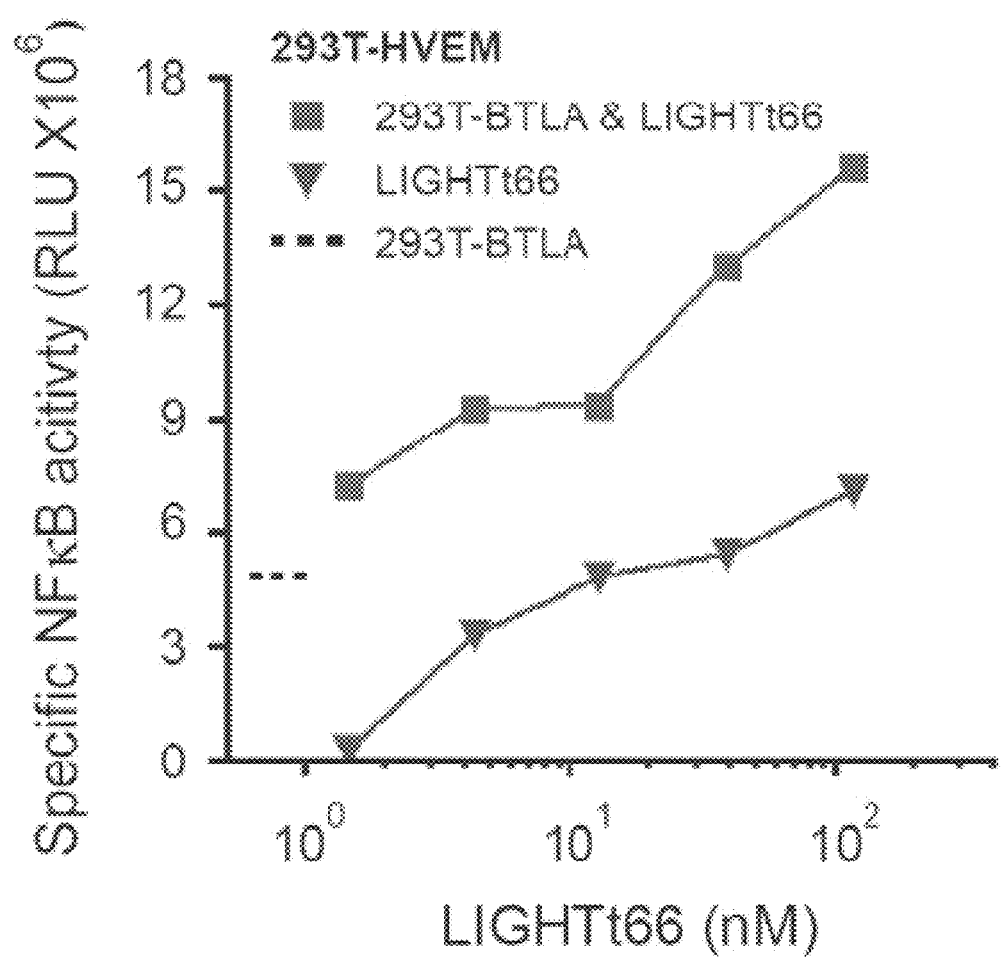

This Example Includes Studies Showing that Membrane and Soluble LIGHT Differentially Regulate Cis HVEM-BTLA Complex In a previous report, soluble LIGHT dose dependently enhanced binding between BTLA-Fc to membrane HVEM (Cheung, et al., *Proc Natl Acad Sci USA* (2005) 102:13218). Soluble LIGHT and BTLA-Fc can simultaneously occupy their respective binding sites on membrane HVEM. The enhanced binding of BTLA-Fc may reflect oligomerization of HVEM by soluble LIGHT, thus increasing the avidity BTLA-Fc. In accordance with enhanced binding, soluble LIGHT increased membrane BTLA activation of HVEM-dependent NF-κB activation, indicating that membrane BTLA and soluble LIGHT can cooperatively enhance HVEM signaling in the trans configuration (FIG. 6A).

In contrast to soluble LIGHT, HVEM-Fc binding to membrane LIGHT was inhibited by BTLA-Fc. This result suggested membrane LIGHT has the potential to act as a noncompetitive antagonist of the cis HVEM-BTLA complex, and reciprocally, BTLA acts to block LIGHT-mediated signaling when configured in cis with HVEM. Altering the equilibrium between HVEM-BTLA should favor the increased potential of membrane LIGHT to activate HVEM. To alter the HVEM-BTLA equilibrium an anti-BTLA antibody was used, which efficiently blocked trans-interaction between HVEM and BTLA (FIG. 4C). FRET analysis revealed that this anti-BTLA antibody resulted in a partial reduction of the FRET signal (FIG. 6B). This observation is similar to the inability of HVEM-Fc to compete effectively when BTLA is coexpressed with HVEM (FIG. 2A), confirming the unusual stability HVEM-BTLA cis-interaction.

Although membrane bound LIGHT was highly effective in activating HVEM in trans, the HVEM-BTLA cis complex attenuated the signaling capability of LIGHT (FIG. 6C). Addition of the anti-BTLA antibody to the coculture of EL4-LIGHT cells with HVEM-BTLA expressing 293T cells dramatically enhanced the induction of NF-κB directly proportional to the concentration of anti-BTLA antibody. The magnitude of NF-κB activation was similar to HVEM in the absence of BTLA (FIGS. 6C and 3C right panel). However, minimal induction of NF-κB occurred with either anti-BTLA or at this ratio of EL4-LIGHT cells (1:1). The anti-BTLA blocking antibody likely shifted the equilibrium towards unbound HVEM molecules on the cell surface, and the presence of membrane LIGHT continued to shift the equilibrium towards LIGHT-HVEM complexes, which highly activated HVEM signaling.

Example 9

Figure 6D:
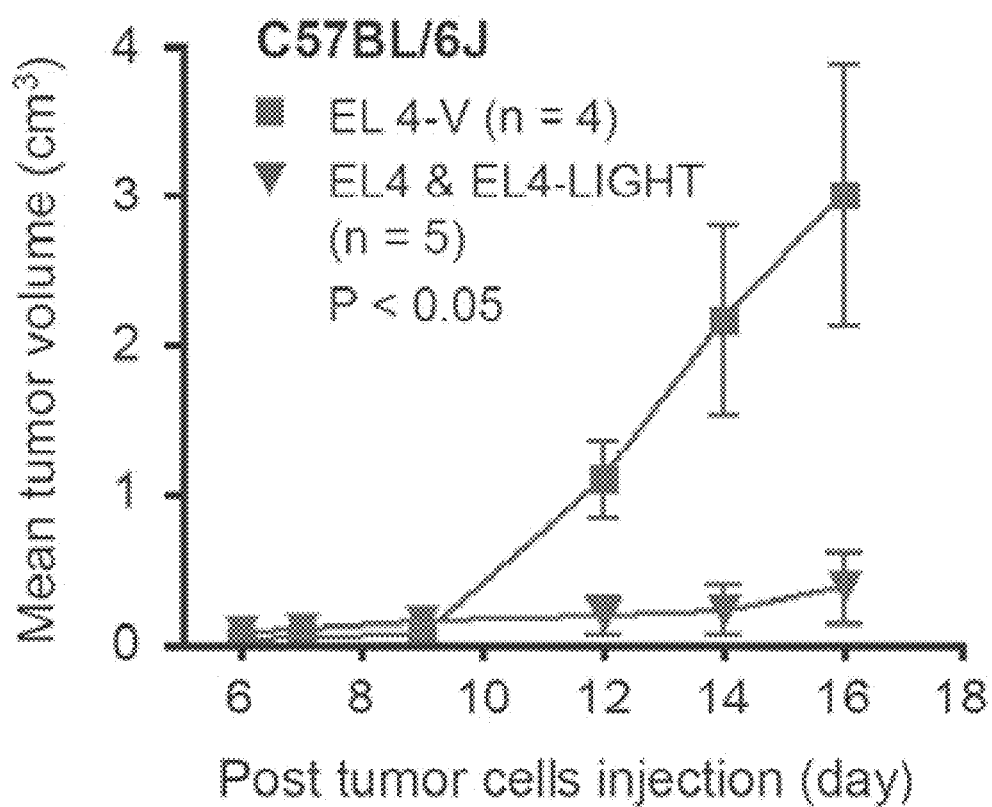
Figure 6E:
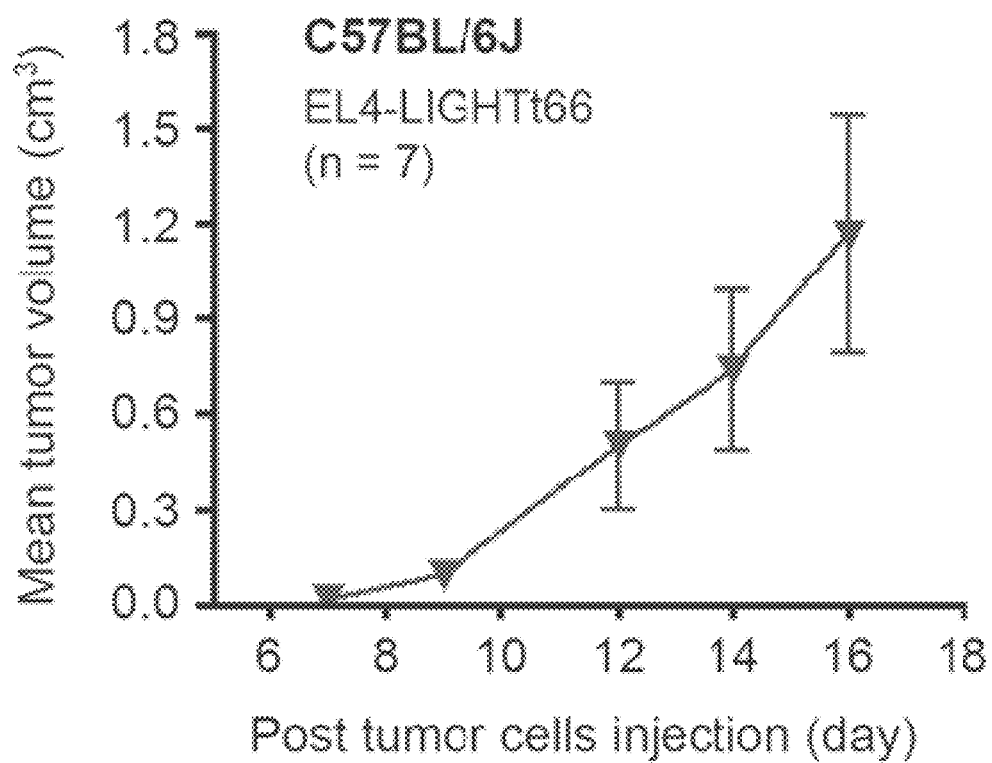

This Example Includes Data Showing that Membrane and Soluble LIGHT Regulate HVEM-BTLA Cis in Cellular Immune Responses The costimulatory activity of LIGHT can provide a powerful stimulus to the immune system in several physiological contexts including cancer (Shaikh, et al., *J Immunol* (2001) 167(11):6330; Lo, et al., *Science* (2007) 316(5822):285; Yu, et al., *Nat Immunol* (2004) 5(2):141). Ectopic expression of LIGHT on the surface of tumor cells results in tumor rejection mediated via tumor-specific cytotoxic T cells. To investigate the role of membrane and soluble LIGHT in regulating the HVEM-BTLA cis complex, a tumor rejection model with EL4 thymoma cells expressing bicistronic, retroviral vector-driven membrane LIGHT (EL4-LIGHT), soluble LIGHTt66 (EL4-LIGHTt66) or empty vector (EL4-V) was utilized. EL4-LIGHT and EL4-V lines were selected for expression of a similar level of GFP. The expression of GFP in the EL4-LIGHTt66 line was around 10 folds higher than the GFP level observed in the EL4-LIGHT. Importantly, all three cell-lines have the same doubling times in culture. Normally, EL4 cells ($2.5 \times 10^5$ cells) rapidly develop palpable subcutaneous tumor of 1.5-3 $cm^3$ over 16 days (FIG. 6D). The rejection of syngeneic EL4 thymoma in C57B1/6 (B6) mice requires stimulating T cell responses. In this model, EL4-V cells were injected subcutaneously alone as positive control. For the test group, parental EL4 cells were injected subcutaneously and at the same site equal number of EL4-LIGHT cells were also injected as the immune stimulus. EL4-LIGHT cells strongly inhibited growth of the parental EL4 cells (FIG. 6D). In contrast, soluble LIGHT expressing EL4 (EL4-LIGHTt66) cells were unable to stimulate an immune response that prevented tumor growth (FIG. 6E).

Figure 6F:
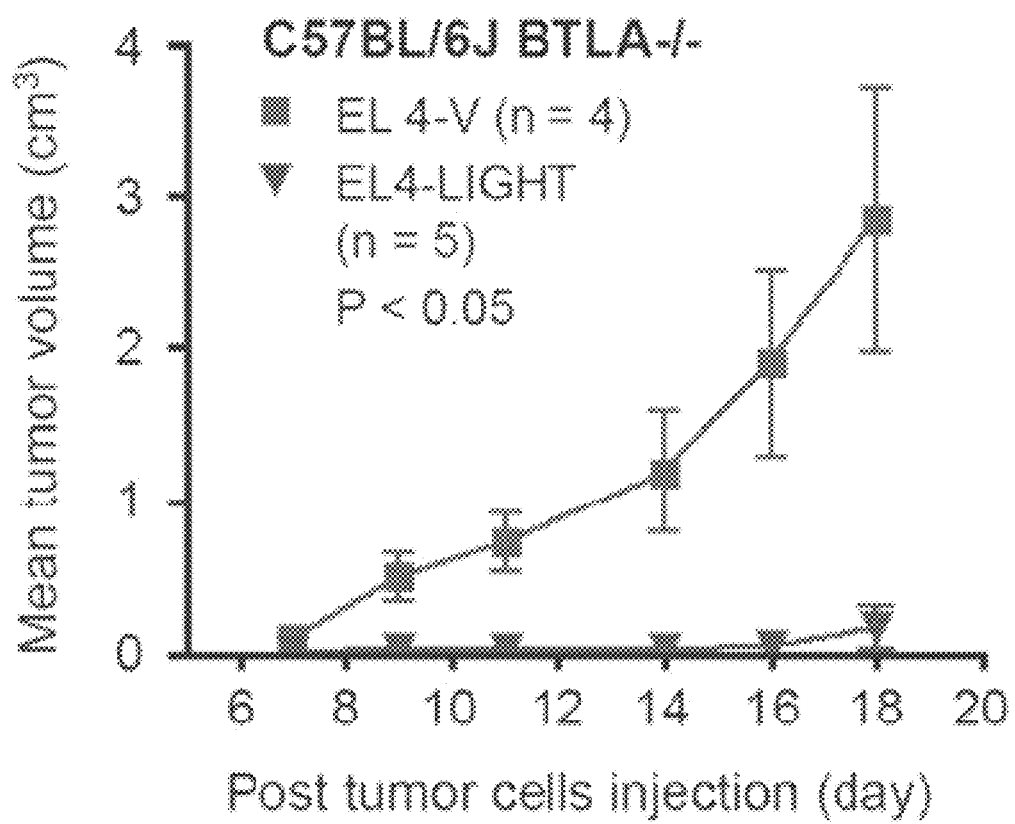
Figure 6G:
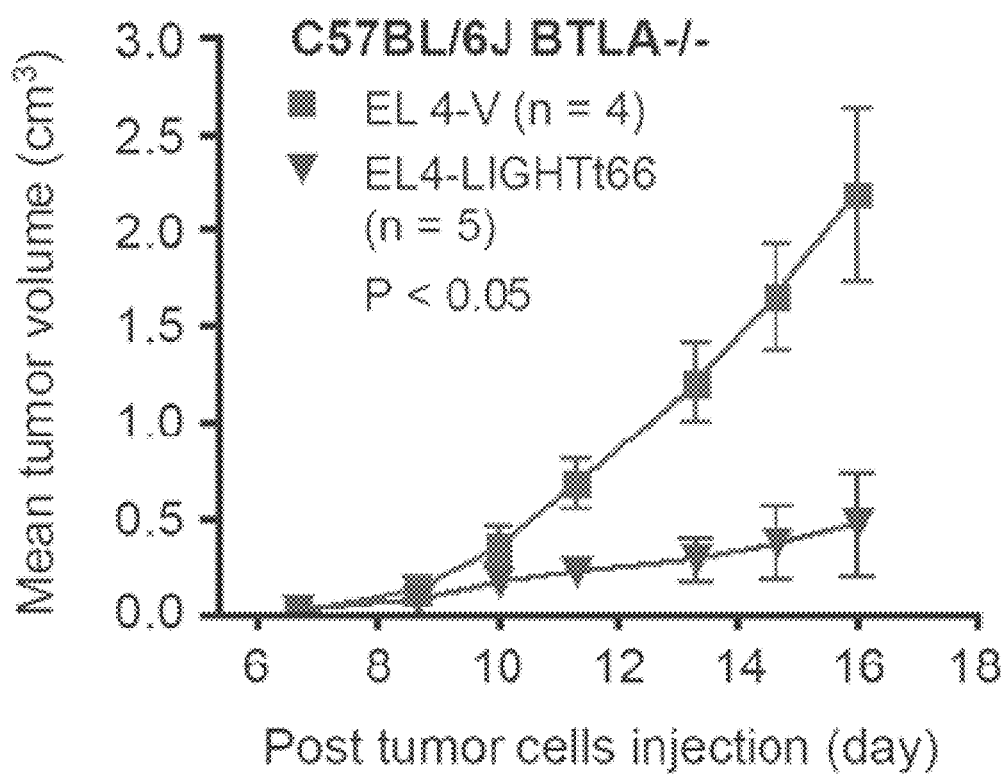

Soluble LIGHT can activate HVEM in the absence of BTLA (trans configuration) (FIG. 3C, left panel). B6 mice genetically deficient in BTLA were used as the host to examine the effector function of membrane LIGHT and soluble LIGHT in regulating HVEM in the absence of HVEM-BTLA cis-association. Interestingly, both EL4-LIGHT and EL4-LIGHTt66 cells acquired the ability to stimulate tumor rejection in BTLA−/− mice (FIGS. 6F and G)), in contrast to wild type B6 mice. This result indicates that the immune inhibitory effect of soluble LIGHT is genetically linked to BTLA, and furthermore establishes the EL4-LIGHTt66 cells are not inherently resistant to stimulating immune responses.

Figure 6H:
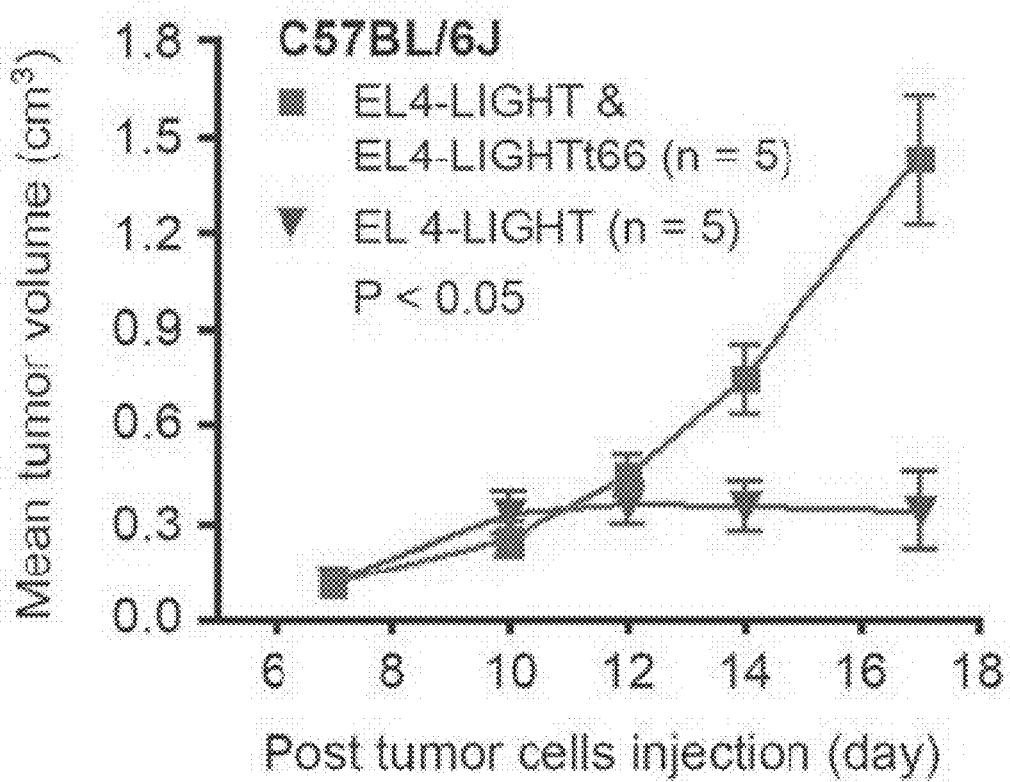

Soluble LIGHT acts as an inhibitor of membrane LIGHT-mediated HVEM signaling in HVEM-transfected 293T cells (FIG. 3D). To determine whether the presence of soluble LIGHT could inhibit membrane LIGHT-mediated tumor rejection, a mixture of EL4-LIGHT and EL4-LIGHTt66 (1:1 ratio) were transplanted into normal B6 mice and the growth of tumor was measured. As expected, tumor regression was observed in the mice injected with only EL4-LIGHT; however, tumor rejection mediated by EL4-LIGHT was inhibited by the presence EL4-LIGHTt66. This result indicates that soluble LIGHT can enhance attenuation of immune responses mediated by membrane LIGHT when HVEM associates with BTLA in cis (FIG. 6H).

Example 10

This Example Includes Studies Showing Species Differences in CD160 Binding HVEM

Human CD160 stably expressing EL4 (EL4-CD160) cells were prepared by infection of recombinant retrovirus using pMIG expression system. Flow cytometric based saturation binding analyses were performed. Graded concentrations (0.01-200 μg/ml) of human HVEM-Fc (▼) or mouse HVEM-Fc (■) were added to the cells in binding buffer (PBS with 2% FCS) for 45 min, washed and stained with APC conjugated goat anti-human IgG Fcγ (Jackson Immuno-Research, West Grove, Pa.) and mean fluorescence values were with fitted to nonlinear regression and EC50 values were calculated using Prism software (version 4).

Figure 7:
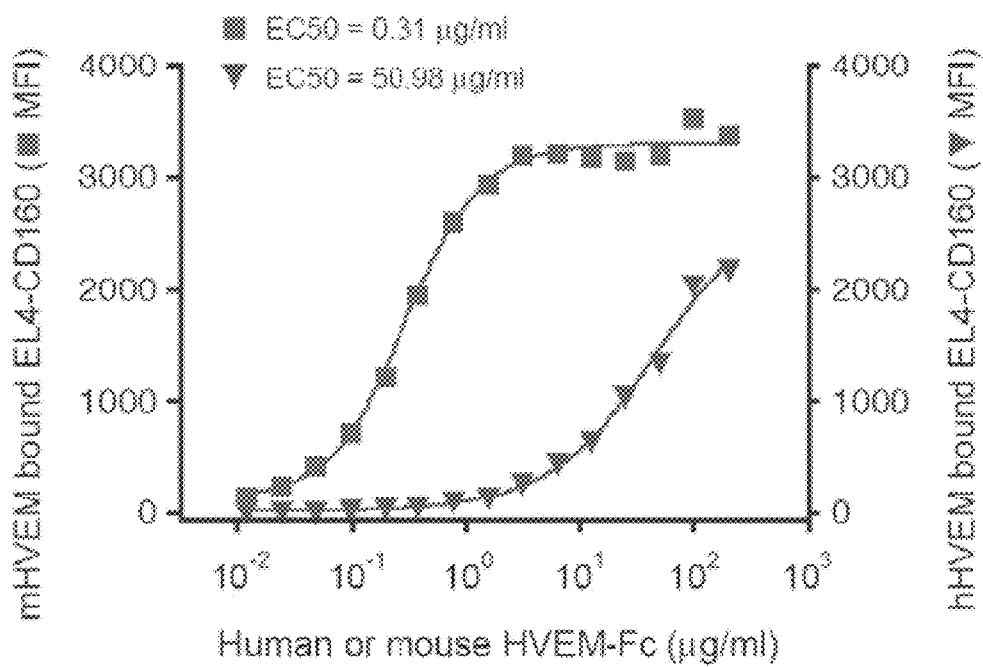
FIG. 7 shows mouse HVEM-Fc had a significantly enhanced higher CD160 binding avidity compared to human HVEM-Fc.

The binding interaction between mouse and human HVEM-Fc with human CD160 was analyzed as a model for directing mutagenesis of human HVEM and CD160 in order to enhance the pharmacodynamics of these ligands for better modulation of the endogenous molecules was analyzed. Surprisingly, mouse HVEM-Fc had a significantly enhanced (~160 fold) higher binding avidity compared to human HVEM-Fc (FIG. 7). These results demonstrated the possibility that key point mutations in human HVEM or CD160 could be generated to enhance the binding recombinant HVEM-Fc or CD160-Fc enhancing the pharmacodynamics for better efficacy in alleviating disease symptoms.

Example 11

Figure 8A:
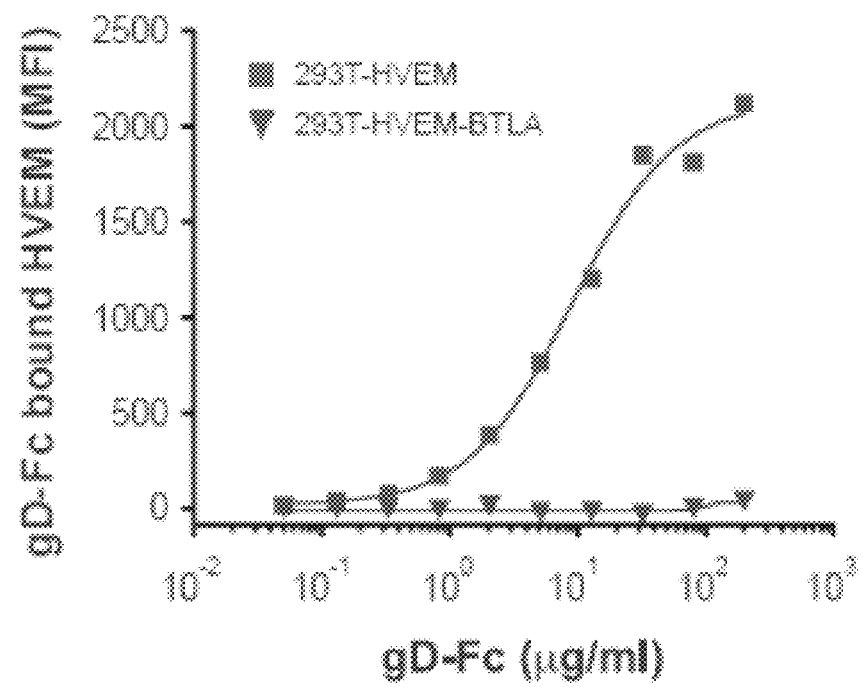
FIG. 8A to FIG. 8C show comparative in vitro binding and studies of HVEM/BTLA cis complex and HVEM to gD. (A) Saturation binding assay for gD-Fc binding to 293T-HVEM or 293T-HVEM-BTLA. 293T cells were transfected with HVEM and/or BTLA expression plasmids. Graded concentrations of gD-Fc were added to the transfected cells in binding buffer (PBS with 2% FCS) for 45 min, washed and stained with PE conjugated anti-rabbit IgG (left panel). Saturation binding assay for BTLA-Fc binding to 293T-HVEM or 293T-HVEM-gD. 293T cells were transfected with HVEM and/or gD expression plasmids. Graded concentrations of BTLA-Fc were added to the transfected cells in binding buffer. Binding analyses were carried out as in the left panel. RPE conjugated goat anti-human IgG Fcγ was used as secondary antibody (right panel). (B) HVEM-gD cis-interaction alters LIGHT-mediated HVEM signaling. NF-κB dependent luciferase reporter vector was transfected into 293T-HVEM, 293T-gD and 293T-HVEM-gD coexpressing cells. LIGHT expressing EL4 cells (EL4-LIGHT) were cocultured with the prepared cells for 24 hrs and then assessed for luciferase activity in cell lysates. EL4 cells were used as negative controls (left panel). The level of NF-κB activation mediated by EL4-LIGHT was determined by the equation as follows: (EL4-LIGHT mediated RLU/EL4 mediated RLU)−1. For comparison, the level of EL4-LIGHT mediated NF-κB activation on 293T-HVEM cells was set at 100 units (right panel). (C) HVEM-gD cis-interaction alters gD-mediated HVEM signaling. Transfected cells were prepared as in (B). gD-Fc (20 µg/ml) was added to the cells for 24 hrs and then assessed for luciferase activity in cell lysates. Rabbit IgG (20 µg/ml) were used as negative control (left panel). The level of NF-κB activation mediated by gD was determined by the equation above (right panel).
Figure 8A:
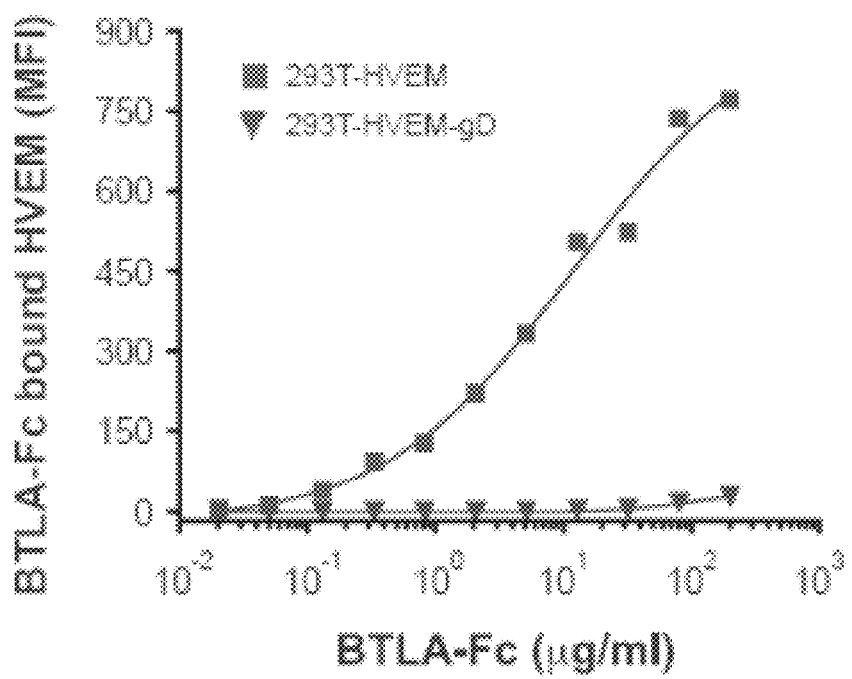

This Example Includes Studies Showing that Herpesvirus gD Manipulates the HVEM-BTLA Cis Complex Herpes simplex virus gD, the namesake ligand, engages HVEM in the same site as the cellular ligands BTLA and CD160, and thus is another probe to evaluate the function of the HVEM-BTLA cis complex. To study the effect of HVEM-BTLA cis complex on gD-HVEM interaction, the binding of gD-Fc to 293T cells expressing HVEM, or HVEM and BTLA was studied. As expected, gD-Fc bound specifically and with a saturable dose response to HVEM (FIG. 8A, left panel). However, in cells coexpressing both HVEM and BTLA (with BTLA in slight excess), gD-Fc was unable to bind HVEM (FIG. 8A, left panel). Co-expression of gD with HVEM in 293T cells also blocked BTLA-Fc binding, indicating that HVEM and gD form stable cis complexes when coexpressed in the same cells (FIG. 8A, right panel). These results suggest that the HVEM-BTLA or HVEM-gD cis complexes reciprocally serve as inhibitors of trans signaling.

Figure 8B:
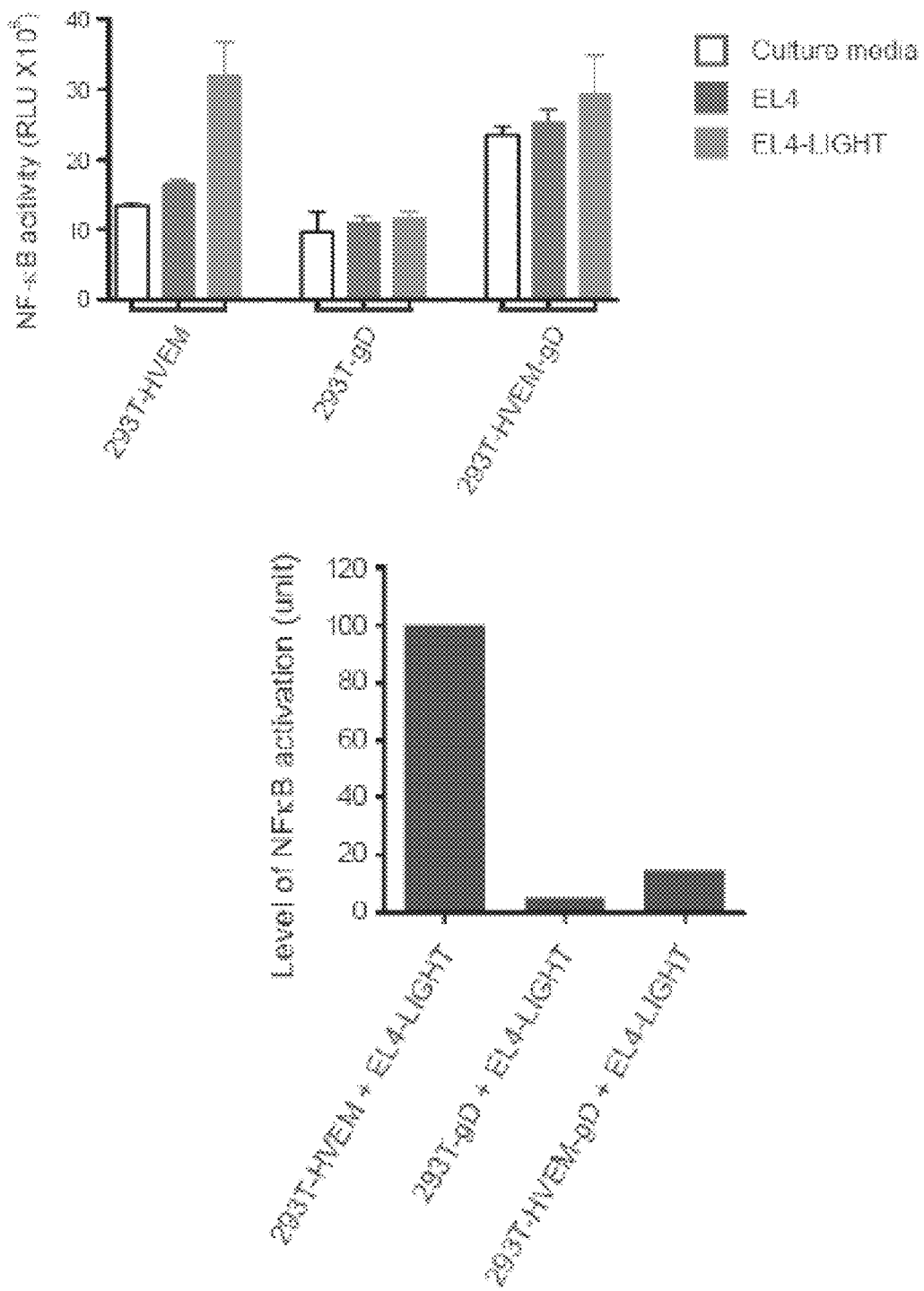
Figure 8C:
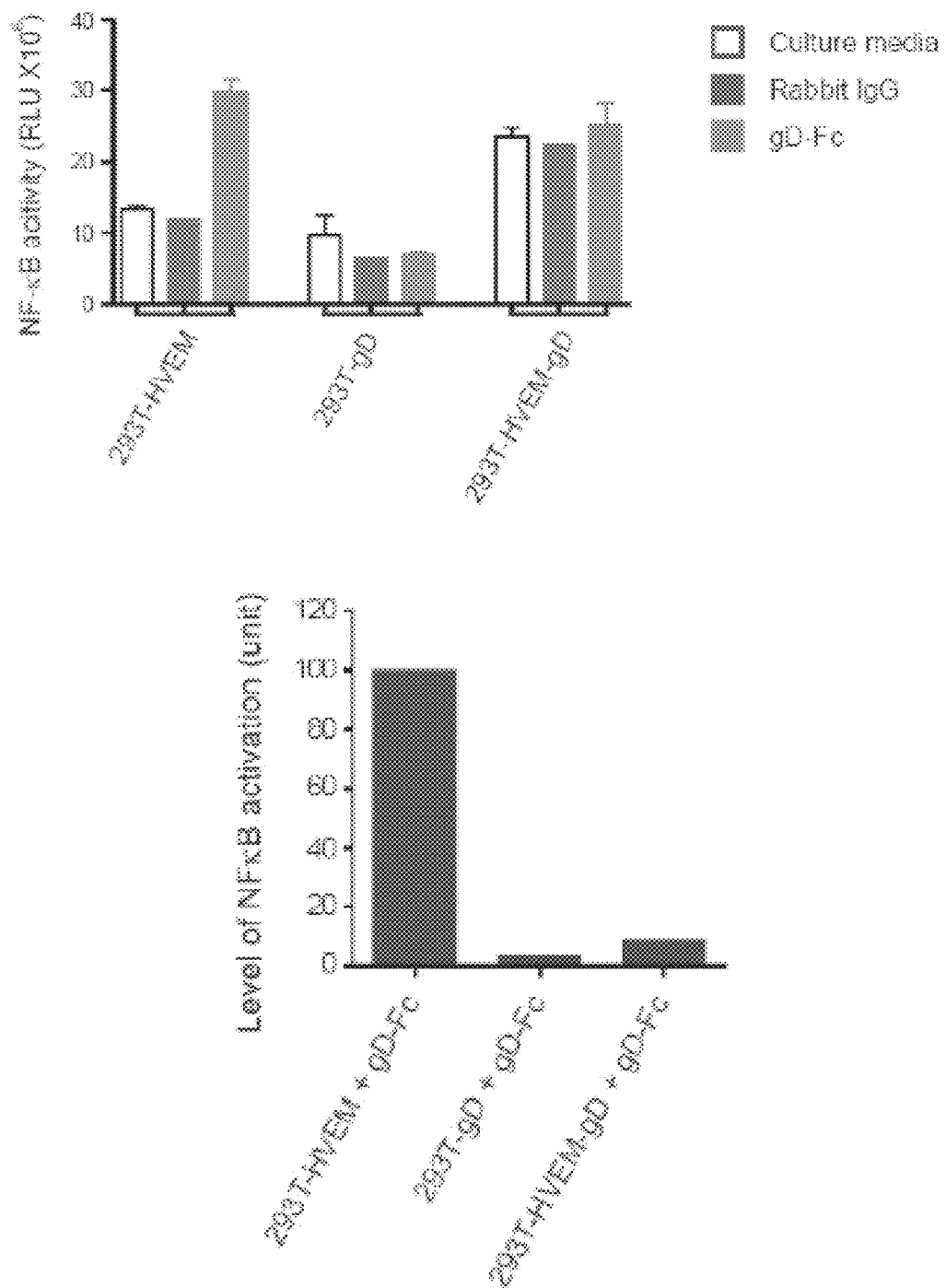

To determine whether the HVEM-gD cis complex modified HVEM signaling, EL4-LIGHT cells or gD-Fc were used to activate 293T cells expressing HVEM, gD or both. Cotransfection of gD with HVEM strongly activated NF-κB dependent signaling (FIG. 8B, left panel and FIG. 8C, left panel). In contrast to HVEM-BTLA cis complex, HVEM-gD cis complex inhibited membrane LIGHT from further activating HVEM (FIG. 8B, right panel). Similarly, coexpression of gD and HVEM made 293T cells unresponsive to further stimulation with gD-Fc (FIG. 8C, right panel). These results indicate that gD in cis association with HVEM inhibits trans activation of HVEM.

In contrast to the cellular ligands, envelope gD constitutively activated NF-κB when coexpressed with HVEM, reflecting the insidious nature of herpesvirus. The regulation of prosurvival genes by NF-κB may provide HSV with a selective advantage early during infection. Ligand induced clustering of HVEM serves as the activating mechanism, common to all TNFR. HSV gD activates HVEM in cis, implicating a conformational difference between the HVEM-gD and HVEM-BTLA cis complexes. The inhibitory effect of the HVEM-BTLA cis complex implies BTLA may prevent multimerization of HVEM while the activating effect of the HVEM-gD complex suggests gD may induce HVEM clustering. Even though gD engages the same site on HVEM as BTLA, gD also inhibits the binding of soluble and membrane LIGHT to HVEM. The structure of gD, although substantially different from BLTA, does not reveal a clear mechanism of how it competes with LIGHT for binding to HVEM.

gD expressed in cis with HVEM blocked trans activation by LIGHT, BTLA and CD160, similar to the HVEM-BTLA cis complex, thus interfering with signals from cells in the surrounding microenvironment. Herpesvirus gD mediates viral interference in which the initial infecting pathogen blocks further infection (Nicola, et al., *J Virol* 71:2940 (1997), Dean, et al., *J Virol* 69:5171 (1995)). Perhaps analogous to viral interference, the inhibitory function of the HVEM-BTLA cis complex can be viewed as interference of cellular signals from the surrounding microenvironment. The remarkable diversity in viral mimicry of the HVEM-BTLA complex (Kinkade, et al., *Trends Immunol* 27:362 (2006) suggests this pathway serves as a key selective pressure driving evolution of host defenses (Sedy, et al., *Nat Rev Immunol* 8:861 (2008)). The NF-κB activating function of the HVEM pathway in regulating effector T cell survival may reflect this evolutionary selective pressure.

Example 12

Figure 9A:
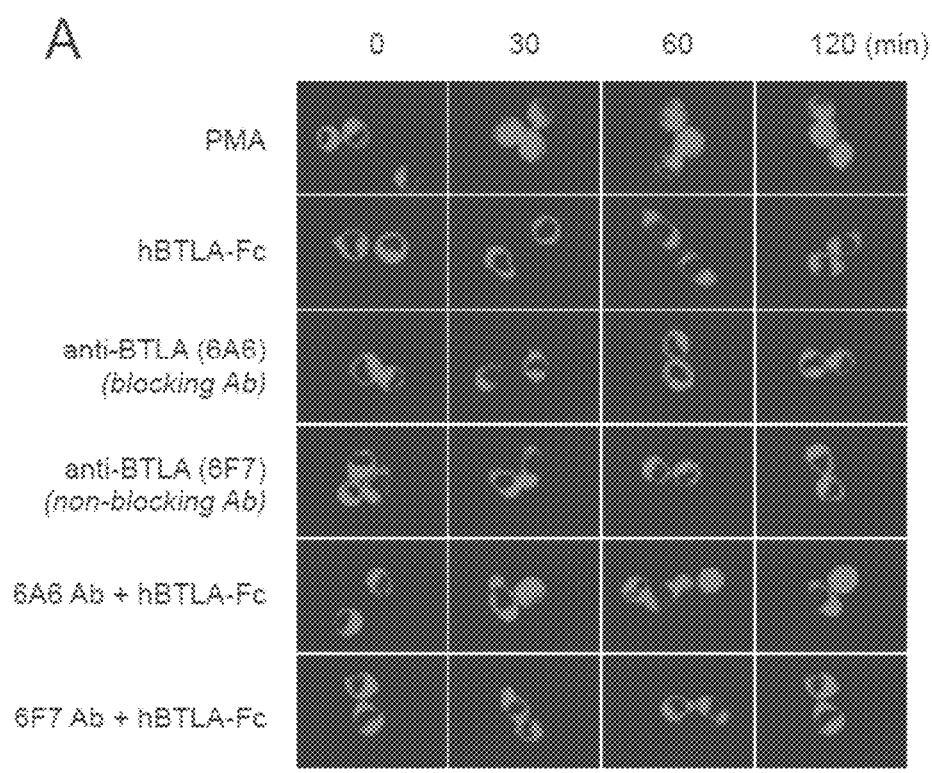
FIG. 9A to FIG. 9B show the impact of the HVEM-BTLA cis complex on T cell activation BTLA-mediated HVEM trans signaling in T cells. (A) BTLA-mediated HVEM trans signaling in T cells Immunocytochemical staining for RelA translocation was performed on T cell hybridoma cells following incubation with PMA (50 ng/ml), BTLA-Fc (15 µg/ml), or the combination of antagonist anti-BTLA (6A6) antibody or non blocking anti-BTLA (6F7) antibody (20 µg/ml). (B) Intrinsic HVEM and BTLA requirement for effector T cell survival. Co-transfer of $1\times10^6$ WT (CD45.1$^+$) and $1\times10^6$ Btla−/− (CD45.2$^+$) naïve T cells into Btla−/−Rag−/− or Hvem−/−Rag−/− recipients. Mice were euthanized 2 weeks post-transfer and the ratio of CD45.1$^+$ and CD45.2$^+$ cells in the spleens were analyzed by FACS.

This Example Includes Studies Showing the Impact of the HVEM-BTLA Cis Complex on T Cell Activation To determine whether the cis complex limits HVEM-dependent NF-κB activation in T cells, the mouse PE16 T cell hybridoma, which expresses the cis HVEM-BTLA complex was studied. Disruption of the HVEM-BTLA cis complex with a direct blocking antibody to mouse BTLA (as in FIGS. 4C, 6B and 6C) should predictably shift the equilibrium towards free HVEM. Concurrently, human BTLA-Fc (lacking cross reactivity with mouse BTLA) was added to initiate trans engagement of HVEM, and assessed the level of RelA nuclear translocation in PE16 cells (FIG. 9A). In a time-dependent fashion, the combination of the blocking anti-mouse BTLA mAb (6A6) and human BTLA-Fc specifically induced Rel A nuclear localization in PE16 T cells. In contrast, the non-blocking anti-BTLA mAb (6F7) combined with human BTLA-Fc failed to induce nuclear accumulation of Rel A, as did any of the reagents alone. This result indicates that the HVEM-BTLA cis complex is an inhibitor of trans activation of HVEM in T cells.

The data indicate that HVEM and BTLA interact in a dynamic equilibrium, with the cis heterodimer forming a stable complex, suggesting the cis conformation is an energetically favorable state. The dramatic enhancement of HVEM signaling by combining anti-BTLA, itself a weak antagonist for HVEM-BTLA cis complex, with membrane LIGHT (FIG. 6C and FIG. 9A) supports a conformational equilibrium model. In this case, BTLA in cis is considered an inhibitor of LIGHT, and reciprocally membrane LIGHT is considered as an antagonist of HVEM-BTLA cis complex. The topographically distinct binding sites mapped for BTLA and LIGHT on HVEM indicate a noncompetitive mechanism controls the ability of membrane LIGHT to activate HVEM in either the trans or cis complex with BTLA (Cheung, et al., *Proc Natl Acad Sci USA* 102:13218 (2005)). Membrane LIGHT, but not its soluble form, blocks BTLA binding without occupying the binding site, indicating LIGHT sterically displaces BTLA from HVEM, shifting the equilibrium toward free HVEM (Cheung, et al., *Proc Natl Acad Sci USA* 102:13218 (2005)). The intrinsically higher avidity of LIGHT for HVEM compared to BTLA should favor the actively signaling LIGHT-HVEM complex. However, the inducible, yet transient expression in activated T cells suggests a limited dynamic range for LIGHT in regulating the HVEM-BTLA cis complex. In addition, during T cell activation, the relative expression levels of HVEM change (Sedy, et al., *Nat Immunol* 6:90 (2005)), initially decreased HVEM expression, then increased after T cell activation, offering the opportunity for engagement of ligands in trans. Thus, these two distinct classes of ligands for HVEM serve as opposing forces directing the equilibrium of the HVEM-BTLA cis complex towards inhibitory or stimulating signals.

Figure 9B:
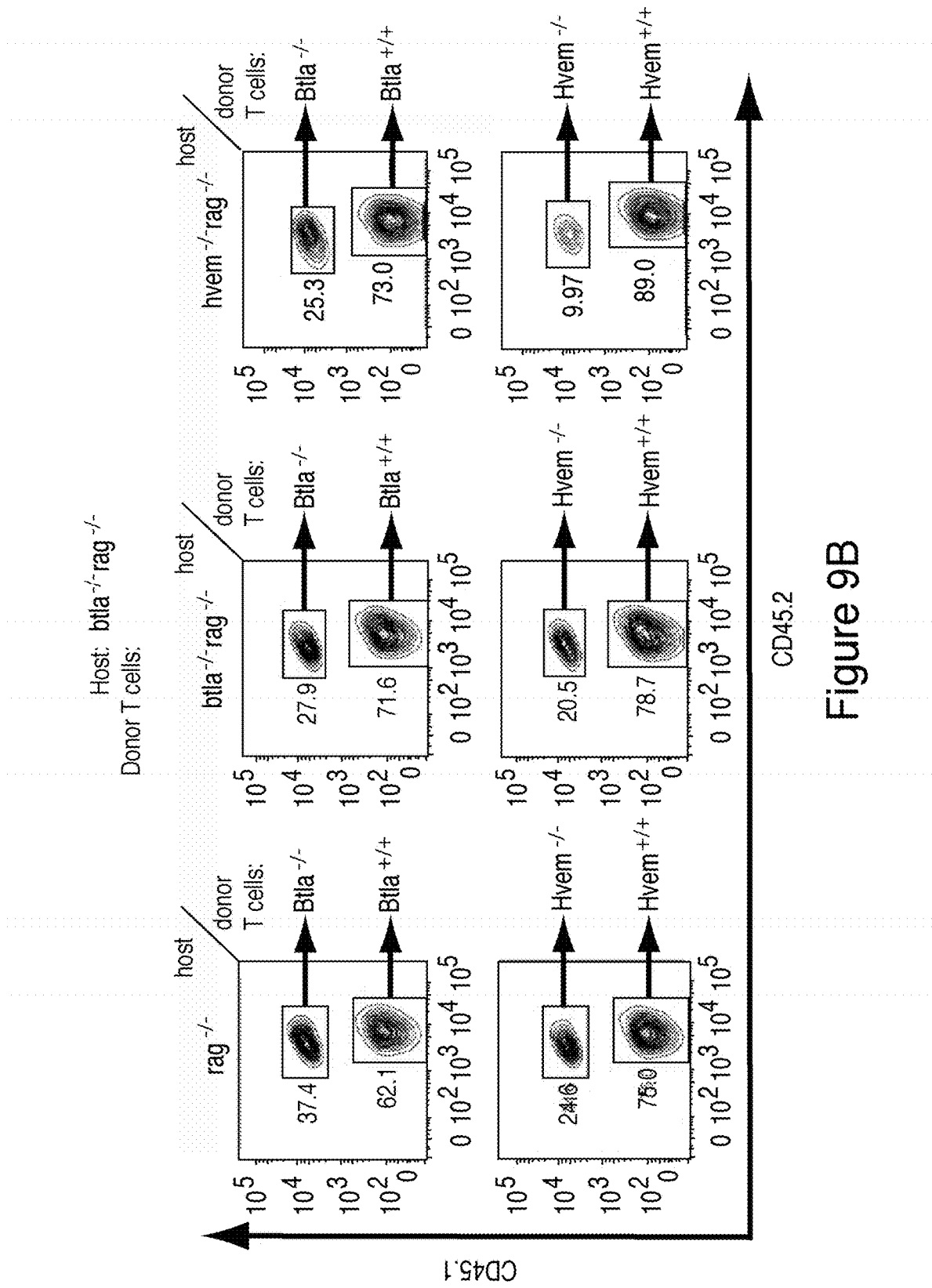

In the colitis model, Btla$^{-/-}$ T cells transferred into Rag$^{-/-}$ hosts failed to accumulate, with the reduced number of effector T cells in the recipients ultimately affecting the onset of colitis (Steinberg, et al., *J Exp Med* 205:1463 (2008)). T cell cotransfer studies were performed to determine whether T cell accumulation in this model also depended on HVEM. Equal numbers of wild type naïve CD4$^+$CD45RB$^{high}$ T cells (CD45.2$^+$) and congenically marked CD45.1$^+$CD45.2$^+$ CD4$^+$CD45RB$^{high}$ T cells isolated from Btla$^{-/-}$ or Hvem$^{-/-}$ mice were transferred into Rag$^{-/-}$ mice or Rag$^{-/-}$ mice deficient for either Hvem or Btla. The use of Hvem$^{-/-}$Rag$^{-/-}$ and Btla$^{-/-}$Rag$^{-/-}$ recipients restricted the expression of HVEM and BTLA specifically to the donor T cells, which allowed direct evaluation in T cells. The results demonstrated that T cells from mice deficient in Btla or Hvem failed to accumulate in the different recipients. Indeed, following naïve T cell cotransfer into the different Rag$^{-/-}$ hosts, higher percentages of wild type T cells accumulated in spleens, MLN, lamina propria and intestinal intraepithelium of the transferred animals than congenically marked knockout T cells (FIG. 9B).

The cotransfer of wild type T cells with Btla$^{-/-}$Hvem$^{-/-}$ double deficient T cells yielded similar results. Importantly, Rag$^{-/-}$ recipients cotransferred with Btla$^{-/-}$ (CD45.2$^+$) or Hvem$^{-/-}$ (CD45.2$^+$) T cells and congenic marked (CD45.1$^+$) wild type T cells also accumulated lower percentages of the knockout T cells, demonstrating that reduced T cell accumulation in Rag$^{-/-}$ mice was unrelated to the presence of the congenic gene in the T cells. These results indicated that the accumulation of pathogenic effector T cells in Rag$^{-/-}$ recipients required both BTLA and HVEM. In view of the fact that neither the host environment, nor wild type T cells influenced the accumulation of the cotransferred HVEM- and/or BTLA-deficient T cells indicated a requirement for the expression of both molecules in the same cell.

The data indicate a dual role of the HVEM-BTLA system in cell—cell communication and cell autonomous regulation of T cell survival. BTLA deficient T cells fail to survive during inflammatory responses in vivo (Steinberg, et al., *J Exp Med* 205:1463 (2008), Hurchla, et al., *J Immunol* 178:6073 (2007)). Although Btla$^{-/-}$ T cells responded normally in both models, effector T cells failed to accumulate and altered the disease course. Btla$^{-/-}$ and wild type T cells showed comparable proliferation and number of divisions following cell stimulation in culture. BTLA-Fc specifically activated NF-κB RelA, increased the percentage of 7-AAD-negative, proliferating cells and rescued survival of Btla$^{-/-}$ T cells, indicating the defect in cell survival occurs after cell division. These results provide a mechanistic explanation for the role of BTLA in T cell survival (Cheung, et al., *Proc. Nat. Acad. Sci.* (2009)). In this regard, HVEM behaves akin to its TNFR paralogs, CD27, OX40 and 41BB, which provide key cosurvival signals during T cell activation Croft, M. *Nat Rev Immunol* 3:609 (2003)). These cosignaling TNFR paralogs utilize similar mechanisms of activating cell survival programs via TRAF, NF-κB and AKT dependent pathways (Song, et al., *Immunity* 22:621 (2005); however, they do not appear to be redundant in their individual roles in T cell differentiation.

The mouse CD4 T cell transfer model of colitis results demonstrate a T cell intrinsic requirement for BTLA and HVEM in the accumulation of pathogenic T cells. The outcome of this genetic study (FIG. 6B) indicated that effector cell accumulation required both HVEM and BTLA, indicating a functional role for the HVEM/BTLA cis complex in T cells. The predominant expression of the cis complex on naïve T cells implicates its role in regulating effector cell accumulation during the T cell activation program. Biochemical evidence indicates HVEM does not activate NF-κB dependent signals in the cis complex, indicating BTLA may provide the intrinsic survival mechanism in the cis complex.

The relatively wide distribution of BTLA and HVEM throughout the hematopoietic compartment, as well as HVEM expression in epithelial cells, indicates that the HVEM-BTLA regulatory mechanism can influence other cell lineages. For example, subsets of myeloid DC differ in their relative levels of BTLA, with CD8α$^+$ DC subset expressing ~10 fold more BTLA than detected on the CD4$^+$ DC subset, yet both subsets express similar levels of HVEM (De Trez, et al., *J Immunol* 180:238 (2008)). Bone marrow repopulation studies revealed intrinsic and exogenous expression of both HVEM and BTLA influenced DC reconstitution in the spleen. These results indicate that both cis and trans interactions between BTLA and HVEM are physiologically important in the context of DC and T cells.

What is claimed:

1. A method of inhibiting, reducing, decreasing, or blocking a T cell response in a subject having Crohn's disease comprising administering to the subject a soluble LIGHT polypeptide, wherein the soluble LIGHT polypeptide binds to a cis complex comprising a herpes virus entry mediator (HVEM) polypeptide and a B- and T-lymphocyte attenuator (BTLA) polypeptide, or a cis complex comprising a HVEM polypeptide and a CD160 polypeptide, thereby inhibiting, reducing, decreasing, or blocking the T cell response in the subject having Crohn's disease.

2. The method of claim 1, wherein the T cell response comprises inflammation.

3. The method of claim 1, wherein the T cell response comprises T cell activation.

4. The method of claim 3, wherein the T cell activation comprises secretion of a cytokine, chemokine, interleukin, or interferon.

5. The method of claim 4, wherein the cytokine comprises TNF, lymphotoxin (LT)-alpha, LT-beta, LIGHT, or a ligand for CD27, OX40, 41BB; wherein the chemokine comprises CCL21, 19, or CXCL13; wherein the interleukin comprises IL10, IL2, IL7, or IL15; or wherein the interferon comprises type 1, or Interferon-gamma.

6. The method of claim 3, wherein the T cell activation comprises cytotoxic or helper activity of the activated T cells.

7. The method of claim 1, wherein the subject is a mammal.

8. The method of claim 1, wherein the subject is a human.

9. A method of inhibiting, reducing, decreasing, attenuating, preventing or blocking proliferation, survival, differentiation, activity or signaling of T cells in a subject having Crohn's disease, comprising contacting said T cells in the subject with a soluble LIGHT polypeptide sequence that binds to a cis complex comprising a herpes virus entry mediator (HVEM) polypeptide binding to B- and T-lymphocyte attenuator (BTLA) polypeptide, or a cis complex comprising a herpes virus entry mediator (HVEM) polypeptide binding CD160 polypeptide, in an amount sufficient to inhibit, reduce, decrease, attenuate, prevent or block proliferation, survival, differentiation, or activity of said T cells in the subject having Crohn's disease.

10. The method of claim 9, wherein said contacting is in a subject in need of inhibiting, reducing, decreasing, attenuating, preventing or blocking proliferation, survival, differentiation, or activity of T cells.

11. A method of inhibiting, reducing, decreasing, attenuating, preventing or blocking a T cell immune response or inflammatory response, comprising administering to a subject having Crohn's disease an amount of soluble LIGHT polypeptide sequence that binds to a cis complex comprising herpes virus entry mediator (HVEM) polypeptide binding to B- and T-lymphocyte attenuator (BTLA) polypeptide, sufficient to inhibit, reduce, decrease, attenuate, prevent or block the T cell immune response or inflammatory response in the subject having Crohn's disease.

* * * * *